(12) United States Patent
Bilgicer et al.

(10) Patent No.: US 10,874,751 B2
(45) Date of Patent: Dec. 29, 2020

(54) NANOALLERGENS AND USES THEREOF

(71) Applicant: University of Notre Dame du Lac, South Bend, IN (US)

(72) Inventors: Zihni Basar Bilgicer, South Bend, IN (US); Peter Edward Deak, South Bend, IN (US); Tanyel Kiziltepe Bilgicer, South Bend, IN (US); Jared Francis Stefanick, South Bend, IN (US); Jonathan Darryl Ashley, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 15 days.

(21) Appl. No.: 15/762,260

(22) PCT Filed: Sep. 26, 2016

(86) PCT No.: PCT/US2016/053816
§ 371 (c)(1),
(2) Date: Mar. 22, 2018

(87) PCT Pub. No.: WO2017/053991
PCT Pub. Date: Mar. 30, 2017

(65) Prior Publication Data
US 2018/0272008 A1 Sep. 27, 2018

Related U.S. Application Data

(60) Provisional application No. 62/232,978, filed on Sep. 25, 2015.

(51) Int. Cl.
| | | |
|---|---|---|
| *A61K 49/00* | (2006.01) | |
| *A61K 9/00* | (2006.01) | |
| *A61K 9/127* | (2006.01) | |
| *A61K 47/69* | (2017.01) | |
| *A61K 39/35* | (2006.01) | |
| *G01N 33/68* | (2006.01) | |
| *G01N 33/58* | (2006.01) | |
| *C12Q 1/40* | (2006.01) | |
| *A61K 39/00* | (2006.01) | |

(52) U.S. Cl.
CPC ........ *A61K 49/0006* (2013.01); *A61K 9/0014* (2013.01); *A61K 9/1271* (2013.01); *A61K 39/35* (2013.01); *A61K 47/6911* (2017.08); *C12Q 1/40* (2013.01); *C12Y 302/01052* (2013.01); *G01N 33/586* (2013.01); *G01N 33/686* (2013.01); *G01N 33/6854* (2013.01); *A61K 2039/60* (2013.01); *G01N 2800/24* (2013.01)

(58) Field of Classification Search
CPC .... A61K 49/00; A61K 49/0006; A61K 39/00; A61K 39/35; A61K 9/00; A61K 9/1271; A61K 9/0014; A61K 2039/60; A61K 47/00; A61K 47/6911; G01N 33/586; G01N 33/686; G01N 33/6854; G01N 2800/24; C12Y 302/01052; C12Q 1/40
USPC .......... 424/1.11, 1.21, 1.25, 1.29, 1.49, 1.57, 424/1.65, 1.69, 1.73, 9.1, 9.3, 9.32, 9.321, 424/9.51, 9.6, 9.8, 9.81, 400, 450
See application file for complete search history.

(56) References Cited

U.S. PATENT DOCUMENTS

| | | | |
|---|---|---|---|
| 4,812,402 A | 3/1989 | Nilsson | |
| 10,342,846 B2 * | 7/2019 | Bilgicer | ................. A61K 47/62 |
| 2012/0202890 A1 | 8/2012 | Wu | |
| 2014/0080730 A1 | 3/2014 | Dreskin et al. | |

FOREIGN PATENT DOCUMENTS

| | | | |
|---|---|---|---|
| WO | 2014121291 A2 | 8/2014 | |
| WO | WO-2014121291 A2 * | 8/2014 | ........... A61K 9/1271 |

OTHER PUBLICATIONS

Albrecht et al, "Relevance of IgE Binding to Short Peptides for the Allergenic Activity of Food Allergens" J Allergy Clin Immunol., 124(2):328-336, Aug. 2009.
Berin et al., "Food Allergy: An Enigmatic Epidemic," Trends Immunol. 34(8):390-397, Aug. 2013.
Bernard et al., "Allergenicity of Peanut Component ara h 2: Contribution of Conformational Versus Linear Hydroxyproline-Containing Epitopes," J Allergy Clin Immunol., 135(5):1267-1274, May 2015.
Boyce et al., "Guidelines for the Diagnosis and Management of Food Allergy in the United States: Summary of the NIAID-Sponsored Expert Panel Report," Nutrition, 27(2):253-267, Jan. 2011.
Chen et al., "Analysis of the Effector Activity of Ara h 2 and Ara h 6 by Selective Depletion from a Crude Peanut Extract,"J Immunol Methods, 372(1-2):65-70, Sep. 2011.
(Continued)

*Primary Examiner* — D. L. Jones
(74) *Attorney, Agent, or Firm* — Haukaas Fortius PLLC; Michael H. Haukaas

(57) ABSTRACT

Embodiments of the present disclosure provide a nanoparticle based platform, and nanoallergens for identifying, evaluating and studying allergen mimotopes as multiple copies of a single mimotope or various combinations on the same particle. The nanoparticle is extremely versatile and allows multivalent binding to IgEs specific to a variety of mimotopes, simulating allergen proteins. Nanoparticles can include various molecular ratios of components. For example, the nanoallergens can include about 0.1-40% mimotope-lipid conjugate and about 60-99.9% lipid. The mimotope-lipid conjugate includes a mimotope, a first linker, and lipid molecule. Nanoallergens can be used in in vitro and in vivo applications to identify a specific patient's sensitivity to a set of epitopes and predict a symptomatic clinical response, identify allergen epitopes through blind screening peptide sequences from allergen protein, and in a clinical application similar to a scratch test.

7 Claims, 63 Drawing Sheets

Specification includes a Sequence Listing.

(56) References Cited

OTHER PUBLICATIONS

Collins et al., "Rat Basophil Leukaemia (RBL) Cells Sensitized with Low Affinity IgE Respond to High Balency Antigen," Clin Exp Allergy., 26(8):964-970, Aug. 1996.
Davidson et al., "A High-throughput Shotgun Mutagenesis Approach to Mapping B-cell Antibody Epitopes," Immunology, 143(1):13-20, Sep. 2014.
Dibbern et al., "RBL Cells Expressing Human Fc Epsilon RI are a Sensitive Tool for Exploring Functional IgE-Allergen Interactions: Studies with Sera from Peanut-sensitive Patients," J. Immunol Methods, 274(1-2):37-45, Mar. 2003.
Gupta et al., "Childhood Food Allergies: Current Diagnosis, Treatment and Management Strategies," Mayo Clin. Proc., 88(5):512-526, May 2013.
Handlogten et al., "Design of a Heterobivalent Ligand to Inhibit IgE Clustering on Mast Cells," Chem Biol, 18(9):1179-1188, Sep. 2011.
Handlogten et al., "Design of a Heterotetravalent Synthetic Allergen that Reflects Epitope Heterogeneity and IgE Antibody Variability to Study Mast Cell Degranulation," Biochem J, 449:91-99, Jan. 2013.
Handlogten et al., "Inhibition of Weak-Affinity Epitope-IgE Interactions Prevents Mast Cell Degranulation," Nat Chem Biol, 9(12):789-795, Dec. 2013.
Handlogten et al., "Synthetic Allergen Design Reveals the Significance of Moderate Affinity Epitopes in Mast Cell Degranulation," ACS Chem Biol, 7(11):1796-1801, Nov. 2012.
Handlogten et al., "Two-Allergen Model Reveals Complex Relationship Between IgE Crosslinking and Degranulation," Chem Biol, 21(11):1445-1451, Nov. 2014.
Huber, M., "Activation/Inhibition of Mast Cells by Supra-optimal Antigen Concentrations.," Cell Commun Signal., 11(1):7, Jan. 2013.
International Search Report and Written Opinion of the ISA/US dated Feb. 3, 2017 in International Application No. PCT/US2015/053816; 15pgs.
Iwaki et al, "Btk Plays a Crucial Role in the Amplification of Fc EpsilonRI-mediated Mast Cell Activation by Kit," J Biol Chem., 280(48):40261-40270, Dec. 2005.
Kane et al., Cross-linking of IgE-Receptor Complexes by Rigid Bivalent Antigens Greater than 200 A in Length Triggers Cellular Degranulation. J Cell Biol, 107(3):969-980, Sep. 1998.
Lee et al., "Anaphylaxis: Mechanisms and Management," Clin Exp Allergy, 41(7):923-938, Jul. 2011.
Li et al., "Primary Sequence and Site-Selective Hydroxylation of Prolines in Isoforms of a Major Peanut Allergen Protein Ara h 2," Protein Sci., 19(1):174-182, Jan. 2010.
Lian et al., "Trends and Developments in Liposome Drug Delivery Systems," J Pharm Sci., 90(6):667-680, Jun. 2001.
Maleki et al., "Computationally Predicted IgE Epitopes of Walnut Allergens Contribute to Cross-Reactivity with Peanuts," Allergy, 66(12):1522-1529, Dec. 2011.
McDermott et al., "Contribution of Ara H 2 to Peanut-Specific, Immunoglobulin E-Mediated, Cell Activation," Clin Exp Allergy., 37(5):752-763, May 2007.
Mueller et al., "Ara h 2: Crystal Structure and IgE Binding Distinguish Two Subpopulations of Peanut Allergic Patients by Epitope Diversity," Allergy, 66(7):878-885, Jul. 2011.
Otsu et al., "Epitope Analysis of Ara h 2 and Ara h 6: Characteristic Patterns of IgE- binding Fingerprints Among Individuals with Similar Clinical Histories," Clin Exp Allergy, 45(2): 471-484, Feb. 2015.
Palmer et al., "Comparative Potency of Ara h 1 and Ara h 2 in Immunochemical and Functional Assays of Allergenicity," Clin Immunol., 115(3):302-312, Jun. 2005.
Posner et al., "A Quantitative Approach for Studying IgE-fc Epsilon RI Aggregation," Mol Immunol, 38(16-18):1221-1228, Sep. 2002.
Stanley et al., "Identification and Mutational Analysis of the Immunodominant IgE Binding Epitopes of the Major Peanut Allergen Ara H 2," Arch Biochem Biophys., 342(2):244-253, Jun. 1997.
Stefanick et al., "A Systematic Analysis of Peptide Linker Length and Liposomal Polyethylene Glycol Coating on Cellular Uptake of Peptide-targeted Liposomes," ACS Nano, 7(4):2935-2947, Apr. 2013.
Stefanick et al., "Enhanced Cellular Uptake of Peptide-targeted Nanoparticles Through Increased Peptide Hydrophilicity and Optimized Ethylene Glycol Peptide-linker Length," ACS Nano, 7(9):8115-8127, Aug. 2013.
Tanabe, "Epitope Peptides and Immunotherapy," Curr Protein Peptide Sci, 8(1):109-118, Feb. 2007.
Tang, "A Practical Guide to Anaphylaxis," Am Fam Physician, 68(7):1325-1332, Oct. 2003.

* cited by examiner

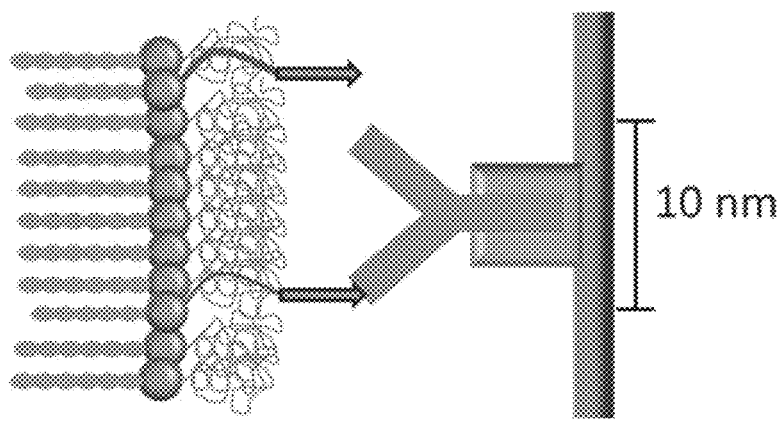
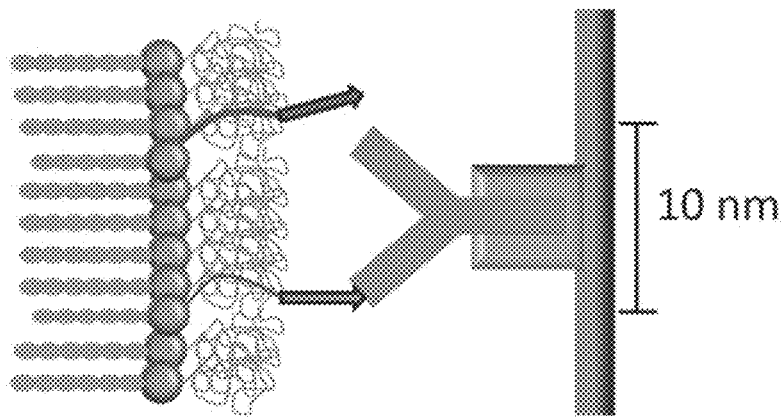
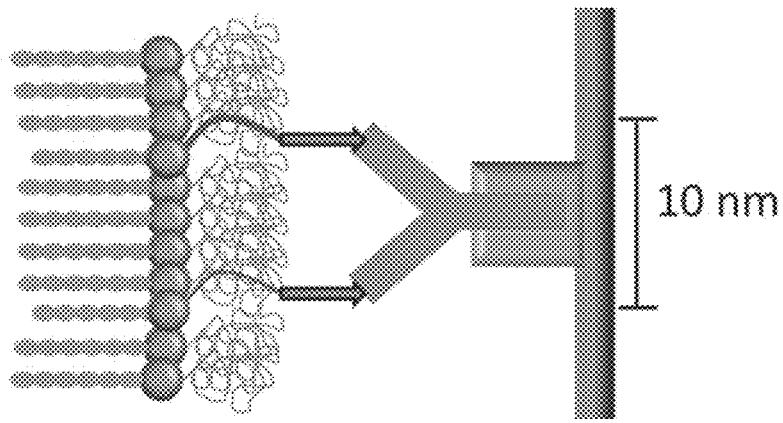
*FIG. 28A-C*

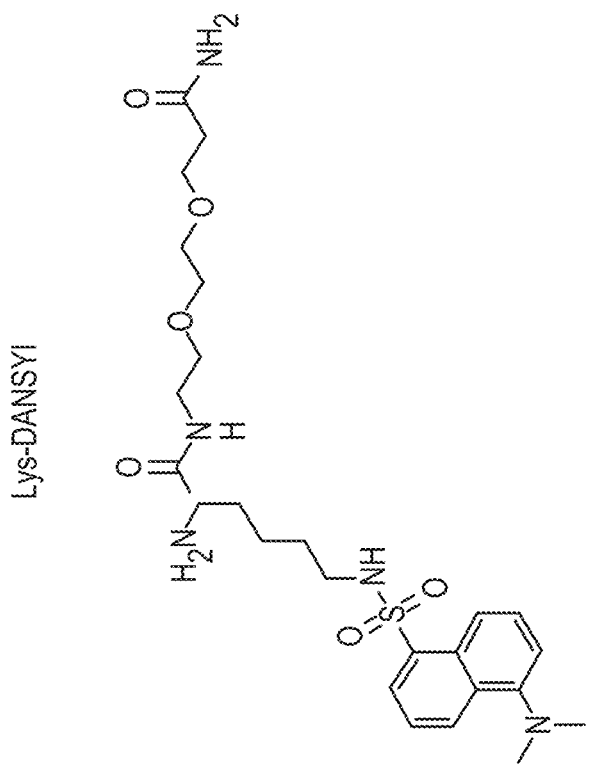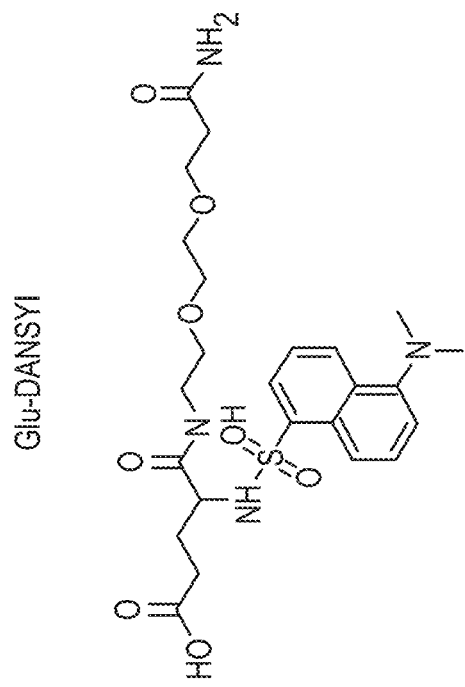
FIG. 29A

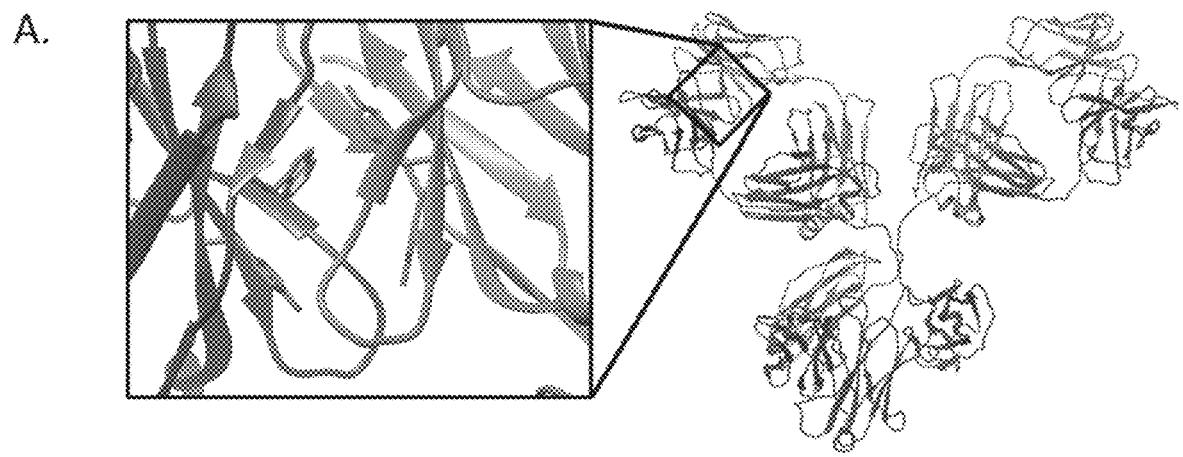
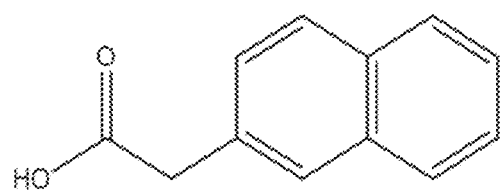
Naphthaleneacetic acid
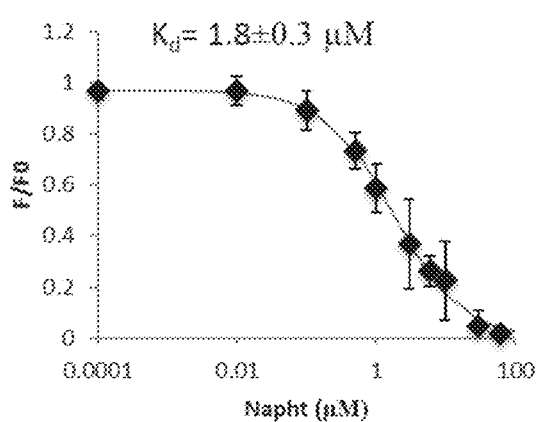
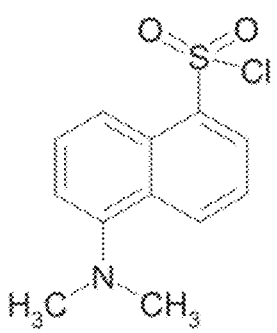
Dansyl
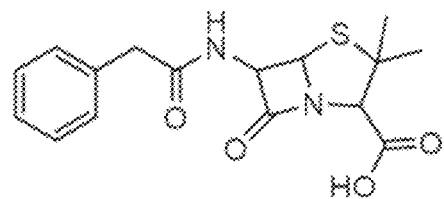
Penicillin G
*FIG. 30A-D*

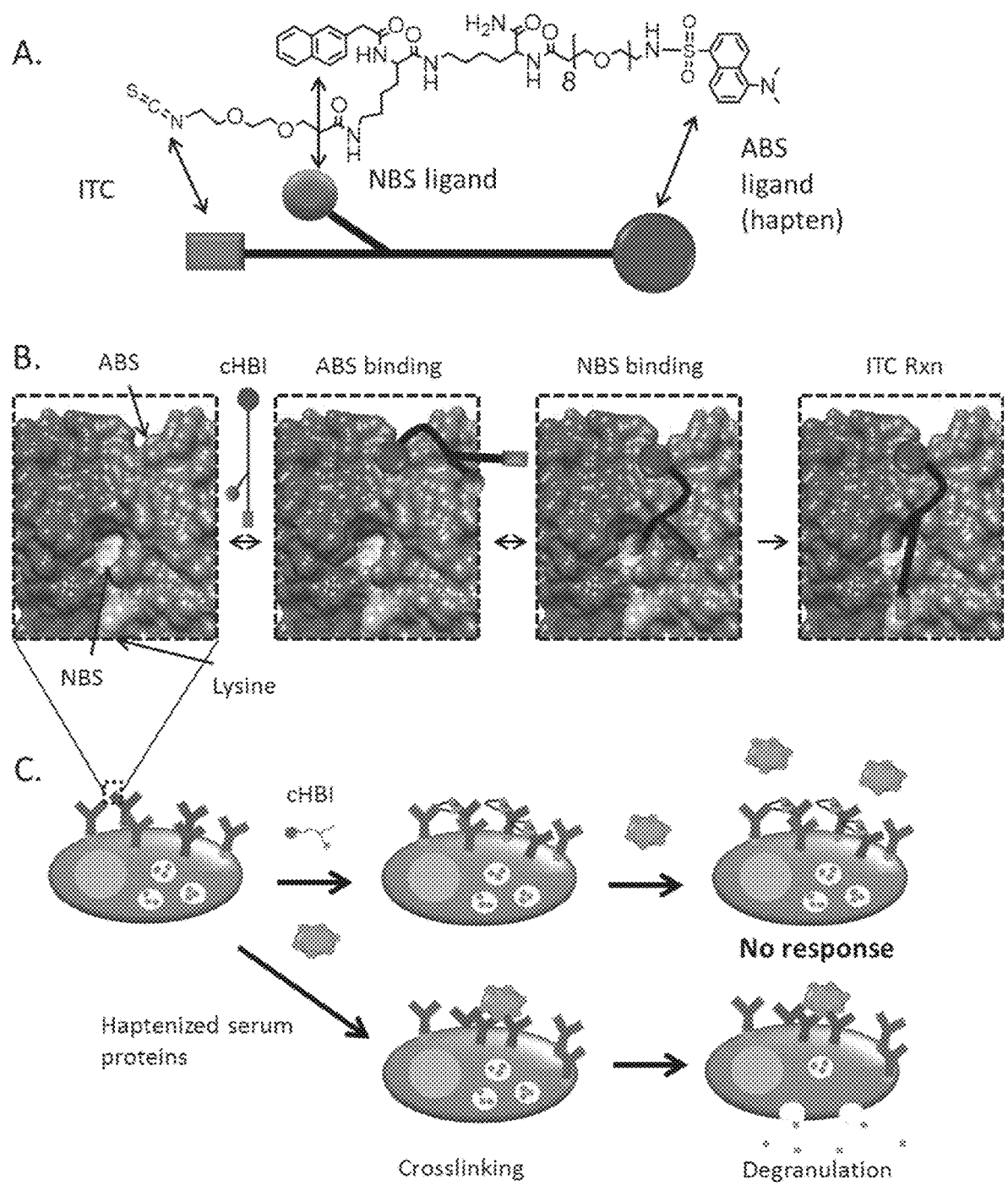
FIG. 31A-C

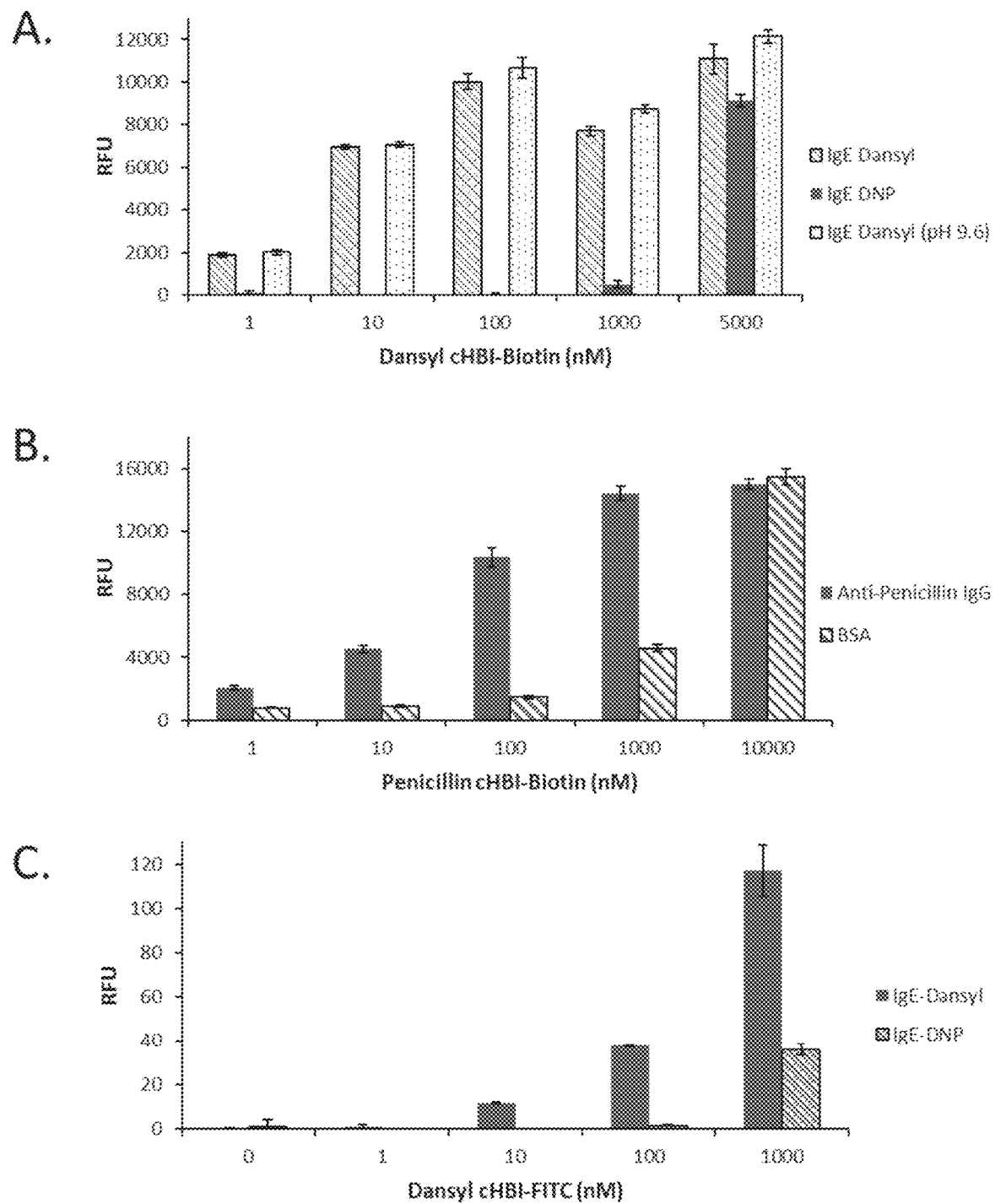
FIG. 32A-C

A.
B.
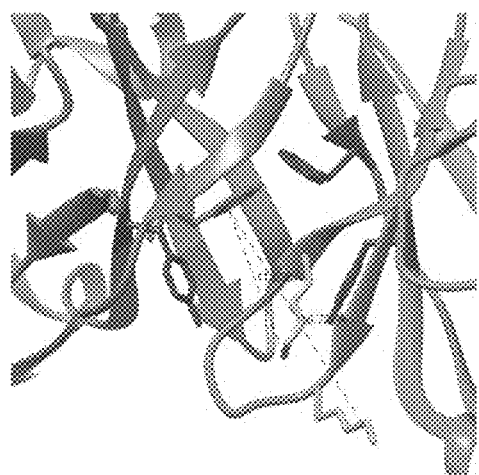
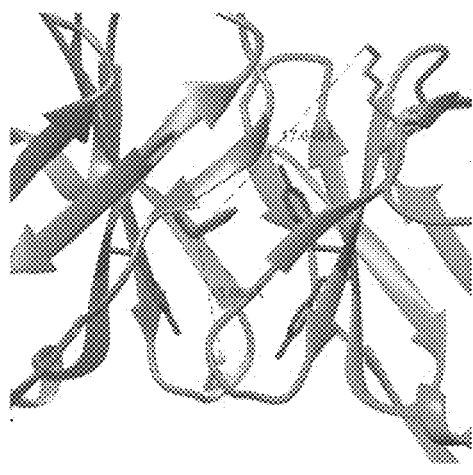
C.
D.
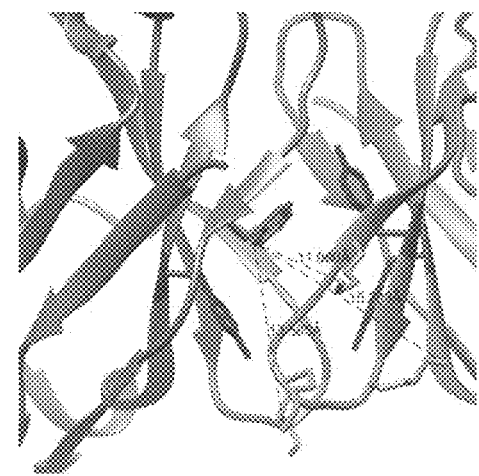
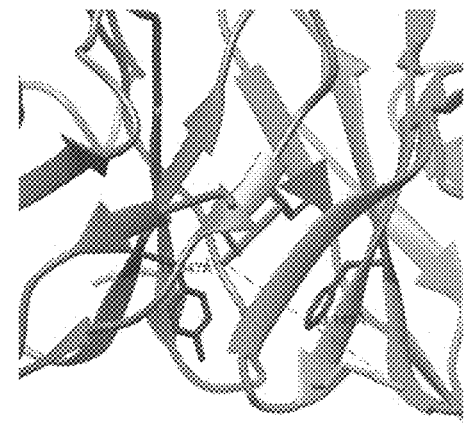
*FIG. 35A-D*

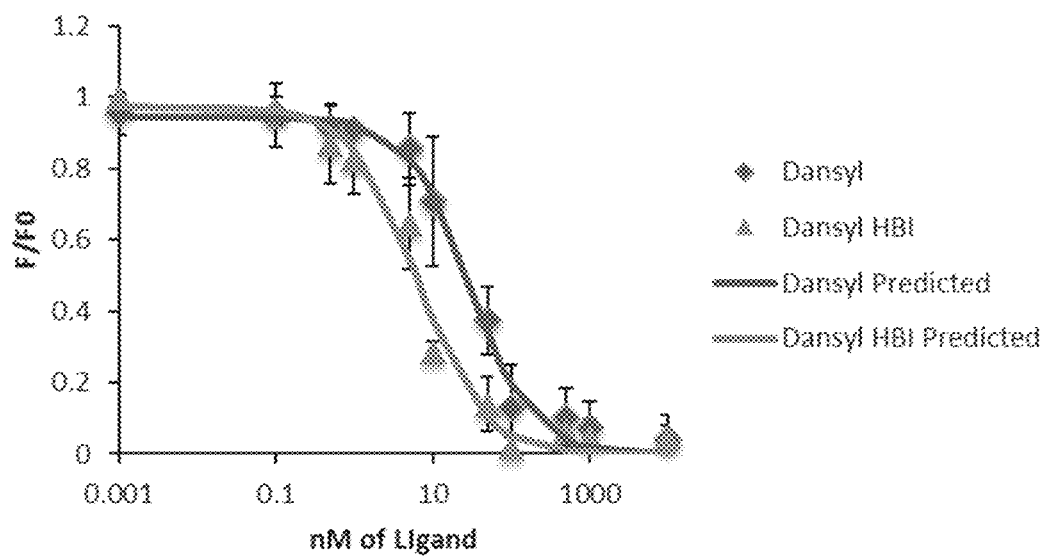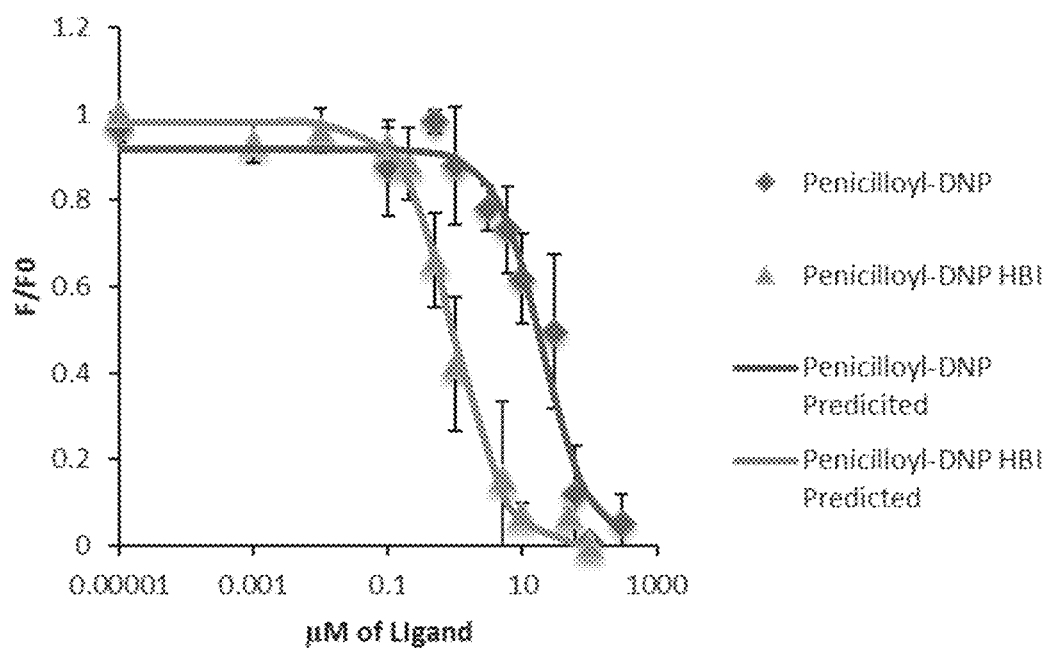
FIG. 36

NANOALLERGENS AND USES THEREOF

RELATED APPLICATIONS

This application is a National Stage filing under 35 U.S.C. § 371 of International Application No. PCT/US2016/053816 filed Sep. 26, 2016, which claims priority under 35 U.S.C. § 119(e) to U.S. Provisional Patent Application No. 62/232,978 filed Sep. 25, 2015, which is applications are hereby incorporated by reference in their entirety.

GOVERNMENT SUPPORT

This invention was made with government support under Grant Nos. R01 AI108884 and R56 AI108884 awarded by the National Institutes of Health. The government has certain rights in the invention.

REFERENCE TO SEQUENCE LISTING

The present application includes a Sequence Listing in electronic format as a text file titled "Seq_Listing.txt" which was created on Feb. 29, 2016 and has a size of 6 kilobytes. The contents of txt file "Seq_Listing.txt" are incorporated by reference herein.

BACKGROUND

The allergic reaction, type I hypersensitivity, is a complex immune reaction to innocuous compounds such as food, environmental factors and drugs. These reactions can trigger symptoms from harmless skin irritation to a life-threatening anaphylaxic reaction and require sophisticated techniques to diagnose and treat. Approximately 1.6% of the U.S. population is at risk for an allergy mediated anaphylaxis response. In the U.S., anaphylaxis reactions account for over three hundred thousand emergency room visits per year. Currently, there are no known FDA approved preventative treatments for type I hypersensitivity. Drugs, such as steroids and antihistamines, treat allergy symptoms, but not the underlying response.

Type I hypersensitivity is characterized by the release of inflammatory cytokines such as histamine from mast cells after exposure to an allergen, also known as a degranulation response. The response is initiated when immunoglobulin constant fragment epsilon receptors (FcεRI) binds the Fc region of an allergen specific IgE, forming the IgE-FcεRI complex. The event is marked by the clustering of the complex on mast cells, inducing an intracellular signaling cascade which causes degranulation. This event, also known as crosslinking, is triggered by several IgEs binding multivalently to a single allergen protein.

One major hurdle for current research, both clinical and at the bench top, is the determination and evaluation of the allergen epitopes, which are regions where IgEs bind to trigger degranulation. Determination and evaluation require binding assays using either genetically modified allergen protein or the use of linear peptide fragments or sequences taken from an allergen protein. However, there have been complexities associated with genetically modifying and expressing allergen proteins and controlling mutagenic sites. Another drawback is that, unlike epitope sequences in folded proteins, linear peptide mimetics of protein epitopes, as allergen mimetics, undergo an increase in conformational entropy. The use of linear peptide mimetics of protein epitopes decreases binding affinity, therefore, any method utilizing this technique could overlook moderate-to-low affinity epitopes that are important or critical for degranulation response.

Another disadvantage is that the binding assays require copious amounts of purified IgE and patient serum. Additionally, they are only capable of measuring monovalent IgE-epitope binding. This form of binding is not representative of degranulation response in vivo. Epitope antigenicity, which is the ability for a molecule to stimulate degranulation response, is not directly correlated with binding affinity. Rather, epitope antigenicity is dependent on multivalent reactions and intercellular regulatory responses. Therefore, there is a need for a method for determining allergen epitope antigenicity that is representative of degranulation response in vivo. Moreover, while various techniques for diagnosing allergy sensitivity exist, none of these techniques alone are suitable for determining the binding sites on allergen proteins. The present disclosure addressed these needs.

SUMMARY

Embodiments herein relate to the field of nanoparticles, and more particularly to liposomal nanoparticles for diagnostic applications. As will be described further hereinbelow, the invention provides an allergen presentation platform. The platform is a liposomal nanoparticle that can have one or more presented above the surface of the nanoparticle that can elicit an allergic reaction, for example, an IgE dependent reaction.

Accordingly, the invention provides a liposomal nanoparticle comprising:

about 0.1 mol % to about 20 mol % of a synmimotope-lipid conjugate;

about 2 mol % to about 10 mol % of a polyethylene glycol-lipid (PEG-lipid) conjugate; and about 80 mol % to about 97 mol % of a phospholipid.

The nanoparticle has a spherical lipid bilayer comprising the phospholipid and the synmimotope-lipid conjugate, the spherical lipid bilayer having an interior surface and an exterior surface; the exterior surface of the spherical lipid bilayer comprises the PEG-lipid conjugate wherein PEG moieties of the PEG-lipid conjugate form a coating over the exterior surface of the nanoparticle, and one or more synmimotope moieties of synmimotope-lipid conjugates protrude above the coating formed by the PEG moieties.

The synmimotope-lipid conjugate comprises a conjugate of Formula I:

$$A\text{-}B\text{-}C\text{-}D\text{-}E\text{-}(F)n \quad (I)$$

wherein

A is a synmimotope, wherein the synmimotope is a mimotope, a hapten, or a peptide sequence of known or suspected allergen epitopes;

B is a first linker or a direct bond, wherein the first linker, when present, comprises one or more ethylene glycol moieties or saccharide moieties covalently attached to synmimotope (A) and second linker (C) by amide bonds;

C is a second linker, wherein the second linker (C) comprises an amino acid or an oligomer of a charged amino acid or a polar amino acid, wherein the amino acid or oligomer is covalently attached by amide bonds to first linker (B) or the synmimotope (A) if first linker (B) is a direct bond, and to third linker (D);

D is a third linker, wherein the third linker (D) comprises an oligomer of ethylene glycol attached covalently at distal ends by amide bonds to second linker (C), and tag (E);

E is a tag, wherein the tag comprises a monomer or dimer of an amino acid, optionally further comprising a chromophore or fluorophore (e.g., tryptophan);

F is a ($C_8$-$C_{22}$)acyl moiety, such as a palimitoyal moiety, covalently attached to tag (E) by an amide bond; and n is 1 or 2;

wherein the diameter of the nanoparticle is about 20 nm to about 2 μm. See, for example, the lipid conjugates of FIGS. 1A, 1B, 7, 18A, 23, and 31A.

In one embodiment, the synmimotope (A) of the synmimotope-lipid conjugate is a known or suspected allergen epitope selected from the group of allergen epitopes consisting of SEQ ID NO: 1-4; SEQ ID NO: 5-12; SEQ ID NO: 13-16; SEQ ID NO: 17-23; and SEQ ID NO: 24-31.

In another embodiment, the synmimotope (A) of the synmimotope-lipid conjugate is a hapten. The hapten can be any small molecules that elicit an immune response, that can be conjugated to form the lipid conjugate of Formula I. Conjugation chemistry is well known in the art (see Hermanson, *Bioconjugate Techniques*, Academic Press, San Diego, Calif. (1996)). In various embodiments, the hapten can be selected from the group consisting of 2,4-dinitrophenol (DNP), dansyl, penicillin, a sulfa drug (e.g., celecoxib, sulfasalazine, prontosil, sulfamethoxazole, sulfasalazine, sulfadiazine, and the anti-retrovirals amprenavir, or fosamprenavir), and a platinum drug (e.g., cisplatin or oxalaplatin).

In one embodiment, the PEG-lipid conjugate comprises about 10 to about 200 ethylene glycol residues and the lipid is a ($C_8$-$C_{22}$)acyl moiety or a phospholipid, wherein the ethylene glycol residues and the lipid are optionally linked by an amide bond.

In some embodiments, the phospholipid comprises one or two ($C_8$-$C_{22}$)acyl moieties. In a specific embodiment, the phospholipid is 1,2-distearoyl-sn-glycero-3-phosphocholine (DSPC) or 1,2-dipalmitoyl-sn-glycero-3-phosphocholine (DPPC).

In one embodiment, second linker (C) comprises a charged amino acid. The charged amino acid can be, for example, aspartic acid, glutamic acid, lysine, or and arginine. In another embodiment, second linker (C) comprises a polar amino acid. The polar amino acid can be, for example, glutamine, asparagine, histidine, serine, threonine, or methionine.

In one embodiment, the tag (E) is a tryptophan residue, or a monomer or dimer of lysine. In various embodiments, moiety (F) is a ($C_{16}$)acyl moiety or a ($C_{18}$)acyl moiety.

In some specific embodiments, the nanoparticle has a diameter of about 10 nm to about 300 nm. In other specific embodiments, the nanoparticle can have a diameter of about 80 nm to about 220 nm, or about 100 nm to about 160 nm.

In one embodiment, the nanoparticle has a plurality of mimotopes, e.g., epitopes, protruding above the coating formed by the PEG moieties, wherein the plurality of epitopes is homogeneous or heterogeneous.

In one embodiment, the nanoparticle comprises: about 2 mol % mimotope-lipid conjugate; about 5 mol % PEG-lipid conjugate; and about 93 mol % 1,2-distearoyl-sn-glycero-3-phosphocholine (DSPC).

In various embodiments, the nanoparticle can further comprise about 1 mol % to about 35 mol % cholesterol, with respect to the molar amount of the phospholipid.

In another embodiment, the nanoparticle comprises: about 2% mimotope-lipid conjugate; about 5% polyethylene glycol-lipid (PEG-lipid) conjugate; about 93% 1,2-distearoyl-sn-glycero-3-phosphocholine (DSPC); wherein the mimotope-lipid conjugate comprises: a mimotope; an ethylene glycol linker; an oligo-lysine linker; a tryptophan residue; and a palmitoyl tail;

wherein the mimotope is a known or suspected allergen epitope selected from the group of allergen epitopes consisting of SEQ ID NO: 1-4, SEQ ID NO: 5-12, SEQ ID NO: 13-16, SEQ ID NO: 17-23, and SEQ ID NO: 24-31;

wherein said PEG-lipid conjugate comprises PEG conjugated to a hydrophilic region of a lipid, wherein said lipid comprises a hydrophilic region and a hydrocarbon tail; and wherein the diameter of the nanoparticle is about 20 nm to about 300 nm.

The invention further provides a method of diagnosing an allergy comprising:

providing sera from an allergy sensitive subject; contacting said sera to cells in culture; adding a nanoparticle that contains a synmimotope as described herein; and evaluating degranulation results; thereby determining if an allergy is present in the subject.

The evaluation of degranulation results of the nanoparticle can be by a standard beta hexosaminidase assay. The nanoparticle can include a mimotope of any one of SEQ ID NO: 1-31. In various embodiments, the mimotope is selected from the (e.g., five membered) group consisting of SEQ ID NO: 1-4, SEQ ID NO: 5-12, SEQ ID NO: 13-16, SEQ ID NO: 17-23, and SEQ ID NO: 24-31. A plurality of the nanoparticles can be added to the sera and cells in culture. The nanoparticle can be used for identifying a specific subject's sensitivity to a particular set of epitopes. The nanoparticle can be used for predicting a symptomatic clinical response. Furthermore, the nanoparticle can be used to evaluate epitopes alone or in combination to determine the ability to trigger allergic responses.

The invention also provides a method of diagnosing an allergy comprising: providing blood containing basophils; adding a nanoparticle that contains a synmimotope as described herein to the blood; and evaluating degranulation results; thereby diagnosing the presence or character of an allergy. The evaluation of degranulation results of the nanoparticle can be, for example, by fluorescence-activated cell sorting (FACS) to identify activated basophils.

The invention further provides a method of diagnosing an allergy comprising: providing a nanoparticle that contains a synmimotope as described herein; contacting the nanoparticle to a subject's skin; delivering the nanoparticle to said subject subcutaneously; and evaluating immunological response; thereby diagnosing the presence or character of an allergy. The nanoparticle can be contacted to subject's skin using a scratch test. The nanoparticle can be contacted to subject's skin using a microneedle. The microneedle can include a plurality of nanoparticles. The nanoparticles can comprise a spatial array of a plurality of mimotopes selected from the group consisting of SEQ ID NO: 1-4, SEQ ID NO: 5-12, SEQ ID NO: 13-16, SEQ ID NO: 17-23, and SEQ ID NO: 24-31. The microneedle can comprise at least one mimotope for an allergen of interest.

A further method for using the nanoparticle thus includes, but is not limited to, providing sera from an allergy sensitive individual for an in vitro application. IgE molecules in sera can be allowed to bind to receptors on cell surface. Degranulation using nanoallergens can be monitored using, for example, a standard beta hexosaminidase assay. The nanoparticle can include a plurality of nanoparticles with single or different combinations of mimotope-lipid conjugates loaded to trigger allergic responses. The nanoparticle can be used to identify a specific patient's sensitivity to a set of epitopes and predict a symptomatic clinical response. An in vivo application of using nanoallergen includes animal testing of allergen molecules and immunological responses. Another in vivo application includes using nanoallergens in a clinical application similar to a scratch test.

BRIEF DESCRIPTION OF THE DRAWINGS

The following drawings form part of the specification and are included to further demonstrate embodiments or various aspects of the present disclosure. In some instances, embodiments of the disclosure can be best understood by referring to the accompanying drawings in combination with the detailed description presented herein. The description and accompanying drawings may highlight a certain specific example, or a certain aspect of the disclosure. However, one skilled in the art will understand that portions of the example or aspect may be used in combination with other examples or aspects of the invention.

FIG. 28A-C. Schematic demonstrating the divalent avidity enhancement on a single IgE. When the hapten molecules are spaced too far apart, divalent interactions on the same IgE molecule are less likely during a shorter timescale (t<20 mins) as seen in A. Likewise, divalent interactions are not likely when the haptens are heterologous (B). Rapid, divalent interactions that would likely improve the degranulation response can occur on the same IgE with the proper hapten spacing under 10 nm as seen in C.

FIG. 29A-C. Dansyl amino acid conjugates. Two different amino acids were conjugated to dansyl using Fmoc solid phase peptide synthesis. Their structures are shown in A and their molecular weights were confirmed with high resolution mass spectroscopy (B). A fluorescence quenching titration was then performed with the compounds and IgE$^{dansyl}$ and a disassociation constant ($K_d$) was calculated (C).

FIG. 30A-D. A crystal structure of a mouse IgG (PDB: 1IGY) demonstrating the location of the NBS between the heavy chain (in blue) and light chain (in red) shown in A. Tryptophan residue is colored green while tryosines are labeled purple. Naphthaleneacetic acid, a NBS ligand used in this study, is given in B. A fluorescence quenching experiment demonstrated binding between a DNP labeled naphthalene molecule and IgE$^{dansyl}$ is shown in C. The chemical structures of the haptens (dansyl and Benzyl Penicillin) are shown in D.

FIG. 31A-C. Schematic of cHBI molecule with cartoon seen in (A). Crystal structure of typical antibody binding pocket with cartoon depicting cHBI covalent binding in (B). Cartoon demonstrating cHBI degranulation inhibition shown in (C).

FIG. 32A-C. cHBI molecules bind allergy relevant antibodies. the Dansyl cHBI binds IgE$^{dansyl}$ in a concentration dependent fashion when incubated for 5 hrs at 37° C. at pH 7.4 and 9.6 (A). Penicillin cHBI's selectively bind an anti-penicillin IgG when incubated for 5 hours at 37° C. and not a BSA control (B). Flow cytometry indicates that dansyl cHBI's bind IgEs bound to FcεRI on the surface of RBL-2H3 cells (C).

FIG. 35A-D. NBS sites of various antibodies with highlighted lysines. In orange. Rituximab (A), Cetuximab (B), Trastuzumab (C), Anti-DNP IgE SPE-7 (D). The light chain is shown in purple and the heavy chain in green.

FIG. 36. Fluorescence quenching binding results for dansyl and penicilloyl HBI's. IgE$^{dansyl}$ was used in the top graph and IgE$^{Penicillin}$ was used in the bottom graph.

DETAILED DESCRIPTION

Figure 1A:
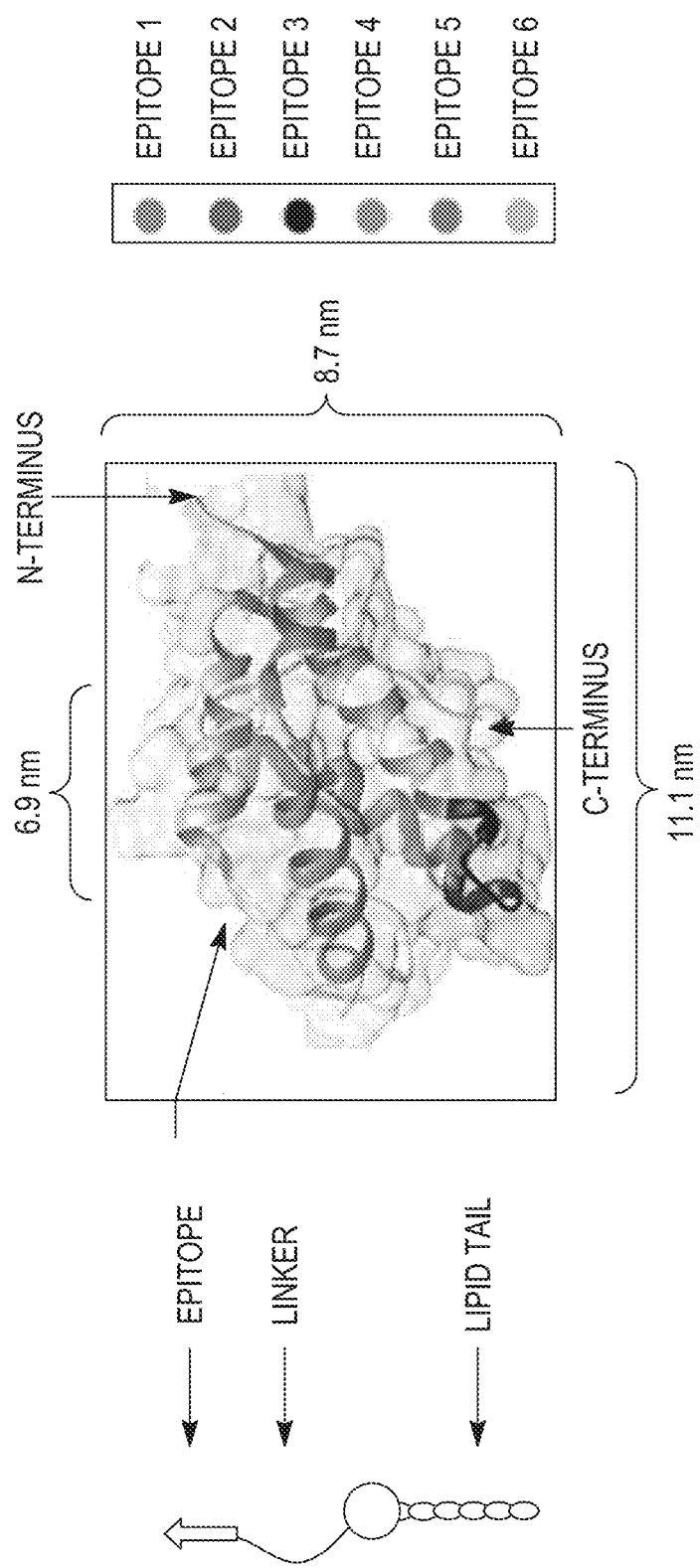
FIGS. 1A-1B. Nanoallergen design. (A). Schematic of epitope-lipid conjugate. (B). Composition of the nanoallergen, according to an embodiment.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Thus, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous. The use of the word "a" or "an" when used in conjunction with the term "comprising" in the claims and/or the specification may mean "one," but it is also consistent with the meaning of "one or more," "at least one," and "one or more than one." Some embodiments of the present disclosure may consist of or consist essentially of one or more elements, method steps, and/or methods of the invention. It is contemplated that any method or composition described herein can be implemented with respect to any other method or composition described herein.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

In various embodiments, methods, apparatuses, and systems for nanoallergens are provided. In exemplary embodiments, a computing system may be employed to perform, or to control devices employed to perform, one or more methods as disclosed herein.

The term "contact", as used herein, refers to an addition to or an interaction between, at least, two molecules, that causes an increase or decrease in the magnitude of a certain activity or function of the molecules compared to the magnitude of the activity or function observed in the absence of, at least, one of the molecules. Example includes, but is not limited to, contact of sera to cells in culture.

As used herein, "subject" refers to a person, an individual, or animal that is the object of medical or scientific study or a patient. In another aspect, the present disclosure provides a composition of matter and method of administrating said composition of matter to a subject, preferably a human, or in a format that can be diluted or reconstituted for administration to the subject.

The term "immunoglobulin E" (hereinafter, used interchangeably with "IgE")," as used herein, collectively means proteins that participate in the body's protective immunity by selectively acting against antigens. Immunoglobulins are composed of two identical light chains and two identical heavy chains. The light and heavy chains comprise variable and constant regions. There are five distinct types of heavy chains based on differences in the amino acid sequences of their constant regions: gamma (γ), mu (μ), alpha (a), delta (δ) and epsilon (ε) types, and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., Fundamental Immunology, 2nd Ed., 1989, 55-73). According to the features of the constant regions of the heavy chains, immunoglobulins are classified into five isotypes: IgG, IgA, IgD, IgE and IgM.

As used herein, an "epitope," "epitope protein," "epitope peptide," "allergen epitope," "allergenic protein" or "allergy protein" is a mimotope, peptide, cyclic peptide, peptidomimetic, or other molecule that binds to IgE to trigger degranulation and any polypeptide determinant capable of specific binding to an immunoglobulin or T-cell receptor. In certain embodiments, epitope determinants include chemically active surface groupings of molecules such as amino acids, sugar side chains or moieties, phosphoryl, or sulfonyl moieties, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. Examples include, but are not limited to, peanut allergen proteins such as Ara h1, Ara h2, Ara h6 and shrimp allergen protein, Pen a1 or any known or suspected allergen.

As used herein, a "mimotope" is a macromolecule or peptide that mimics the structure of an "epitope". A mimotope can be a known or suspected peptide sequence of allergen epitopes. Examples include, but are not limited to, peptide sequences of allergen epitopes such as Ara h1, Ara h2, Ara h6 and, Pen a1, or any known or suspected peptide sequence of allergen epitopes, such as one or more of the sequences described herein.

As used herein, a "synmimotope" is a mimotope, an epitope, a hapten, a peptidomimetic, or an allergen metabolite (e.g., a metabolite of penicillin). Therefore, a synmimotope includes mimitopes, which are macromolecules or peptides that mimic the structure of an epitope, as well as small molecules (e.g., sulfa drugs or chemotherapeutics), allergen metabolites, and actual epitopes that can elicit an immune response. Haptens are small molecules that elicit an immune response only when attached to a large carrier such as a protein or a lipid of the lipid conjugates described herein. Thus, a "synmimotope-lipid conjugate" is a mimotope, an epitope, a hapten, a peptidomimetic, or an allergen metabolite conjugated to a carrier such as a lipid described herein.

As used herein, a "first linker" can be a sugar, an oligosaccharide, an amino acid, peptides, or other molecules that can provide favorable results in epitope display and binding. Examples of a first linker include, but are not limited to, ethylene glycol molecules.

As used herein, a "second linker" can be any moiety that will improve mimotope-lipid water solubility profile. The second linker increases hydrophilicity and improves epitope display on the liposomal surface. Examples include, but are not limited to, charged amino acids such as aspartic acid (D), glutamic acid (E), lysine (K) and arginine (R) or polar amino acids, such as, glutamine (Q), asparagine (N), histidine (H), serine (S), threonine (T), and methionine (M).

As used herein, a "fluorophore residue", "fluorophore" or "chromophore" can be any moiety that can aid in purification of the epitope-lipid conjugate. An example of a fluorophore includes, but is not limited to, tryptophan.

As used herein, a "lipid" or "bulk lipid" is any compatible lipid that has a hydrophilic region and a hydrocarbon tail that can facilitate the incorporation of epitope-lipid conjugate into a lipid membrane. Examples include, but are not limited to, phospholipids, such as 1,2-distearoyl-sn-glycero-3-phosphocholine (DSPC), and fatty acids, such as palmitic acid.

As used herein, "nanoparticle" refers to any partially or wholly lipid-coated nanostructure having a cross-section length ("diameter") in the range of 1 to 3000 nanometers (nm) (i.e., 1 nm to 3 microns). As used herein, cross-section length refers to the measurement of the longest cross-section length of the nanoparticle (e.g., the longest distance that can be measured between two points of a cross-section of the nanoparticle). In some instances, such particles will have a cross-section length in the range of 10 nm to 50 nm, 50 to 1000 nm, 50 to 900 nm, 50 to 800 nm, 50 to 700 nm, 50 to 600 nm, 50 to 500 nm, 50 to 400 nm, 50 to 300 nm, 50 to 200 nanometers, and/or 50 to 100 nm. The lower end of these ranges may alternatively be about 100 nm. In some instances, the particles will have a cross-section length of greater than 1 micron. The size of the nanoparticle is therefore predetermined and controlled as is the size of its nanostructure core.

Figure 1B:
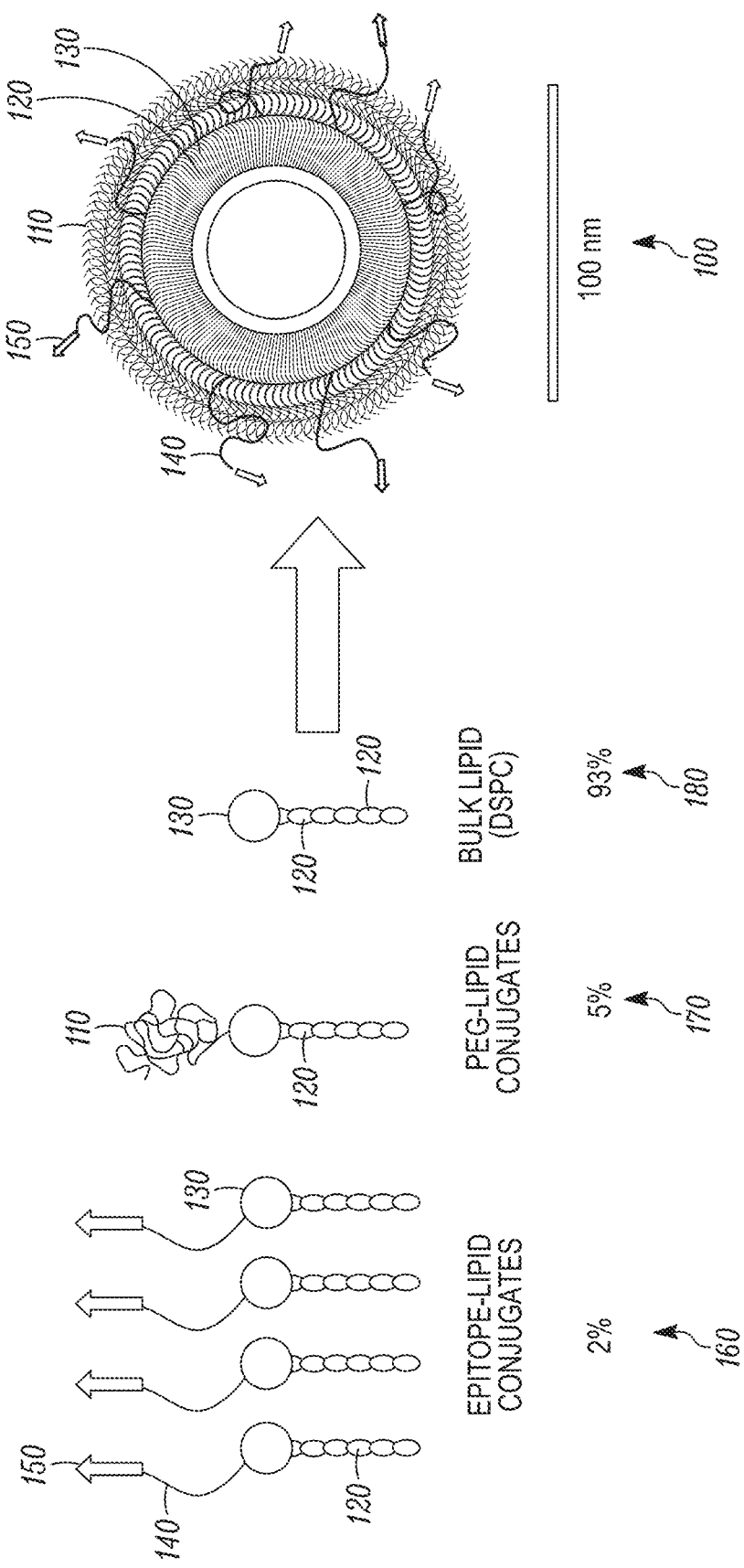

FIG. 1B illustrates an embodiment of a nanoparticle 100 engineered to display allergen epitope peptides on the surface in a multivalent fashion called nanoallergen 100, in accordance with various embodiments. A nanoallergen can be designed for use in in vitro and in vivo applications. Nanoallergens 100 can be used to identify allergen epitopes through blind screening of peptide sequences from allergen proteins, evaluate epitopes alone and in combination in their ability to trigger allergic responses, and to identify a specific subject's sensitivity to a set of epitopes and predict a clinical response (a symptomatic response). This information would be valuable in future inhibitor design and allow for a personalized inhibitor cocktail to be formulated based upon the subject's epitope reactivity. As illustrated in FIG. 1B, nanoallergen 100 can have a hydrocarbon interior portion 120 surrounded by an outer portion that includes a hydrophilic region 130, water-soluble polymers 110 (e.g., PEG), epitope-lipid conjugate 160, and a first linker 140. Epitope-lipid conjugate 160 includes an epitope of a known or suspected allergen protein 150, and a first linker 140. Nanoallergen 100 can include at least two groups of component molecules, which are shown in FIG. 1B as components 160 and 180.

As used herein, the term "component" can refer to one molecule of a particular species, for example, one molecule of component 160, or to a plurality of molecules of a particular species (eg. two or more molecules of component 160). Nanoparticle may include components 110, 120, 130, 140, 150, 160, 170, 180 and/or combinations thereof in various ratio. As used herein, a "molecular ratio" may be provided to indicate the number of molecules of two or more components (e.g., 160, 170, 180) in a nanoparticle. The number of molecules of a component in a nanoparticle may also be described in terms of a "mole percentage," which is calculated by dividing the number of molecules of that component by the number of molecules in the nanoparticle. For example, in a nanoparticle with 100 component molecules, 93 of which are component 180, 5 of which are component 170, 2 of which are component 160, the "molecular ratio" of the components (160:170:180) is 93:5:2, and the mole percentages of the three components are 93%, 5% and 2%, respectively. If not specifically identified, percentages referenced herein are molar percentages (mol %), unless the context specifically indicates otherwise.

Referring now to FIG. 1B, components 160 and 170 can include a lipid molecule 120, 130, 180 coupled directly or indirectly to one or more additional molecules. Typically, lipid molecules 120, 130, 180 are amphipathic lipid molecules, each with a polar/hydrophilic region 130 a nonpolar/hydrophobic/hydrocarbon tail 120. Optionally, some or all of the lipid molecules can be phospholipids or fatty acids or compatible lipids that can facilitate the components incorporation into a lipid membrane.

Optionally, component 170 can be made to enhance the stability and/or circulation time of nanoparticle 100. In some embodiments, component 170 may include a polymer 110 conjugated or otherwise coupled to lipid molecule 180 to form 170. Polymer 110 can be a water-soluble polymer, such as polyethylene glycol (PEG). In some other embodiments, polymer 110 can be coupled to lipid molecules 180 to form a PEG-lipid block polymer 170 (e.g., PEG2000-DSPE conjugate or PEG-lipid conjugate). Optionally, Nanoallergens 100 can include cholesterol to improve particle stability.

PEGylated nanoparticles provide a combination of high circulation times, increased stability, and a defined size range of 1-5 nm, 1-10 nm, 1-50 nm, 1-100 nm, 1-200 nm or 1-300 nm. In some embodiments, nanoparticles ranging from 50 nm to 200 nm in size can be used in cellular experiments. In other embodiments, nanoparticles can be synthesized from a couple 10s of nanometers to several 10s or 100s of micrometers, for example, in animal or human testing. An important characteristic of nanoparticles is that they present particularly attractive scaffolds for multivalent display of allergen epitope peptides and other multiple functional groups on their surfaces. In some embodiments, nanoallergen may include, but are not limited to gold, silicon, dedramer, or any molecule that provides multivalent display other than a liposome.

Prior to liposome formation, desired epitopes 150 are covalently conjugated to lipid tails 120 with a linker 140 and the product, epitope-lipid 160, is purified. The lipid tails 120 provide the moiety that seamlessly integrates into the liposomal membrane and anchors the epitope 150 to the liposomal particle surface permanently. Following the synthesis and the purification the epitope-lipid 160 can then be incorporated into nanoallergens 100 during liposomal nanoparticle synthesis at the desired precise ratios to form nanoallergens 100.

By displaying multiple copies of the epitope on the liposome surface, nanoallergens provide a highly multivalent vehicle to assess the epitope's immunogenicity and not merely its monovalent IgE binding affinity. The nanoallergen platform is extremely versatile and can have varying particle sizes and epitope loading. Most importantly, nanoallergens can display multiple epitopes on a single particle, allowing multivalent binding to IgEs specific to a variety of epitopes, simulating allergen proteins. Through systematic removal of individual epitopes from a heterogeneous nanoallergen, the most crucial epitopes for an allergen protein's immunogenicity can be evaluated through either in vitro or potentially in vivo experiments. Such precise control over epitope ratios can also be utilized to study the more nuanced biological interactions in mast cell degranulation as well.

The epitope-lipid conjugates that are displayed on nanoallergens are synthesized and purified before liposome formation. The design of the epitope-lipid conjugate consists of five components. The components include a mimotope, a first linker (such as oligo-lysine linker) to increase hydrophilicity and to improve epitope display on the liposomal surface, a second linker, such as, but is not limited to ethylene glycol linker to further aid epitope display, a chromophore or fluorophore (such as, but not limited to, tryptophan) to aid purification and a lipid (such as, but not limited to, palmitic acid tail) to facilitate the component's incorporation into a lipid membrane. These five components can be chemically linked together using Fmoc Solid Phase Peptide Synthesis (SPPS), cleaved from the resin and purified using reverse phase high performance liquid chromatography (RP-HPLC). Nevertheless, there are many other potential synthetic methods that can be used to achieve the desired products including but are not limited to in solution synthetic methods and other solid phase synthesis methodologies. The epitopes are typically linear peptide sequences, but could be cyclic peptides and/or mimotopes of the epitope sequences, taken from either current literature or from the peptide sequence of a given allergen protein and then synthesized using SPPS methods.

Embodiments of the Invention

Embodiments of the present disclosure provide a nanoparticle based platform, named nanoallergens for identifying, evaluating and studying allergen epitopes as multiple copies of a single epitope, as well as, in various combinations at any desired ratio against each other on the same particle. Nanoallergens can display multiple epitopes on a single particle, allowing multivalent binding to IgEs specific to a variety of epitopes, simulating allergen proteins. The disclosed nanoallergen platform is extremely versatile and can have varying particle sizes and epitope loading. Nanoparticles can be composed to include various molecular ratios of components. The molar/molecular ratios of nanoparticle components may vary for various embodiments. In some embodiments, a nanoparticle includes 0.1-40% mimotope conjugated to lipid molecule (mimotope-lipid conjugate). The nanoparticle may further include about 85-94.9% lipid, such as, but is not limited to, DSPC (1,2-distearoyl-sn-glycero-3-phosphocholine). The mimotope-lipid conjugate further includes a mimotope, a first linker, and lipid molecule. The mimotope can be a known or suspected allergenic epitope, such as, but is not limited to, Ara h 1, Ara h 2, Ara h 6 and Pen a1. The lipid can have a hydrophobic region and hydrocarbon tail.

In some embodiments, the first linker can be, but is not limited to, a carbohydrate or sugar, such as an oligosaccharide, ethylene glycol, an amino acid, or peptide, to aid in peptide display. In another embodiment, nanoparticle includes a second linker, such as charged or polar amino acid.

In some embodiments, a nanoparticle includes a polymer conjugated to a hydrophobic region of lipid molecule. The polymer can be water-soluble polymer, such as polyethylene glycol (PEG). The polymer can be conjugated to hydrophobic region of lipid molecule to form 5% lipid-PEG block polymer, such as DSPE-PEG2000. In other embodiments, polymers can be poly(lactic-co-glycolic acid) (PLGA), polymeric sugars (e.g., oligosaccharides) or other biocompatible water-soluble molecules.

In some embodiments, a nanoparticle can include a molecule that can improve stability of the nanoparticle, such as, but is not limited to 0.1-35% cholesterol.

In some embodiments, the mimotope-lipid conjugate can be synthesized by using single amino acids. The amino acids can be separated from the rest of the mimotope-lipid conjugate with a first linker. Thereafter, using fluorenylmethyloxycarbonyl(Fmoc)-LysButyloxycarbonyl(Boc)-OH, a second linker is added. A variable length of the first linker is added using an Fmoc protected first linker molecule. Fmoc-Lys(Boc)-OH is added followed by addition of lipid tails. Mimotope-lipid conjugate molecules protected with terminal acid groups can be activated with HBTU and a four-fold molar excess of DIEA for 5 minutes and conjugated to resin over 30 minutes. Thereafter, Fmoc is deprotected with 20% piperidine in DMF and IvDdE is deprotected using 2% hydrazine in DMF. The mimotope-lipid conjugate is cleaved using a 95:2.5:2.5 TFA:water:TIS solution for 45 minutes. The mimotope-lipid conjugate is purified using 1200 Agilent RP-HPLC using a semi-preparative Zorbax C3 column with a two phase water and 70:20:10 IPA:ACN:water mix with a gradient of 60-100% IPA mix over 10 minutes at a flow rate of 3 mL/min. Nevertheless, there are many other potential synthetic methods than can be used to achieve the desired products including, but are not limited to, in solution synthetic methods and other solid-phase synthesis methodologies.

An epitope can be, but is not limited to, linear peptide sequences, cyclic or mimotopes of the epitope sequences taken from either current literature or from the peptide sequence of a given allergen protein and synthesized using solid-phase peptide synthesis (SPPS) methods.

Examples

In the examples below, nanoallergens are used to systematically evaluate which epitopes are crucial in degranulation responses with an in vitro technique. The efficacy of the technique is demonstrated with the major peanut allergen proteins, Ara h 2 and Ara h6. The nanoallergens serve a multivalent platform for studying and evaluating the potency of peanut allergy epitopes.

Materials.

NovaPEG Rink Amide resin, HBTU [2-(1H-benzotriazol-1-yl)-1,1,3,3 tetramethyluroniumhexafluorophosphate], all Fmoc conjugated amino acids and BSA (Bovine Serum Albumin) were purchased from EMD Biosciences. DIEA (N,N-diisopropylethylamine), TFA (trifluoroacetic acid), triisopropylsilane (TIS), hydrazine, cholesterol, dichloromethane, 2-proponol, ACN (acetonitrile), ethanol, all Kaiser test reagents, G418 salt and Bovine serum albumin (BSA), tween 20 and piperidine were purchased from Sigma. DMF (dimethylformamide) (>99.8%), chloroform, penicillin, L-glutamine and Eagle's Minimum Essential Media were obtained from Thermo Fisher. 1,2-Distearoyl-sn-glycero-3-phosphocholine (DSPC), DSPE-mPEG2000 (1,2-distearoyl-sn-glycero-3-phosphoethanolamine-N-methoxy(polyethylene glycol)-2000] (ammonium salt)), membranes and all mini extruder components were purchased from Avanti Polar Lipids (Alabaster, Ala., USA). Fmoc-EG6-OH was purchased from Quanta Biodesign. DiD fluorescent dye (3H-Indolium, 2-(5-(1,3-dihydro-3,3-dimethyl-1-octadecyl-2H-indol-2-ylidene)-1,3-pentadienyl)-3,3-dimethyl-1-octadecyl-, perchlorate) and fluorescein 5(6) isothiocyanate was purchased from Invitrogen. Western blot reagents, gels and equipment were obtained from Bio-Rad. Goat anti-rabbit IgG (ab6721), anti BTK IgG (ab50659) and anti-BTK (phospho Y223 IgG (ab68217) and anti-human IgE were obtained from Abcam. RIPA buffer and phosphatase inhibitor I was purchased from Boston Bioproducts (Boston). Anti-rabbit-HRP IgG was purchased from Jackson ImmunoResearch. Human serum samples were purchased from PlasmaLab International (Everett, Wash.).

Example 1. Synthesis and Purification of Lipid-Hapten Conjugates

Figure 7:
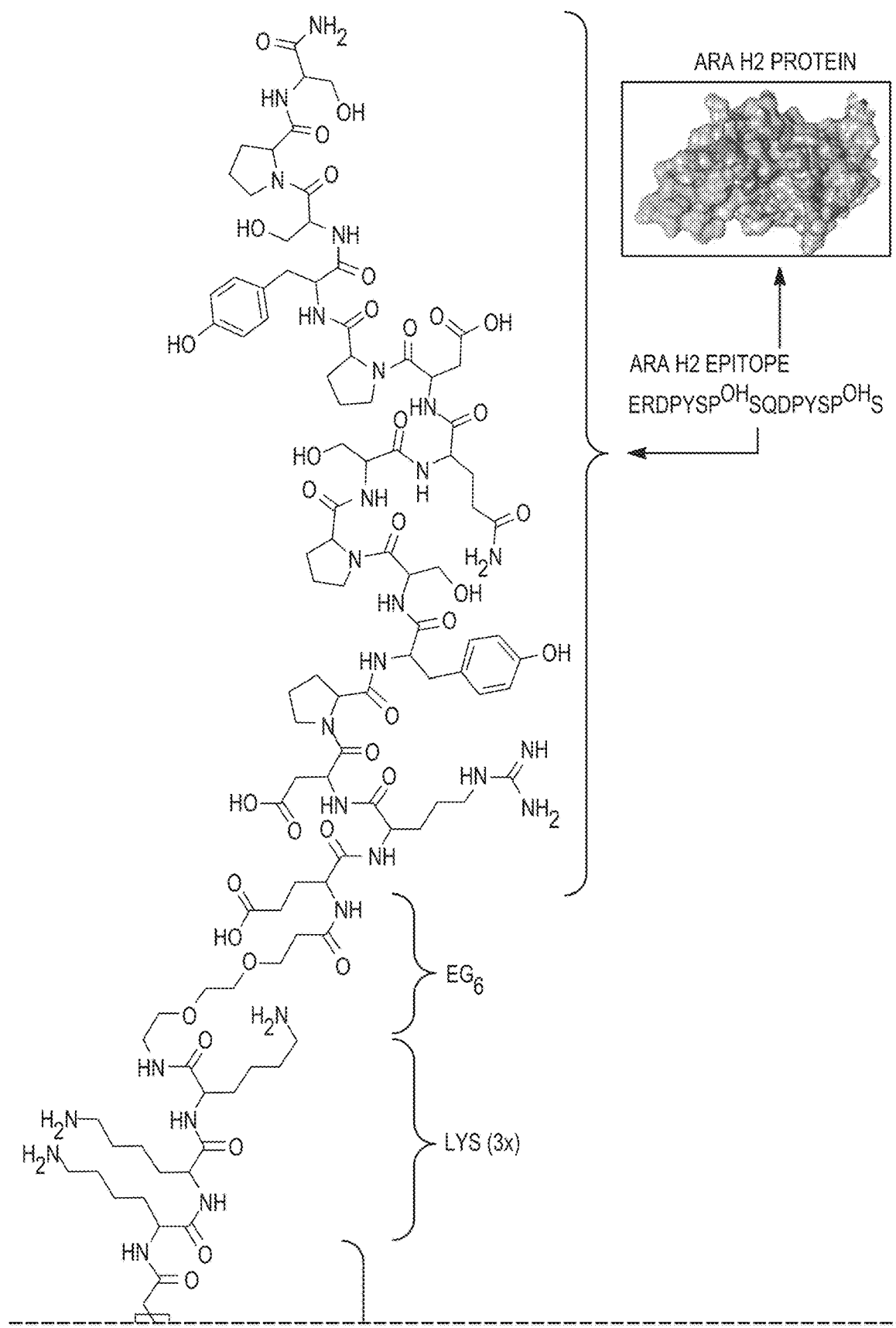
FIG. 7 illustrates a schematic of epitope-lipid conjugates. A linear peptide sequence of the peanut protein Ara h2 (residues 79-91) was attached to a lipid using the schematic given. The epitope (shown in green) is shown in context with the native Ara h2 protein (PDB: 3OB4). Note that the schematic was used for all other epitope-lipids.
Figure 7:
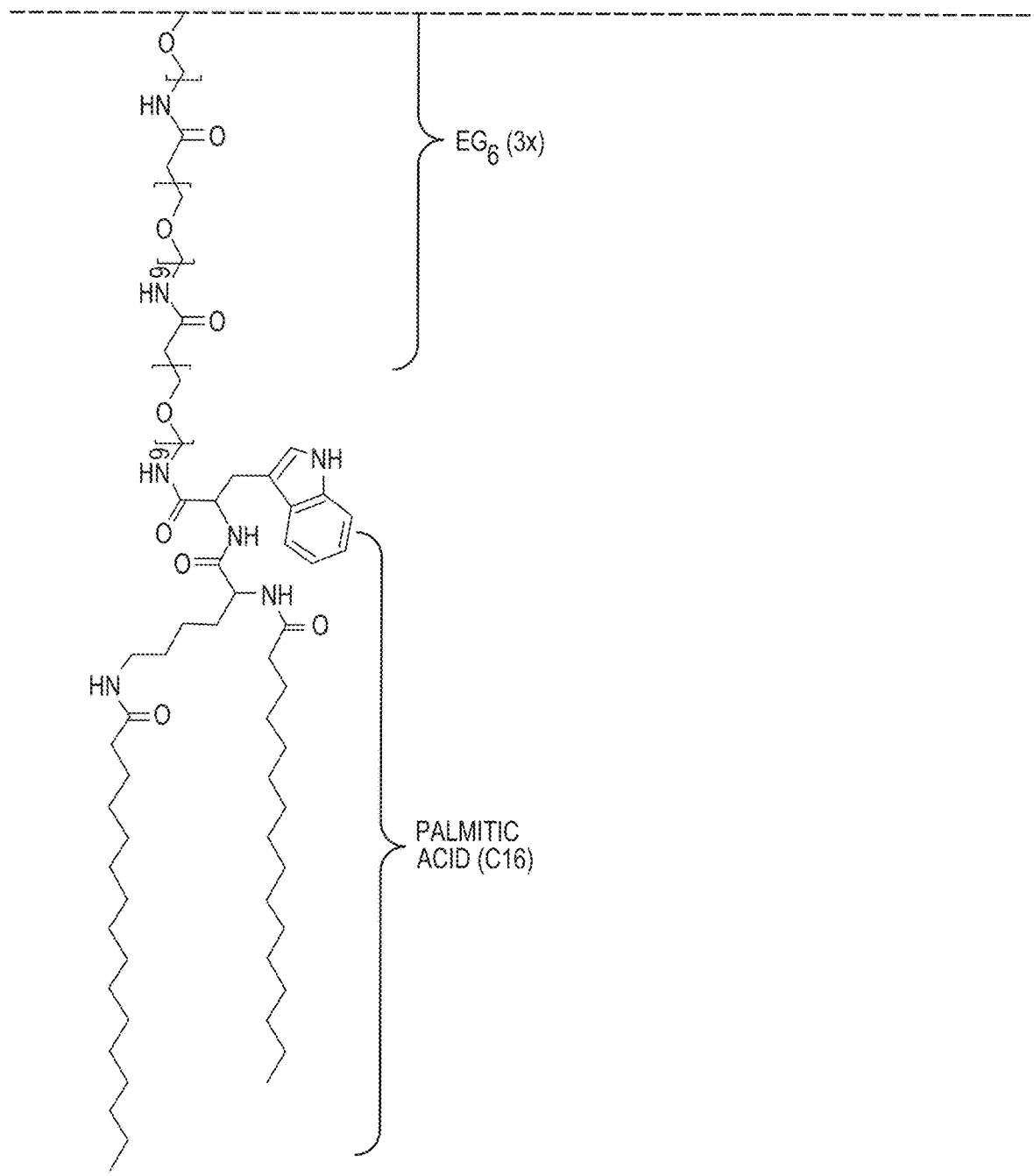

The lipid-epitope conjugates were synthesized with standard Fmoc solid phase peptide synthesis (SPPS) chemistry using NovaPEG Rink Amide resin as previously described. A sample lipid-epitope conjugate is shown in FIG. 7. For all lipid conjugates, epitopes were synthesized first using single amino acids and separated from the rest of the molecule with two ethylene glycols. Then, a variable oligolysine chain was added using Fmoc-Lys(Boc)-OH followed by a variable length of ethylene glycol (EG) was added using an Fmoc protected EG linker. Finally, Fmoc-Lys(Fmoc)-OH was added followed by palmitic acid to add two lipid tails per molecule. The procedure is described here briefly: protected molecules with terminal acid groups were activated with HBTU and a four-fold molar excess of DIEA for 5 minutes and then conjugated to the resin over 30 minutes. Fmoc was deprotected with 20% piperidine in DMF and IvDdE was deprotected using 2% hydrazine in DMF. Deprotection and coupling steps were monitored with Kaiser tests. Lipid-epitope conjugates were cleaved using a 95/2.5/2.5 TFA/water/TIS solution for 45 minutes. Lipid hapten molecules were purified using 1200 Agilent RP-HPLC using a semi-preparative Zorbax C3 column. A two phase water and 70/20/10 IPA/ACN/water mix was used for purification with a gradient of 60-100% IPA mix over 10 minutes at a flow rate of 3 mL/min. Hapten-amino acid conjugates were purified using a Zorbax C18 column, using a two phase water/ACN system with a gradient of 20-50% ACN in 10 minutes. Absorbance peaks at 220 nm and 280 nm were collected and verified for purity with analytical injections (>95%). The product was confirmed using a Bruker micro-TOF II mass spectrometer.

Nanoallergen Preparation.

Liposomal nanoallergens were prepared using a procedure as previously described. Briefly, DSPC, mPEG-2000-DSPC, cholesterol, and lipid-epitope conjugates were dissolved in chloroform, lyophilized for 30 minutes, rehydrated in PBS at 60° C. and then extruded through a 200, 100, 80 or 50 nm polycarbonate filter (Avanti).

Particle Characterization.

The size of liposomes was confirmed using DLS analysis via the 90Plus nanoparticle size analyzer (Brookhaven Instruments Corp., Long Island, N.Y.), using 658 nm light observed at a fixed angle of 90° at 20° C.

Cell Culture.

RBL-SX38 cells were a generous gift from Dr. Jean-Pierre Kinet from Harvard University. RBL-SX38 cells were cultured in Minimum Essential Media (Gibco) with 10% fetal bovine serum (Gemini BioProducts, Sacramento Calif.) and 1.2 mg/mL of G418 salt (Sigma) as previously described.

Degranulation Assays.

Degranulation assays were performed as previously described using nanoallergens as the allergen. RBL cells were plated into 96-well dishes for 24 hrs and then incubated with 10% of human sera in cell culture media for an additional 24 hrs prior to the degranulation assay.

ELISA Assay.

A high binding 96-well plate was incubated with anti-Human IgE in Carbonate-Bicarbonate buffer (Sigma) at a concentration of 3 nM for 16 hours at 4° C. Plate was washed with washing buffer (PBS with 0.5% tween 20) and then blocked with blocking buffer (5% BSA in PBS with 0.1% tween 20) for 1 hr at room temperature. Plate was washed with automatic plate washer (AquaMax 2000), then varying concentrations of either Ara h 2-Biotin (Indoors Biotechnologies) or FITC-peptide 2 conjugate in blocking buffer for 1 hour. Plate was washed again and then either streptavidin-HRP (1:5 000 dilution) or anti-FITC HRP IgG (1:5000 dilution) was added in blocking buffer. After washing, Amplex Red substrate was added (Invitrogen) and plate fluorescence read at 5 minute intervals according to manufacturers instructions.

Western Blot.

Stimulated RBL cells were analyzed for intracellular activity with a Western blotting technique previously described. RBL-SX38 cells were plated at approximately $0.5 \times 10^6$ cells per mL into a 3 mL dish for 24 hours. Cells were then incubated in 10% patient serum in cell culture media for 24 hours. Cells were then washed with Tyrodes buffer and incubated with Tyrodes from 30 minutes at 37° C. Ara h 2 or nanoallergens were then added at varying concentrations and incubated at 37° C. for 3 minutes. Cells were washed with ice cold PBS, then incubated in RIPA with phosphatase inhibitor lysis buffer, scrapped and sonicated for a minute intervals over the course of 30 minutes on ice. Lysates were then spun down at 15000 RPM for 10 minutes and their protein concentration determined by Bradford Assay. Laemmli buffer and PBS were added to all lysates so that their protein concentration was 0.5 mg/mL or would be 0.5 mg/mL prior to immunoprecipitation. Samples were boiled for 5 minutes; centrifuged and 20 uL of each was added to a 10% SDS-PAGE gel. Samples ran on the gel for 1 hr, were transferred to nitrocellulose paper for 1.5 hrs, and blocked with 5% BSA in TBS-T for 1 hr. Primary antibodies were added at the manufacturer's suggested dilutions in blocking buffer, washed with TBS-T, then appropriate secondary antibodies with HRP conjugates were added according to manufacturer's dilutions (typically 1:10000). The membranes were washed, and incubated in with Clarity™ Western ECL Blotting Substrate (Bio-Rad) for 5 minutes. Bands were exposed onto Kodak Chemiluminescence Film for times ranging from 1-30 minutes.

Example 2. Allergen Selection and Epitope Evaluation

Peanut allergies are one of the most common food allergies and affect 0.6% of the U.S. population or 1.8 million people. Therefore, peanut allergy proteins have been extensively studied, revealing potential allergen proteins. One of these is Ara h 2, a 17.5 kDa 2S albumin seed storage protein comprised of five alpha helices bound by four disulfide bonds. This is the major peanut protein, which has immunoreactivity with over 90% of the clinical peanut allergy population. A study by Stanley et al. proposed potential IgE binding epitopes for Ara h 2. Through computational studies and various IgE binding assays using patient sera, several other studies have also evaluated IgE binding epitopes of Ara h2. Applicants have performed a thorough evaluation of current literature on Ara h 2 IgE binding epitopes and have chosen eight potential IgE binding epitopes (SEQ ID NO: 5-12, FIG. 1A, Table A). These IgE binding epitopes were selected due to their established clinical IgE binding in at least two different studies and ranked based on their prevalence in the literature from most to least common.

TABLE A

Ara h2 Epitopes

| # | Sequence | Resides | Notes |
|---|---|---|---|
| 1 | NLRPCEQHLMQKIQRD | 38-53 | alpha hex 2 |
| 2* | ERDPYSP$^{OH}$SQDPYSP$^{OH}$S | 79-91 | |
| 3 | SDRLQGRQQ | 114-123 | |
| 4 | RRCQSQLER | 28-35 | alpha helix 1 |
| 5 | HASARQQWEL | 15-24 | |
| 6 | RQQEQQFKRELRNLPQQ | 120-136 | alpha helix 5 |
| 7 | PQRCDLE | 142-148 | |
| 8 | CDLEVESGGRDRY | 145-157 | C terminus of protein |

*Epitope 2 has two hydroxyproline post-translational modifications that were incorporated into the epitope-lipid conjugate.

Example 3. Nanoallergen Design and Characterization

The synthetic allergens, herein nanoallergens, are modified liposomes, which are spherical nanoparticles formed from a lipid bilayer of phospholipids. Liposomes have been used for many years as drug delivery vehicles and more recently have employed active targeting of disease relevant proteins through the use of targeting ligands expressed on the liposome surface. Recent advances in applicants' laboratory have developed techniques for precise loading of targeting elements by synthesizing peptide-lipid conjugates, purifying them and then forming liposomes. The techniques allow for precise control over particle size, formulation, peptide loading and the possibility for heterogeneous particles. Nanoallergens utilized similar peptide-lipid conjugates, where the peptide was a linear peptide sequence from an allergen protein, in this case, Ara h 2.

The most crucial component of the disclosed nanoallergens is the epitope-lipid conjugate, which was synthesized using well-established peptide-lipid conjugate chemistry developed in our laboratory. The epitope-lipid conjugates consist of three moieties: epitope peptides from Ara h 2, an ethylene glycol (EG) linker and two palmitate (C16) tails to facilitate the molecule's insertion into lipid membranes (SEQ ID NO: 5-12, FIG. 1A). The EG linker is variable in length and also contained variable length oligolysine chains that can be optimized to increase peptide availability on the surface of a liposome. However, in this study, the ethylene glycol linker consisted of 18 units (three EG6 spacers) and three lysines (FIG. 7). Applicants synthesized epitope-lipid conjugates of all eight Ara h 2 epitopes (Table 1). The liposomes were comprised of between 0.1-10% of epitope-lipid conjugate, a polyethylene glycol-lipid conjugate (5%), and the remaining percentage was a bulk phospholipid (DSPC). Nanoallergens also contained cholesterol (5% of total lipid) to improve particle stability. Unless otherwise stated, the nanoallergens in this study included 2% epitope-lipid conjugate and were 100 nm in diameter. See Examples 1 and 2 for further details regarding chemical synthesis, purification and liposome formation.

TABLE 1

Listing of Ara h 2 IgE binding epitope-lipid conjugates.

| Epitope-Lipid | Exact Mass (g/mol) | Purity (%) | Yield (%) | Immuno-reactivity |
|---|---|---|---|---|
| 1 | 4330.64 | 96.3 | 43.2 | None |
| 2 | 4094.33 | 99.6 | 61.2 | High |
| 3 | 3425.16 | 98.8 | 27.8 | Mild |
| 4 | 3498.23 | 96.2 | 35.3 | None |
| 5 | 3563.21 | 98.7 | 45.3 | Mild |
| 6 | 4563.78 | 97.4 | 36.2 | Mild |
| 7 | 3182.02 | 96.1 | 29.3 | Low |
| 8 | 3820.28 | 95.1 | 38.7 | None |

Example 4. Nanoallergens Stimulate Degranulation In Vitro

Figure 2A:
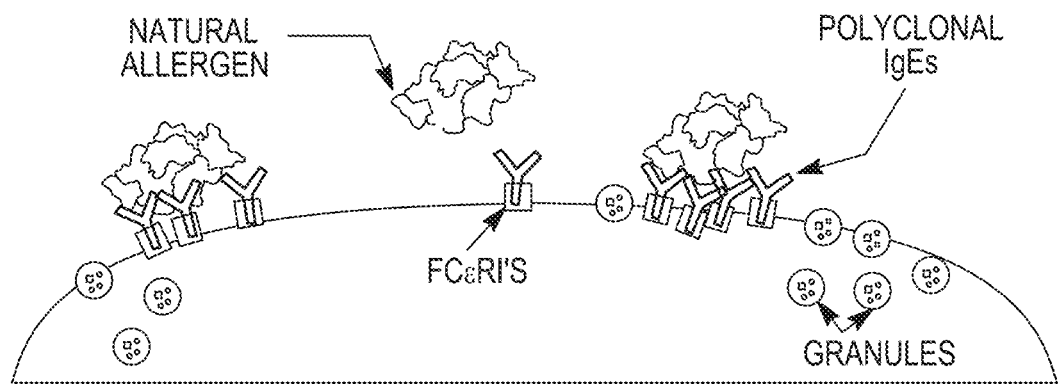
FIG. 2A-C illustrates an embodiment of nanoallergen loaded with epitope from Ara h2 protein stimulates degranulation. A cartoon depicting natural allergen triggering degranulation is shown in 2A and nanoallergen in 2B. This epitope-lipid conjugate was then loaded into nanoallergens at 2% total lipid and used to stimulate degranulation in cell transfected with the human FcεRI receptor (RBL-SX38 cells) that were primed with 25% serum from a peanut allergy patient show in 2c (Plasma Labs, Everett, Wash.).
Figure 2B:
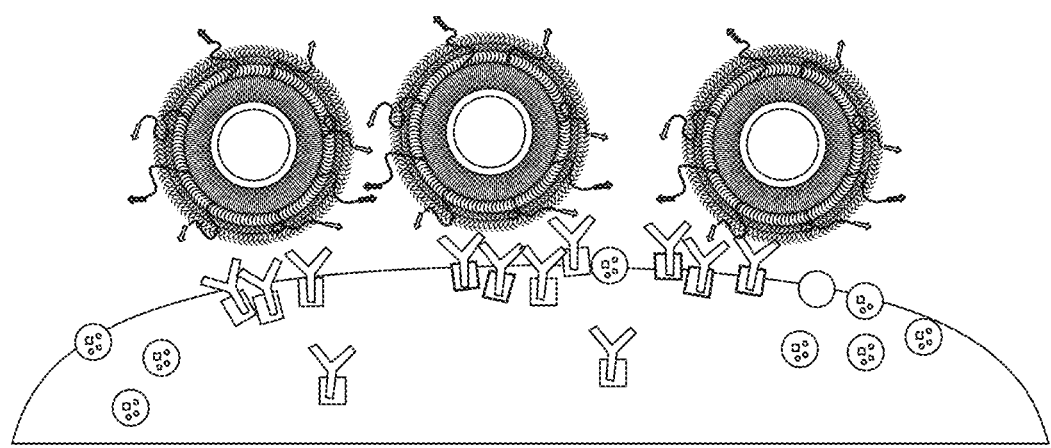
Figure 2C:
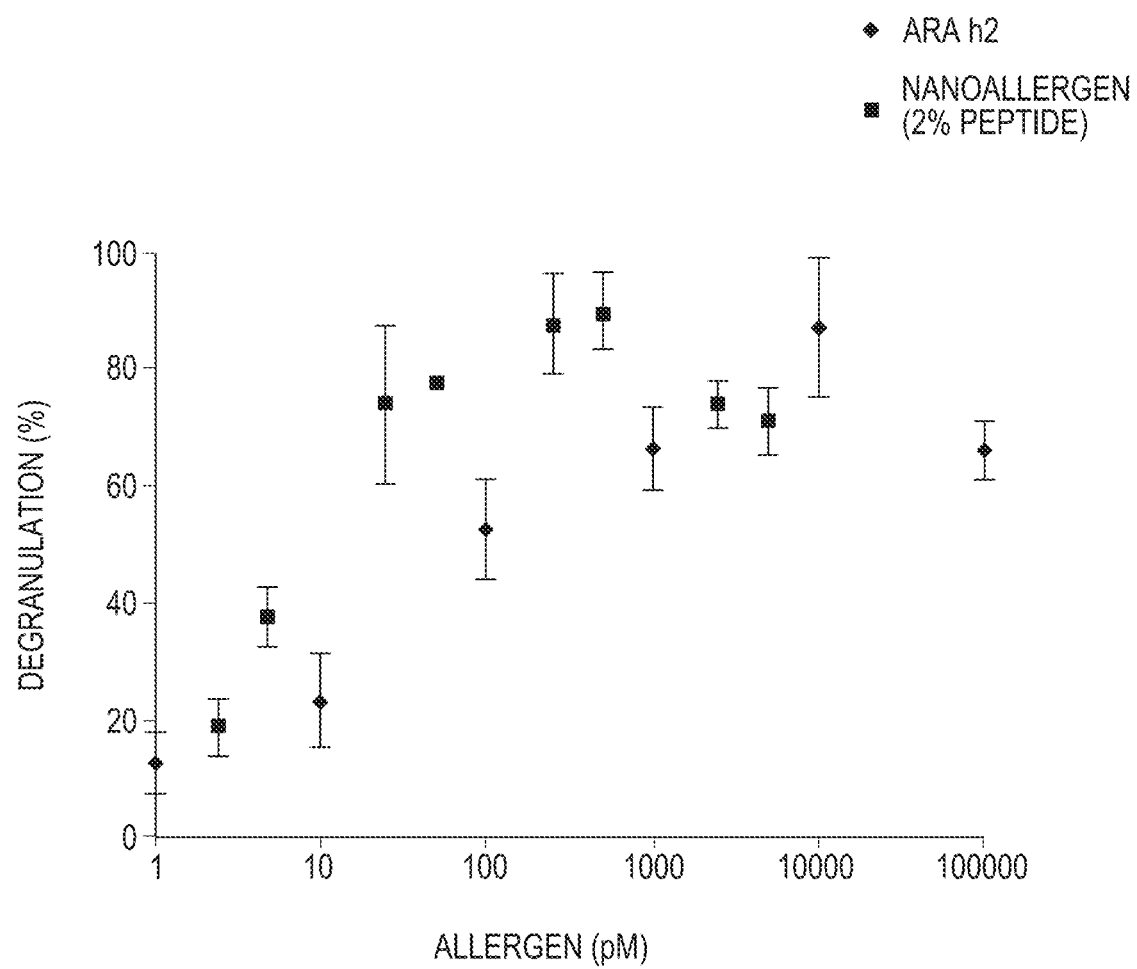
Figure 8:
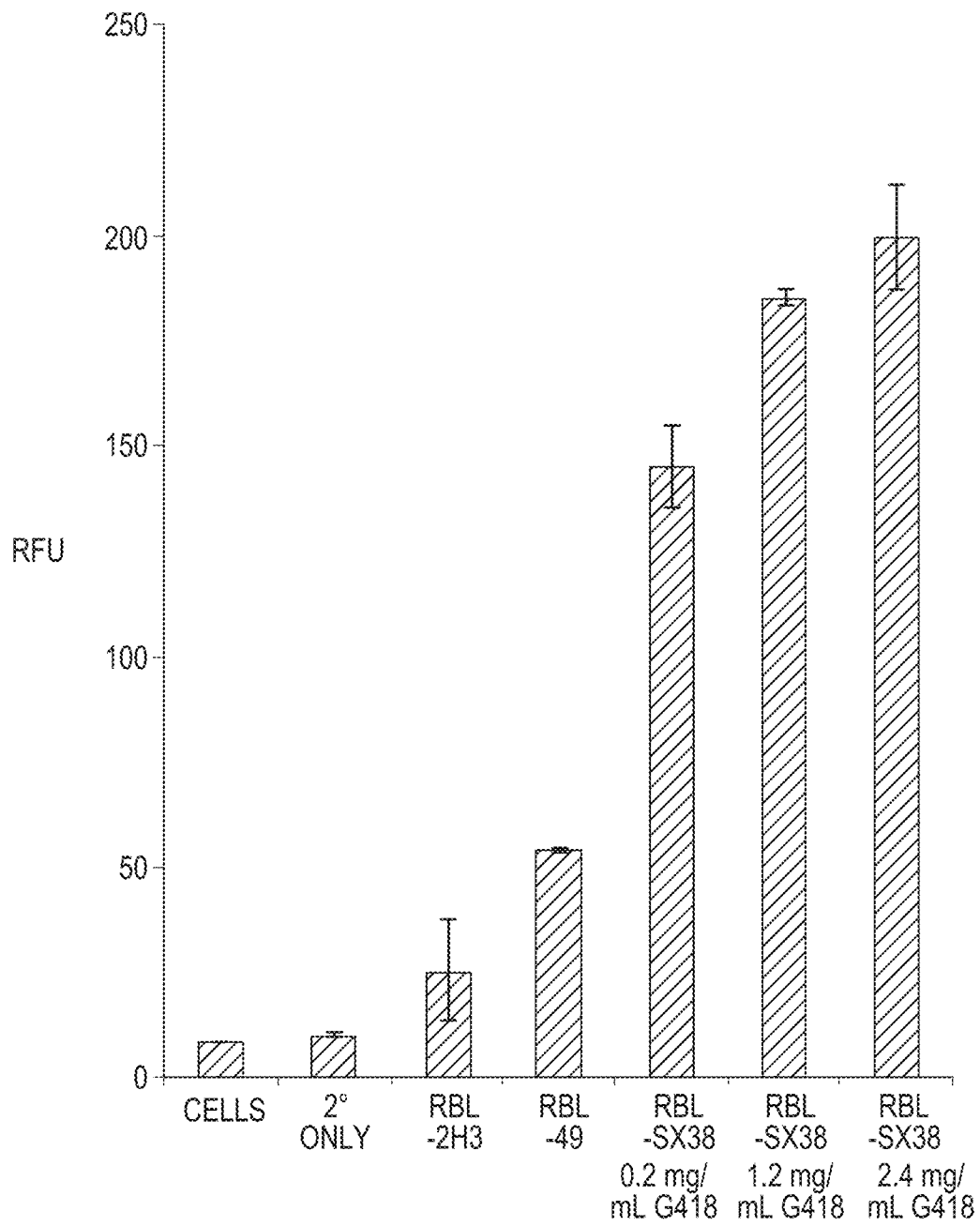
FIG. 8 illustrates flow cytometry data demonstrating the presence of human FcεRI receptors on the surface of RBL cells.
Figure 9:
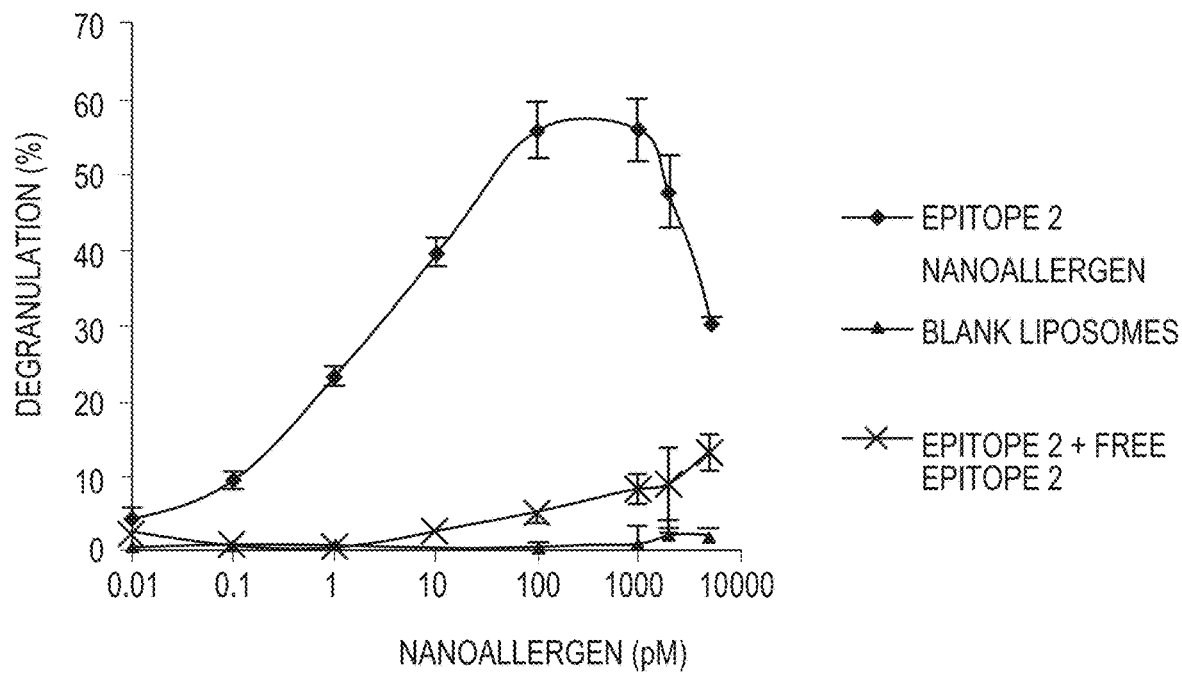
FIG. 9 illustrates nanoallergens demonstrate specificity, as their degranulation response can be prevented with addition of 100 μM of free peptide 2. Likewise, blank liposomes do not cause a degranulation response.

The primary goals of this study were (1) to demonstrate the effectiveness of nanoallergens to induce degranulation in vitro using allergy reactive human sera and (2) to determine crucial antigenic epitopes of Ara h2 in the clinical population. Therefore, applicants' first concern was to demonstrate that nanoallergens can stimulate degranulation of mast-like cells in vitro with the same sensitivity and specificity of natural allergens. Using the mast-like rat basophil leukemia SX38 (RBL) cell line that has been transfected to express the human FcεRI on their surface, applicants can use peanut reactive patient sera in applicants' cellular degranulation assays (FIG. 8). The RBL cells become sensitized when IgEs from the patient sera (including those reactive to peanuts) tightly bind to the high affinity FcεRI. After sensitization, applicants added varying concentrations of either Ara h 2 or nanoallergens with 2% of epitope 2 lipid loaded into the liposome. As demonstrated by FIGS. 2A and 2B, nanoallergens should be able to stimulate similar degranulation responses as Ara h 2 by crosslinking allergy reactive IgEs multivalently. As demonstrated by FIG. 2C, nanoallergens are able to stimulate degranulation at approximately 10 fold lower concentrations than Ara h 2. Similarly, primed RBL cells did not have any degranulation response to liposomes with no epitope-lipid conjugates (blank) or to epitope peptide 2 nanoallergens given in combination with free epitope peptide, indicating the specificity of the degranulation response (FIG. 9). The data also demonstrated a characteristic bell shaped curve for allergen proteins (FIG. 2C).

Figure 3:
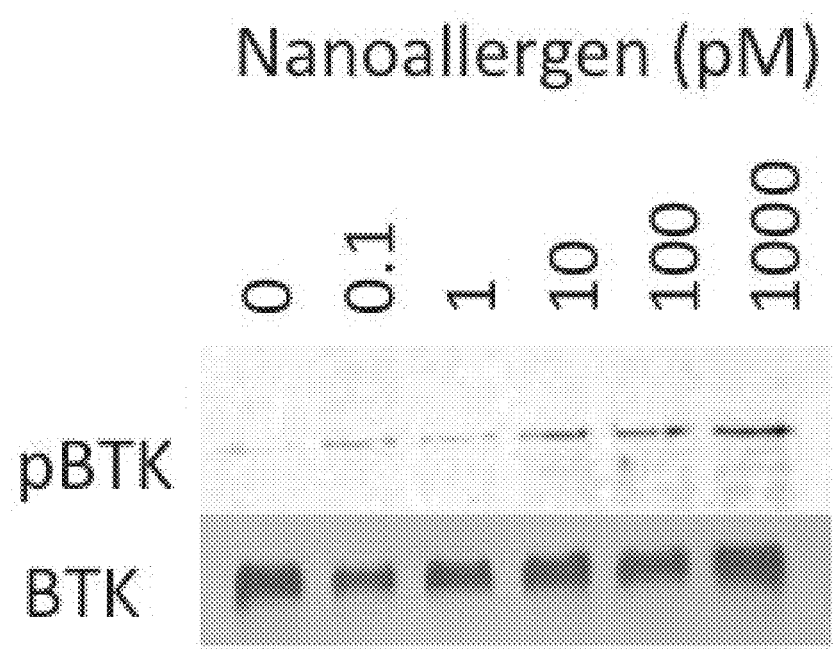
FIG. 3 illustrates nanoallergen stimulation of BTK phosphorylation. 2% epitope 2 loaded nanoallergens were incubated with RBL cells at varying concentrations and a Western blot performed to assess BTK phosphorylation.
Figure 11A:
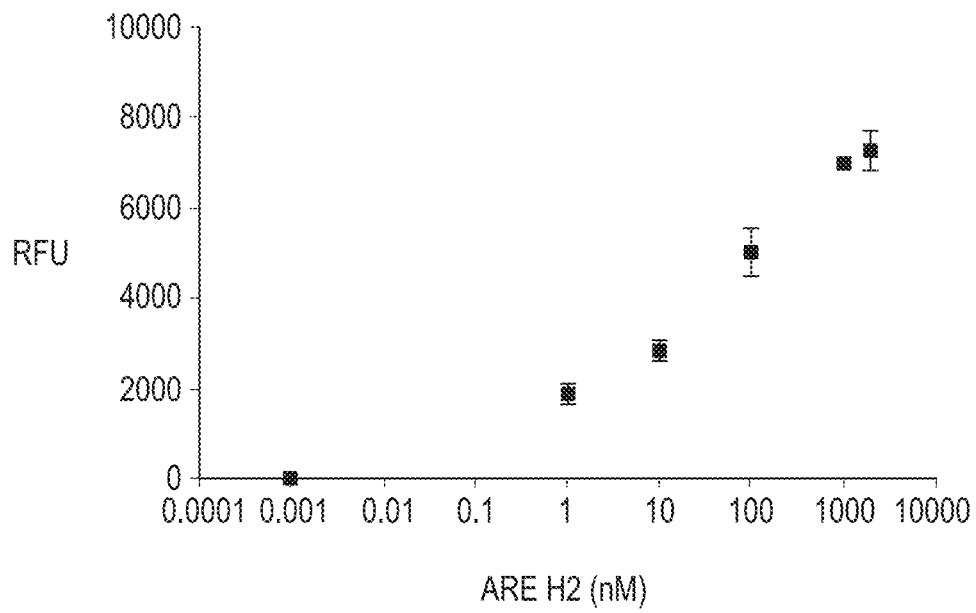
FIG. 11 illustrates ELISA binding assay with patient sera. Patient serum 0 was added to a 96-well plate coated with anti-IgE IgG, washed and then either Ara h 2-Biotin (A) or FITC-tagged epitope 2 peptide (B) and the binding was observed using ELISA. Their maximum signal was compared in C., demonstrating that approximately 10% of Ara h 2 IgE are specific for epitope 2. Ara h2–EC50=40±27 nM; Pep2–EC50=465±200 nM
Figure 11B:
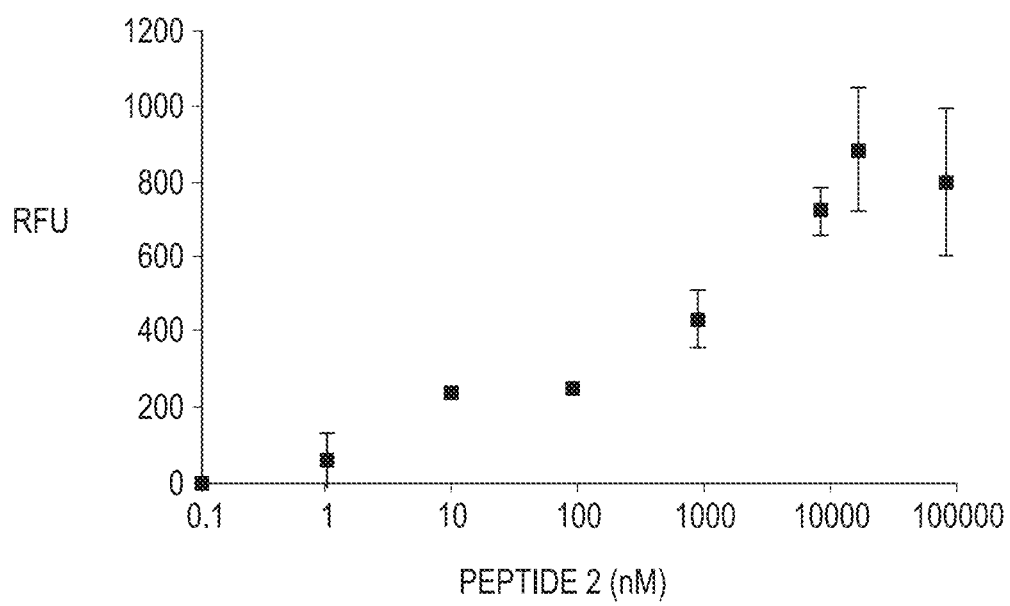
Figure 11C:
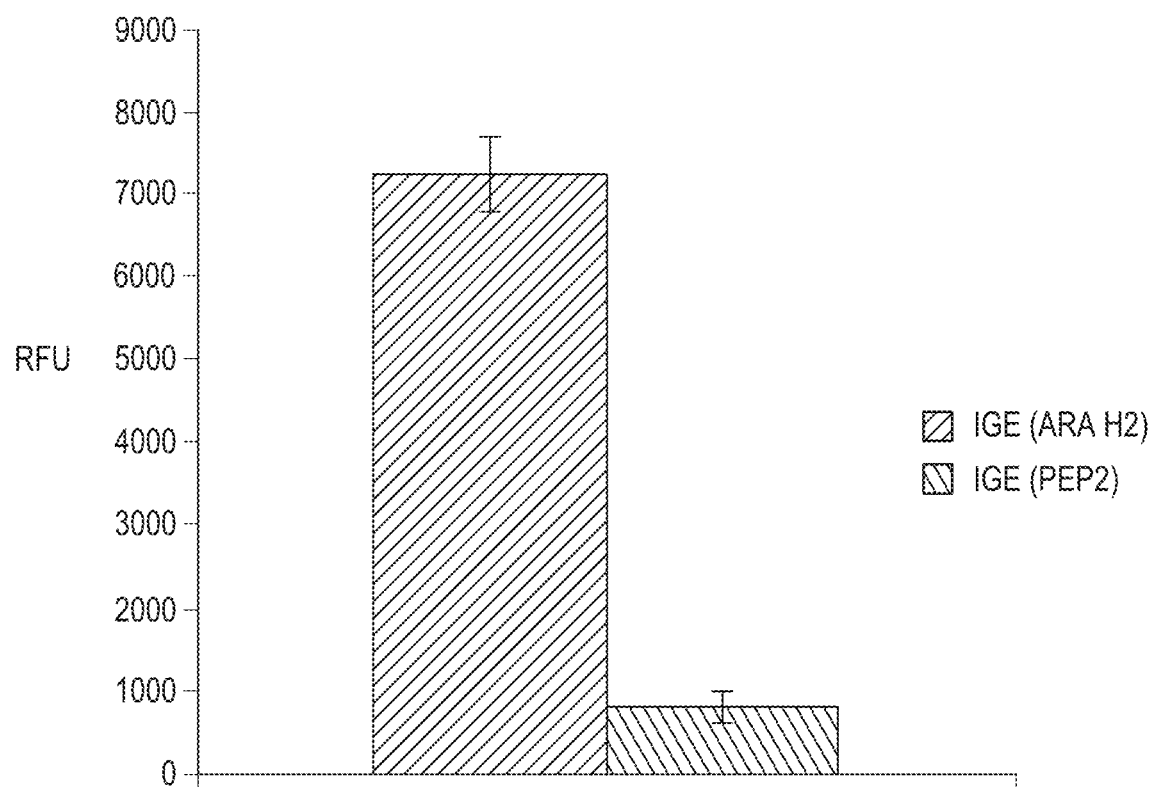
Figure 12A:
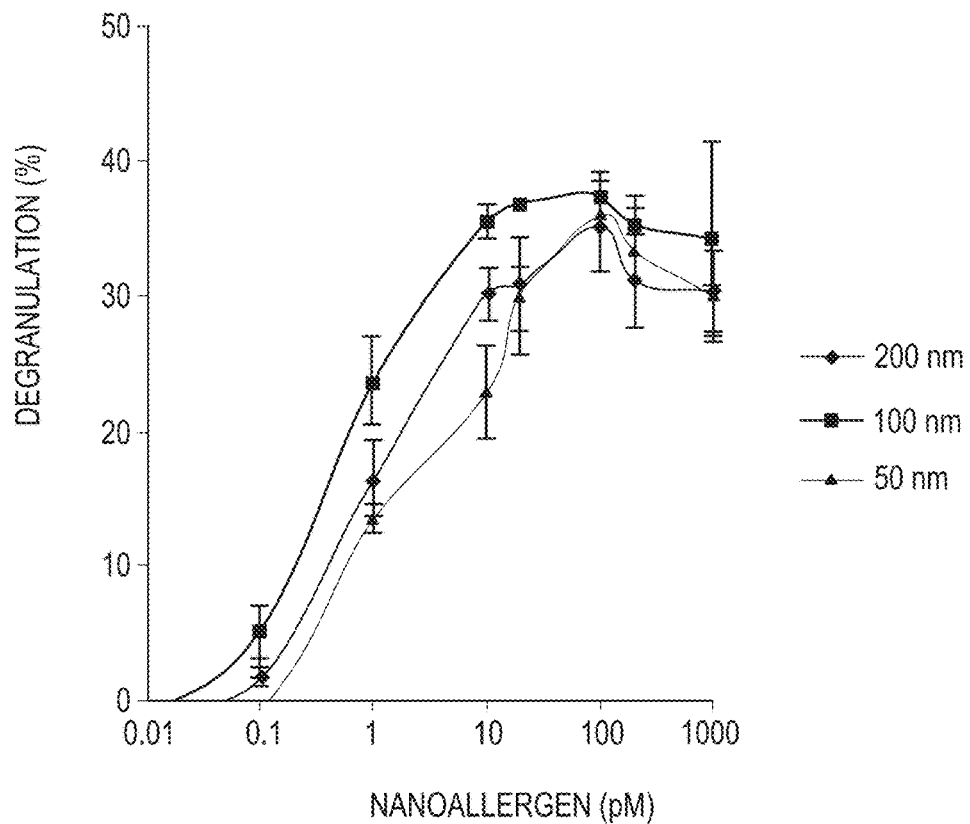
FIG. 12A-B illustrates nanoallergens can be formed with various sizes as seen in (A) and with varying epitope loading as seen in (B).
Figure 12B:
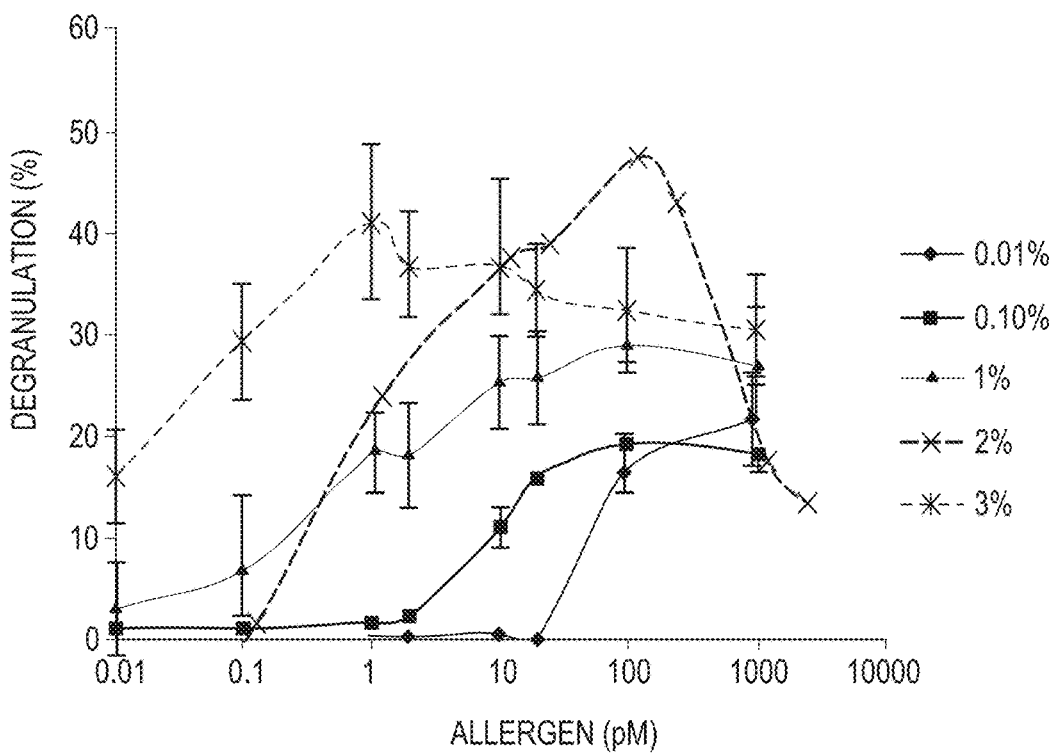
Figure 13:
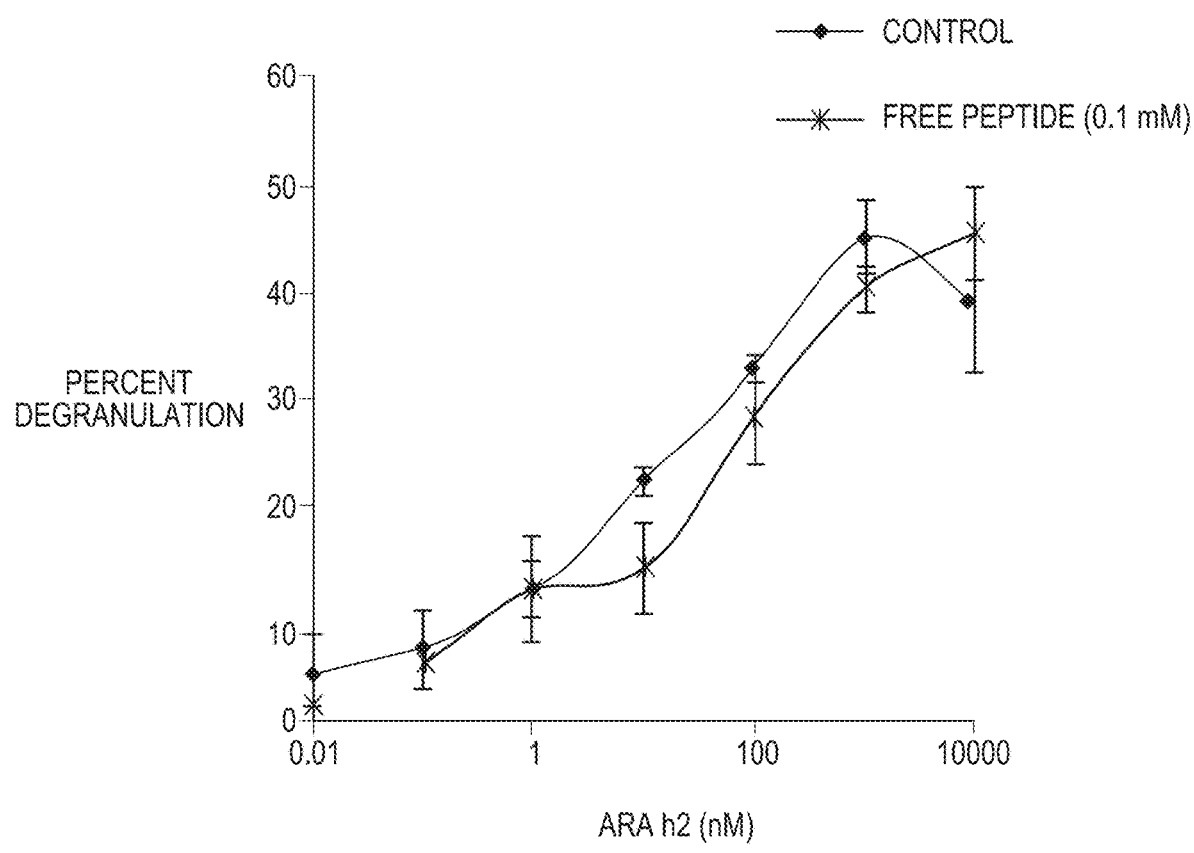
FIG. 13 illustrates the addition of free epitope peptide 2 did not prevent Ara h 2 protein from triggering degranulation. Ara h 2 was used to trigger degranulation with and without the presence of 100 μM free epitope 2.
Figure 14A:
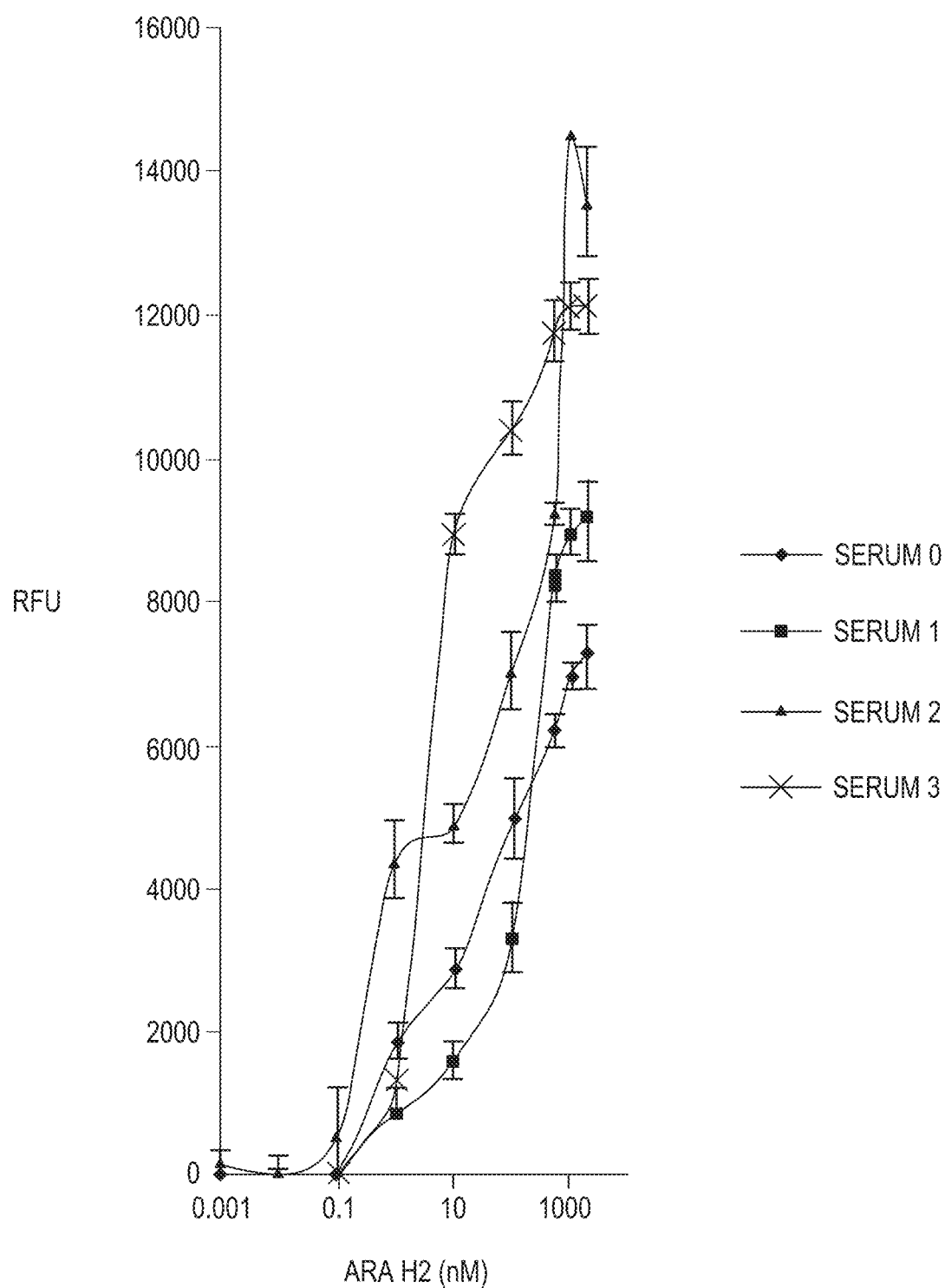
FIG. 14A-B illustrates ELISA binding data for additional sera. Either Ara h 2 (A) or free epitope peptide 2 (B) was used to bind patient IgEs.
Figure 14B:
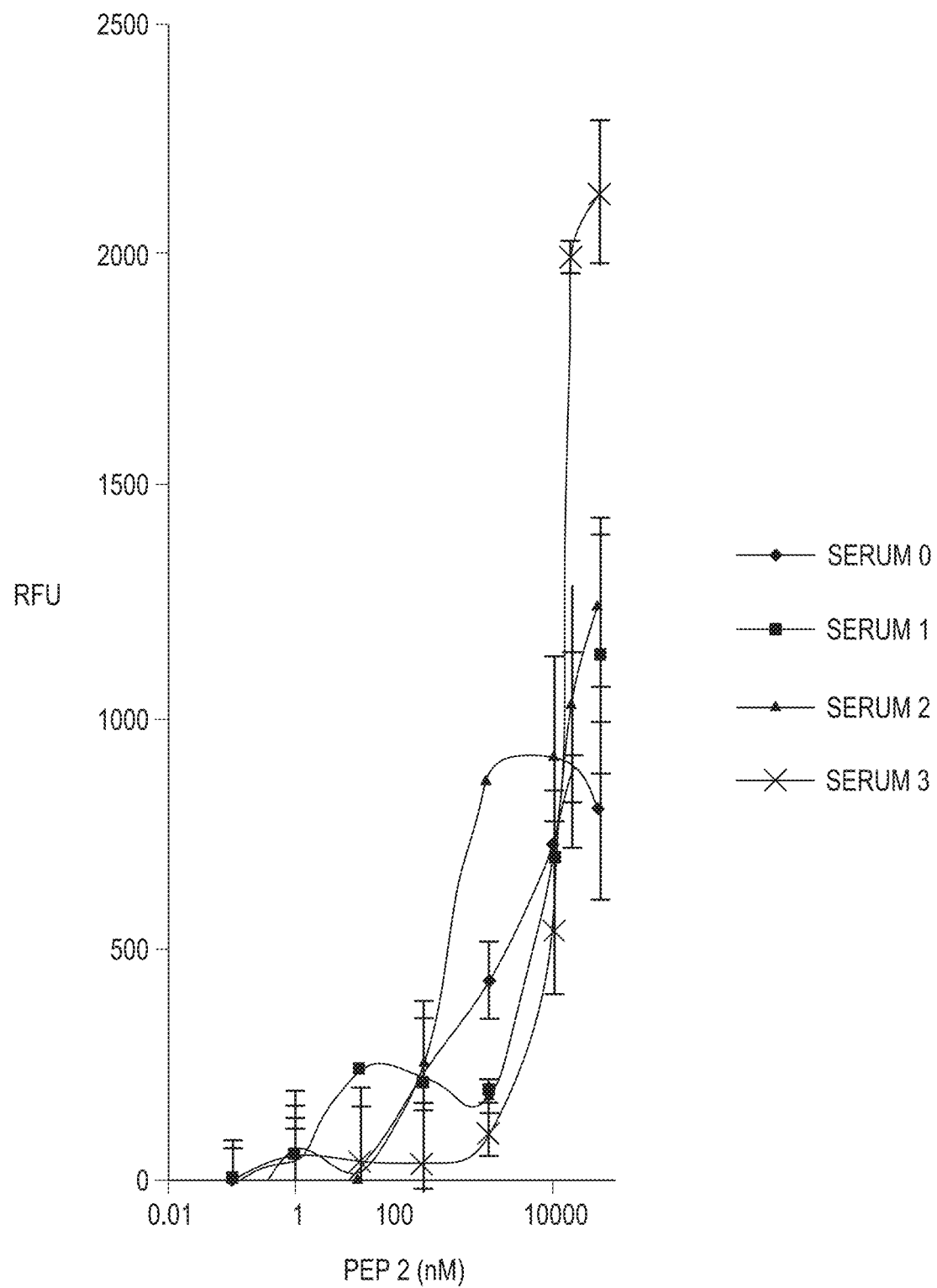
Figure 15:
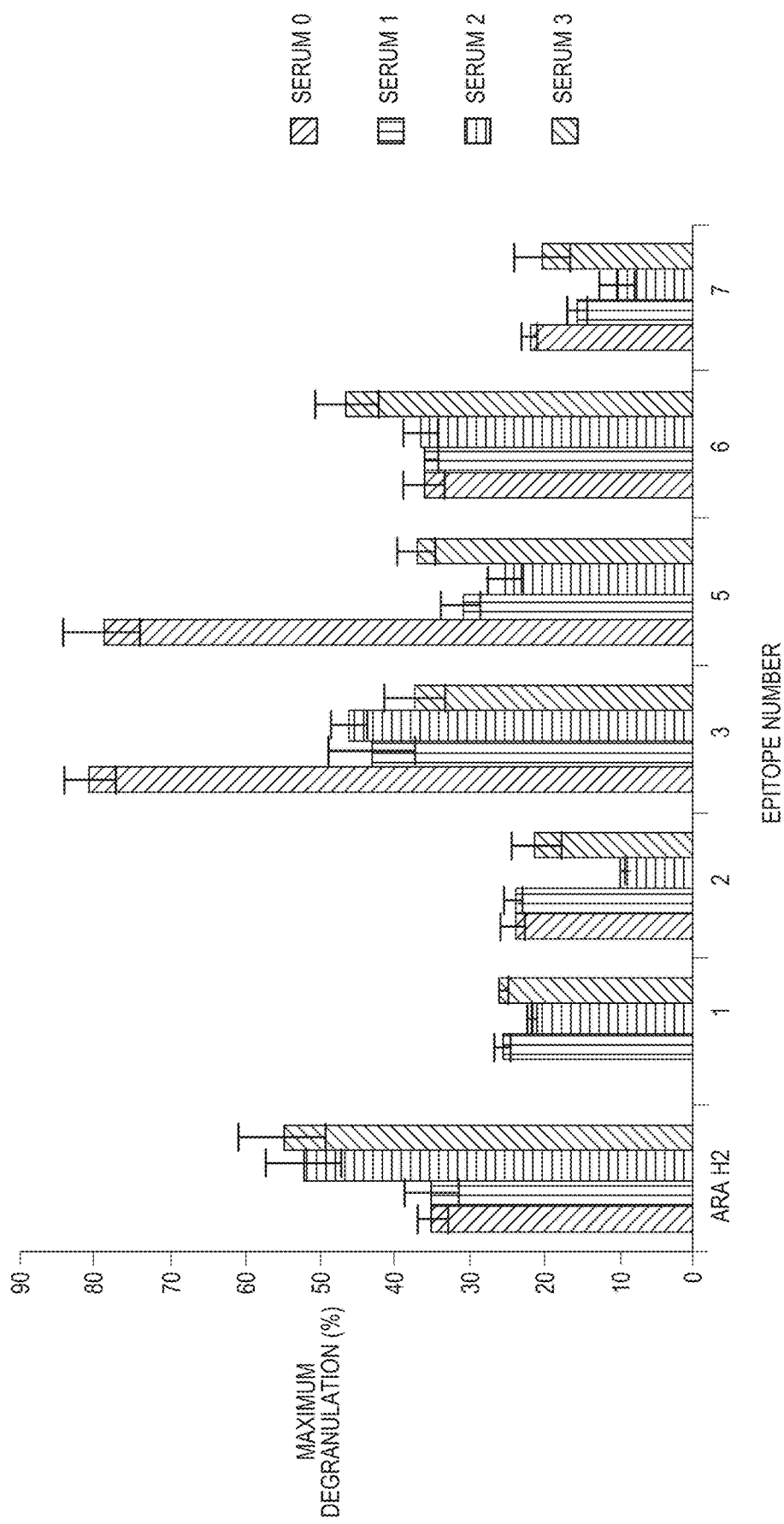
FIG. 15 illustrates maximum degranulation values for all patient sera/epitope combinations.
Figure 16A:
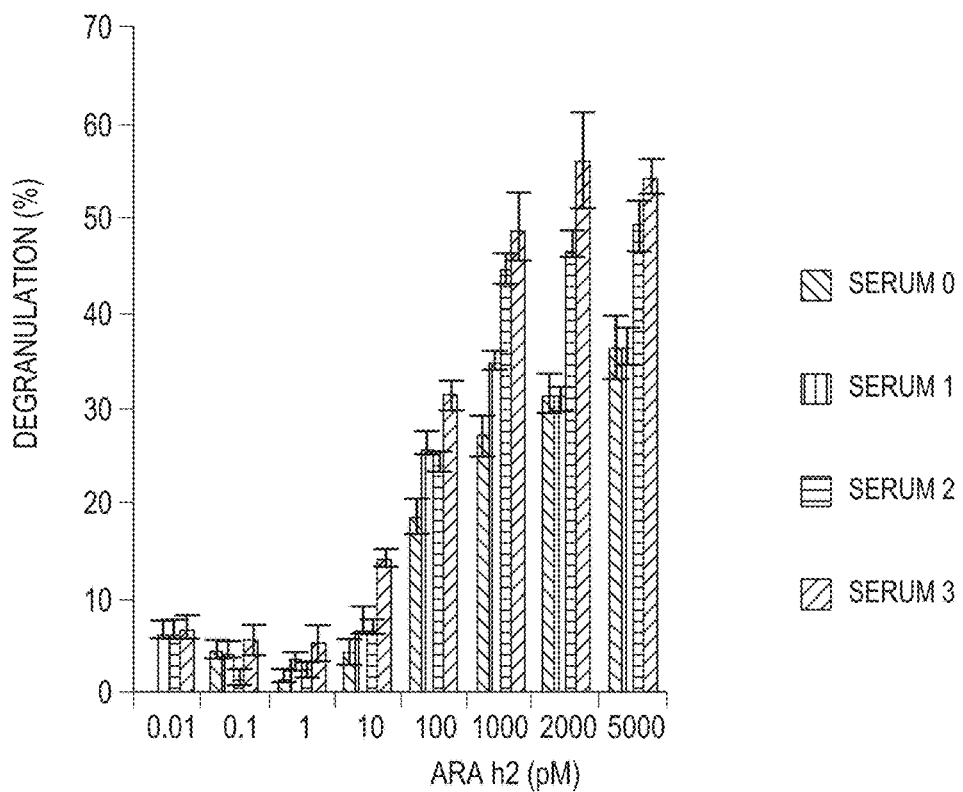
FIG. 16A-I illustrates raw data for all patient sera/epitope combinations for Ara h 2. Note that 2% epitope loading was used for all assays. (A) is for Ara h 2 protein, while B-I demonstrates epitope 1-8 respectively.
Figure 16B:
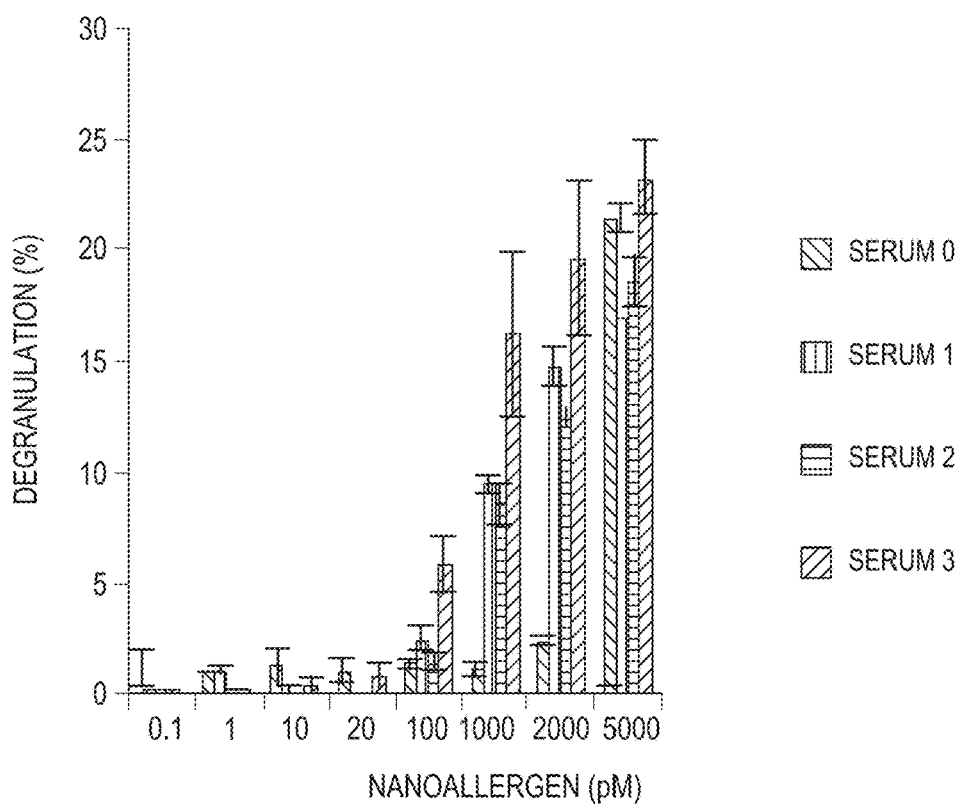
Figure 16C:
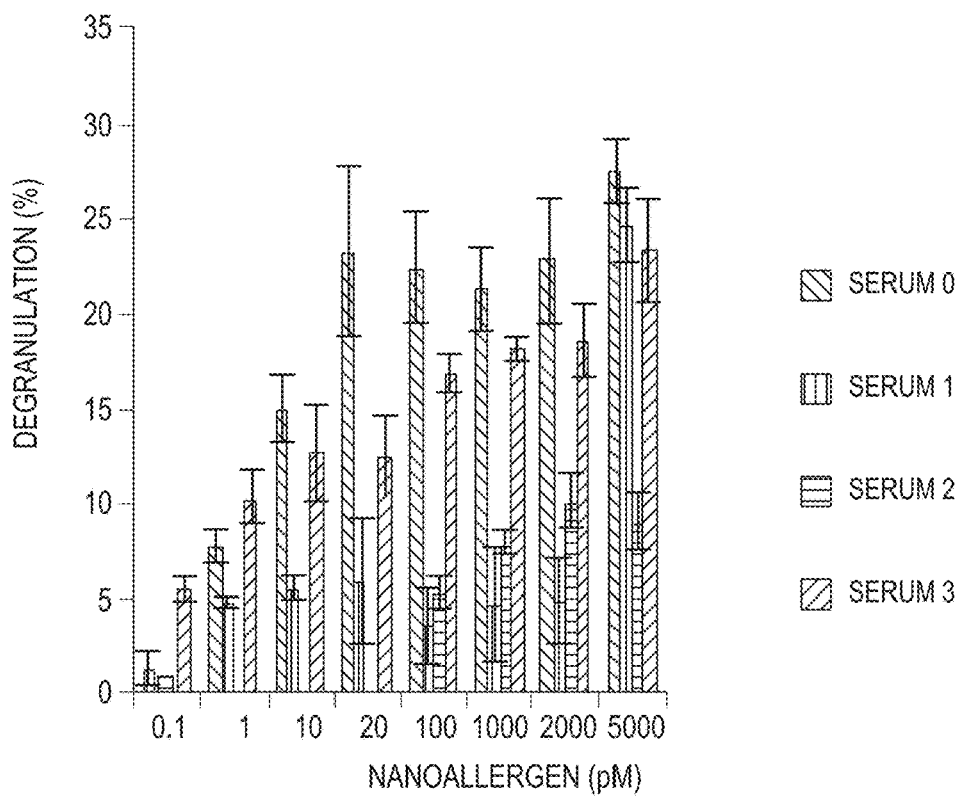
Figure 16D:
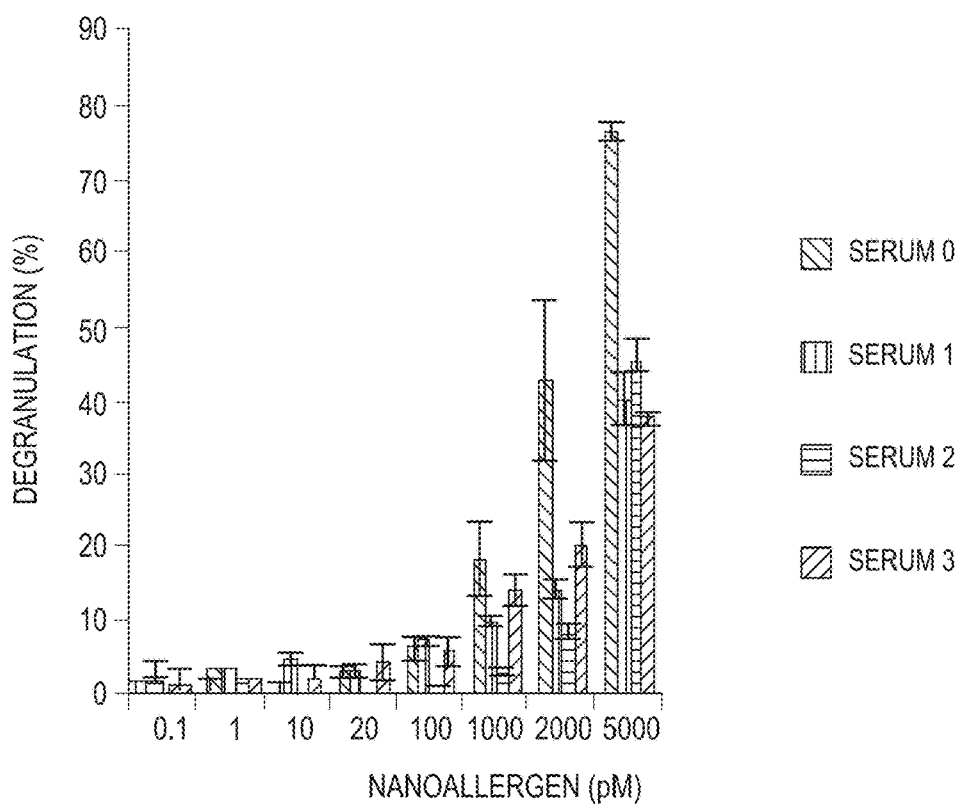
Figure 16E:
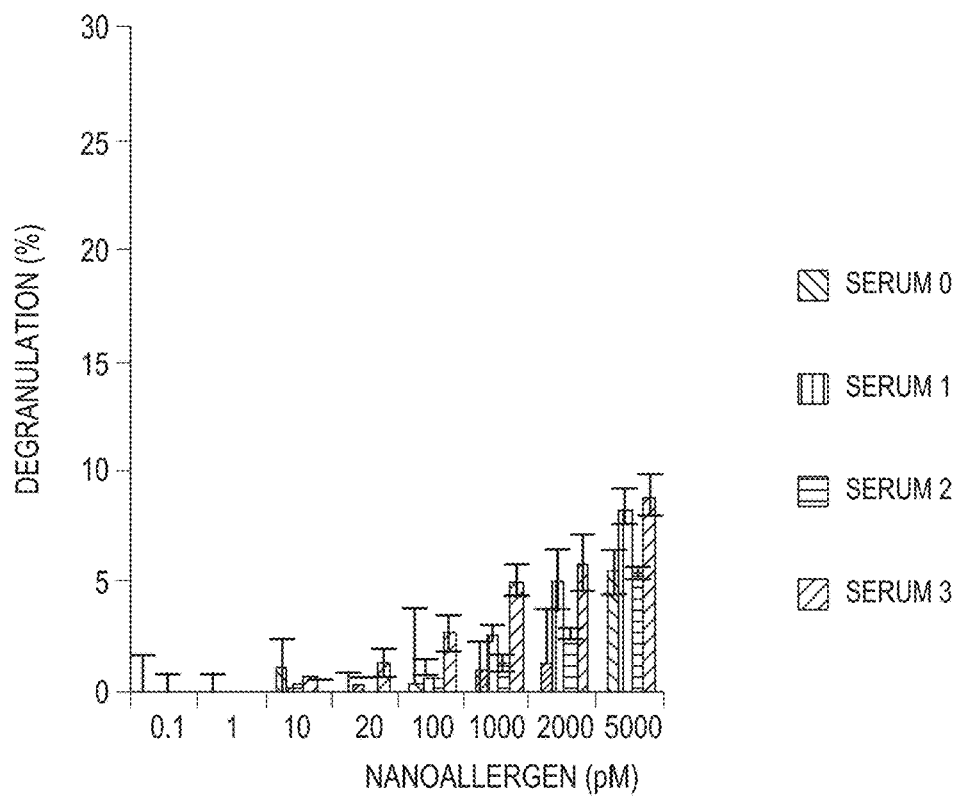
Figure 16F:
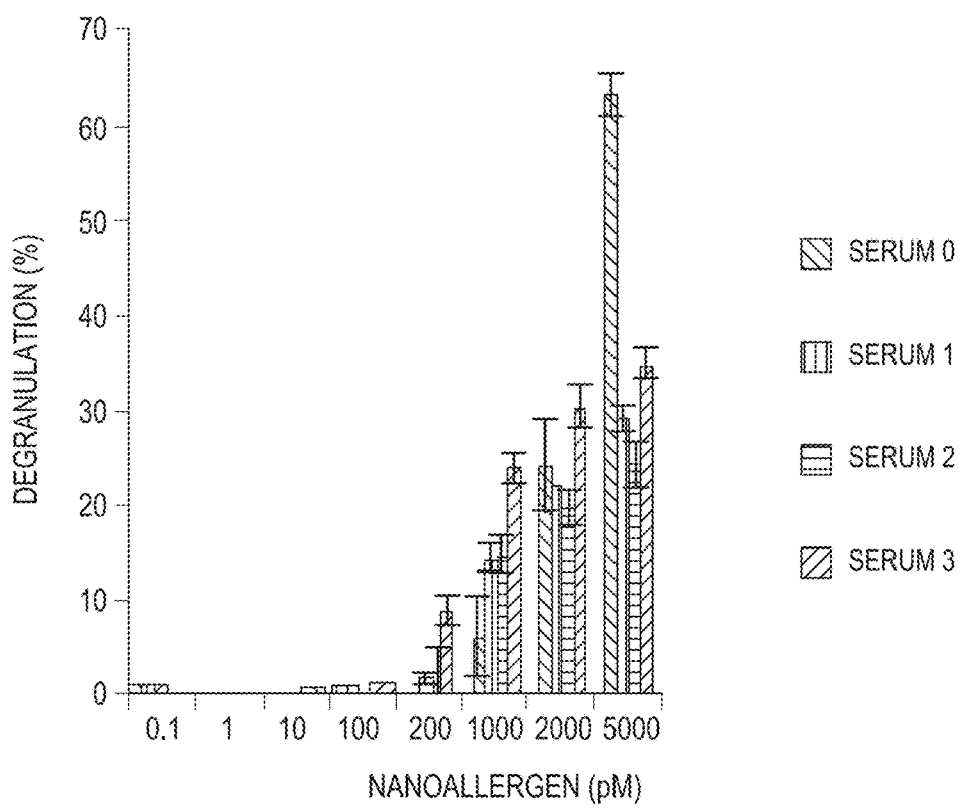
Figure 16G:
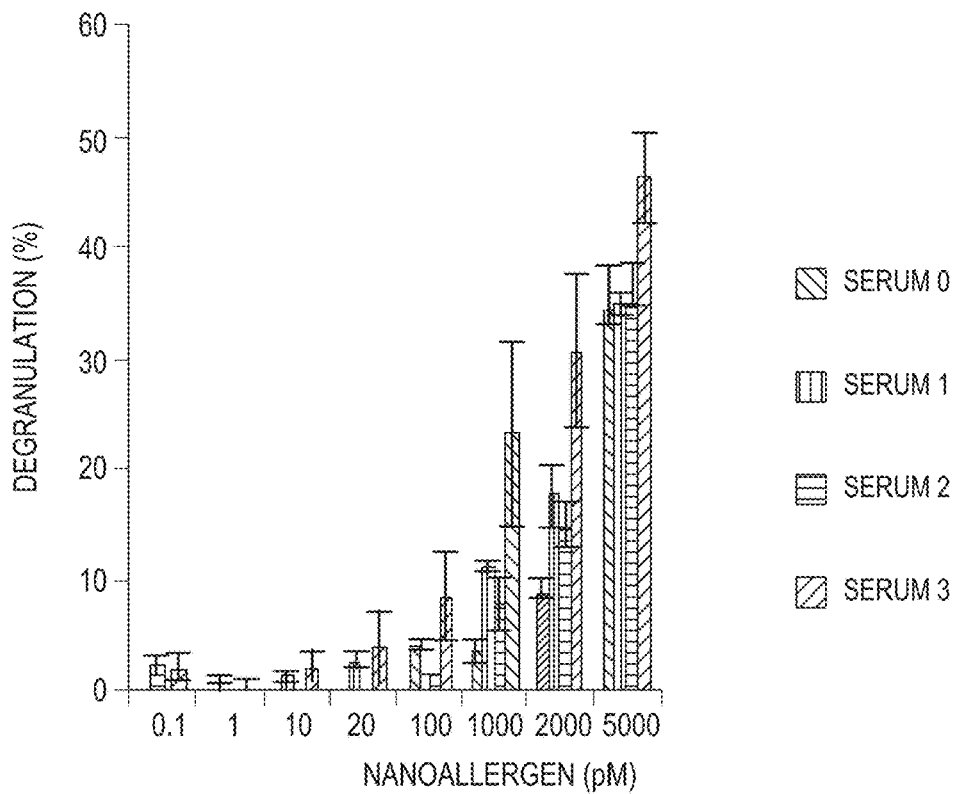
Figure 16H:
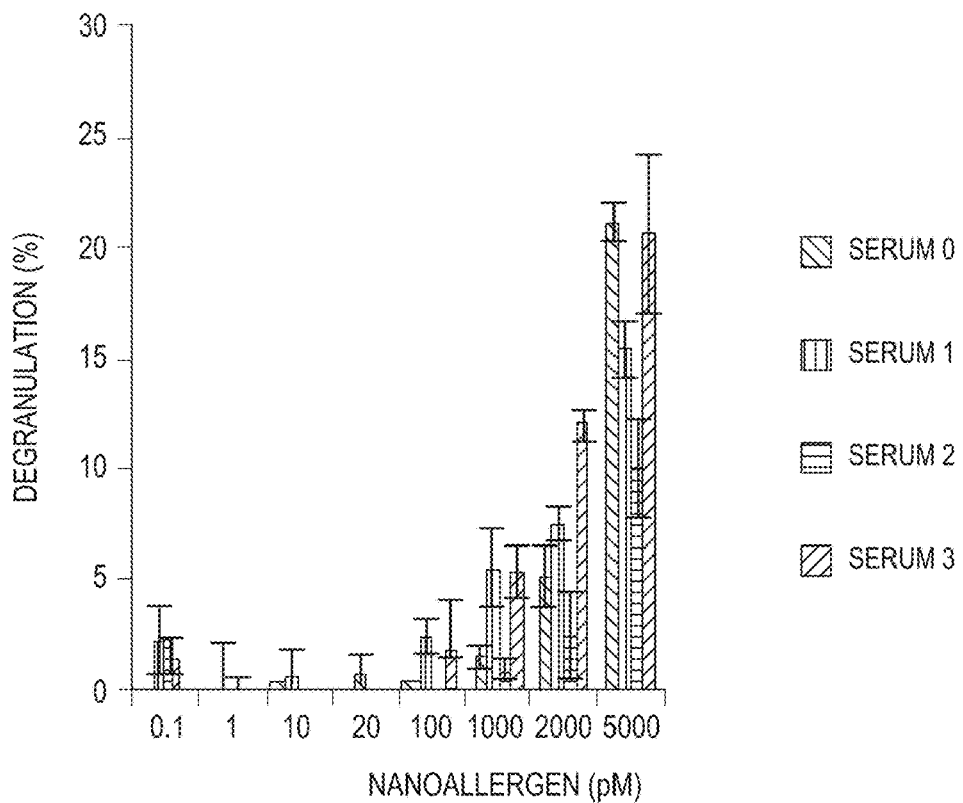
Figure 16I:
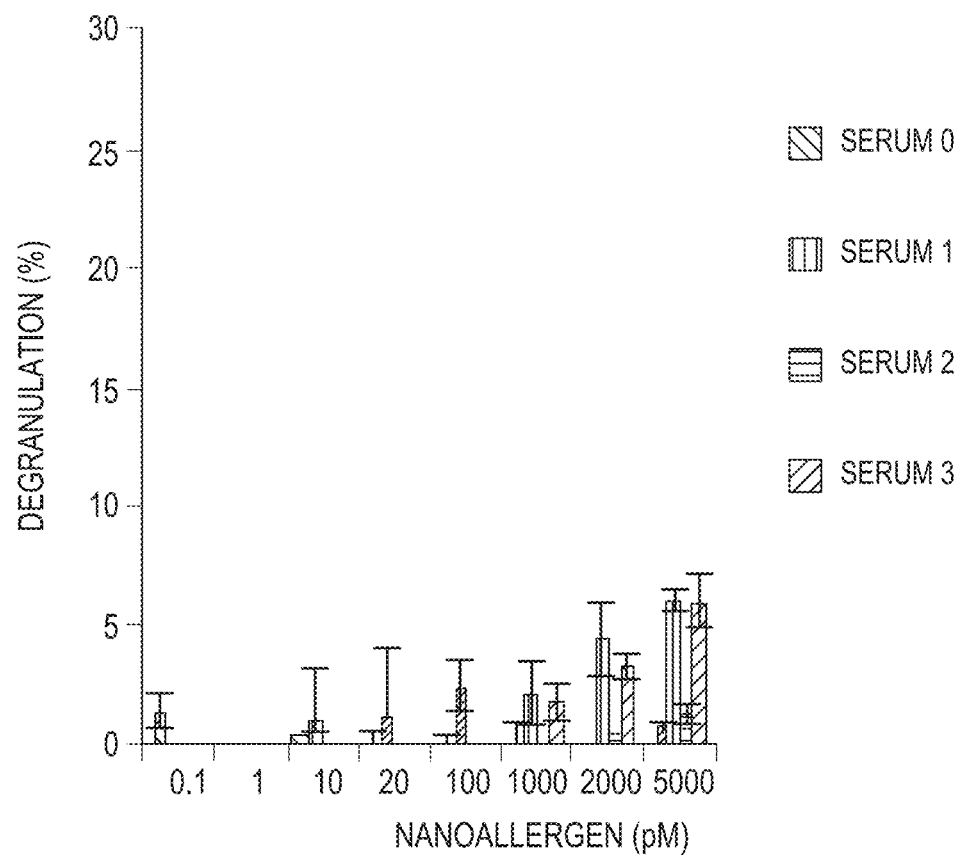
Figure 17A:
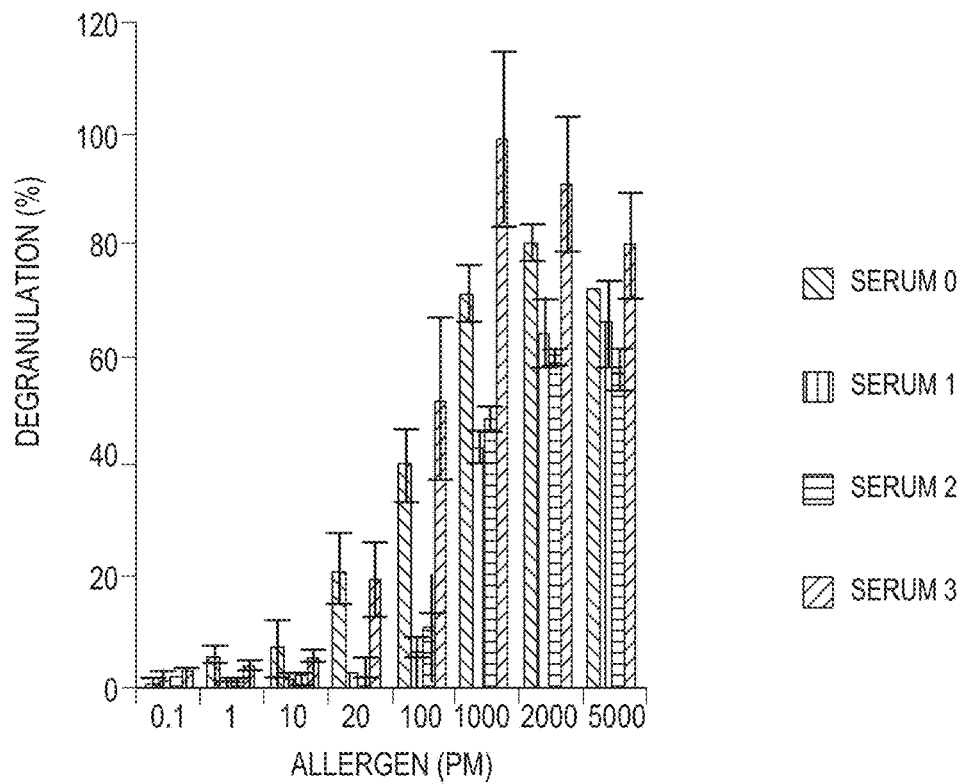
FIG. 17A-H illustrates raw data for all patient sera/epitope combinations for Ara h 6. 2% epitope loading was used for all assays. (A) is for Ara h 6 protein, while (B)-(H) demonstrate epitope 1-7, respectively.
Figure 17B:
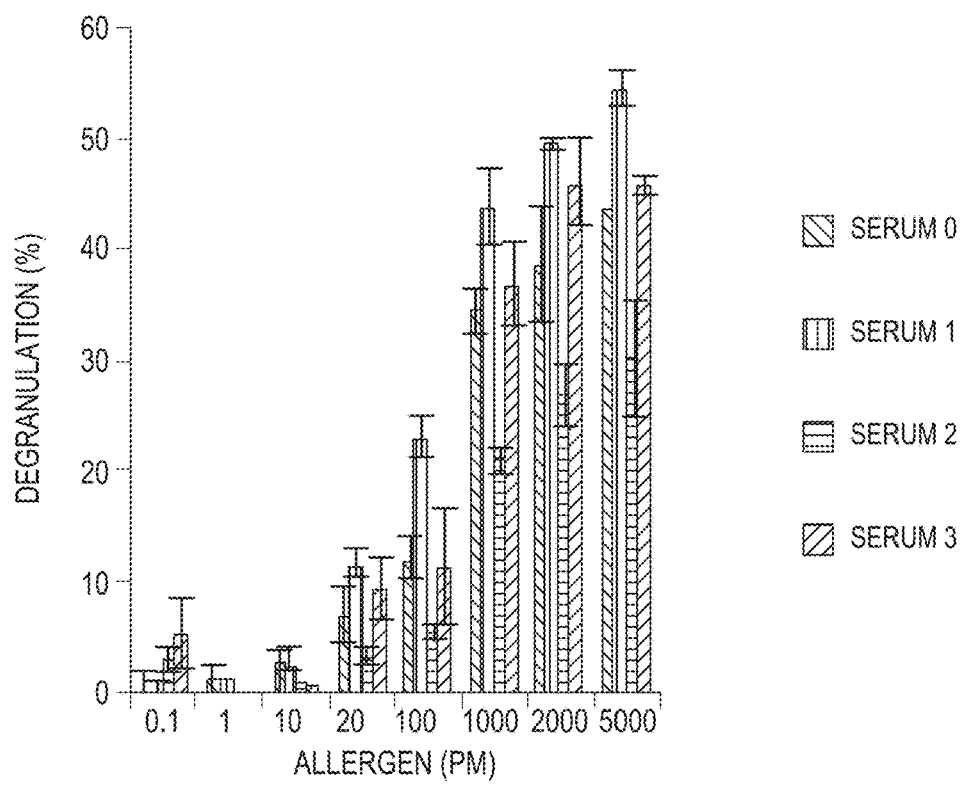
Figure 17C:
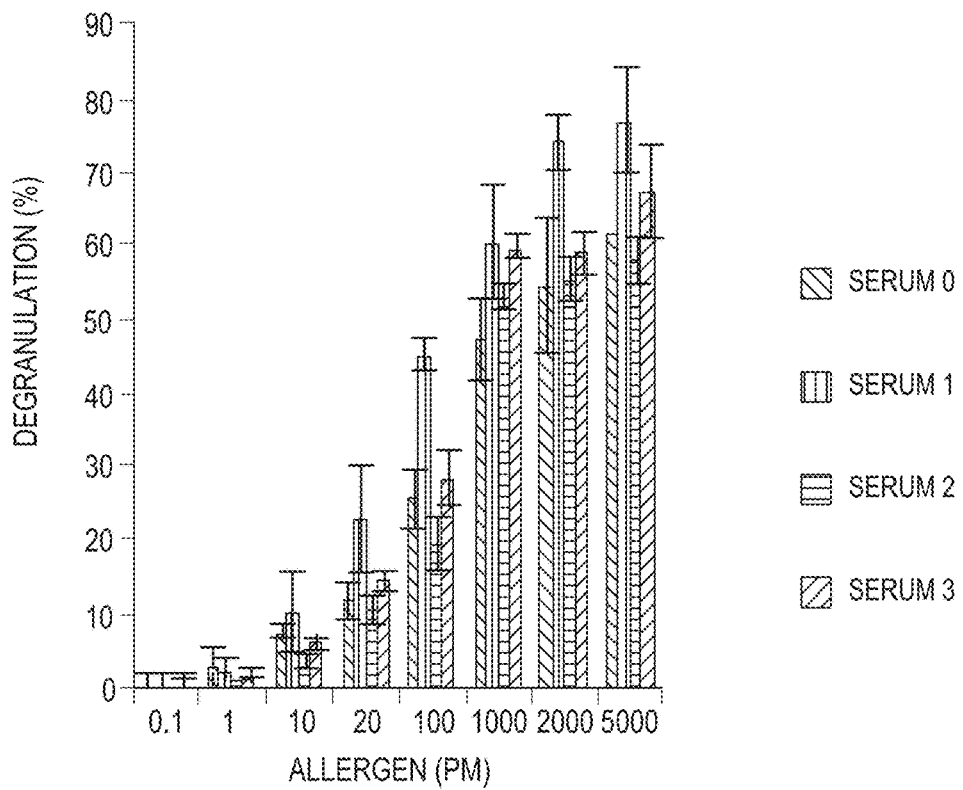
Figure 17D:
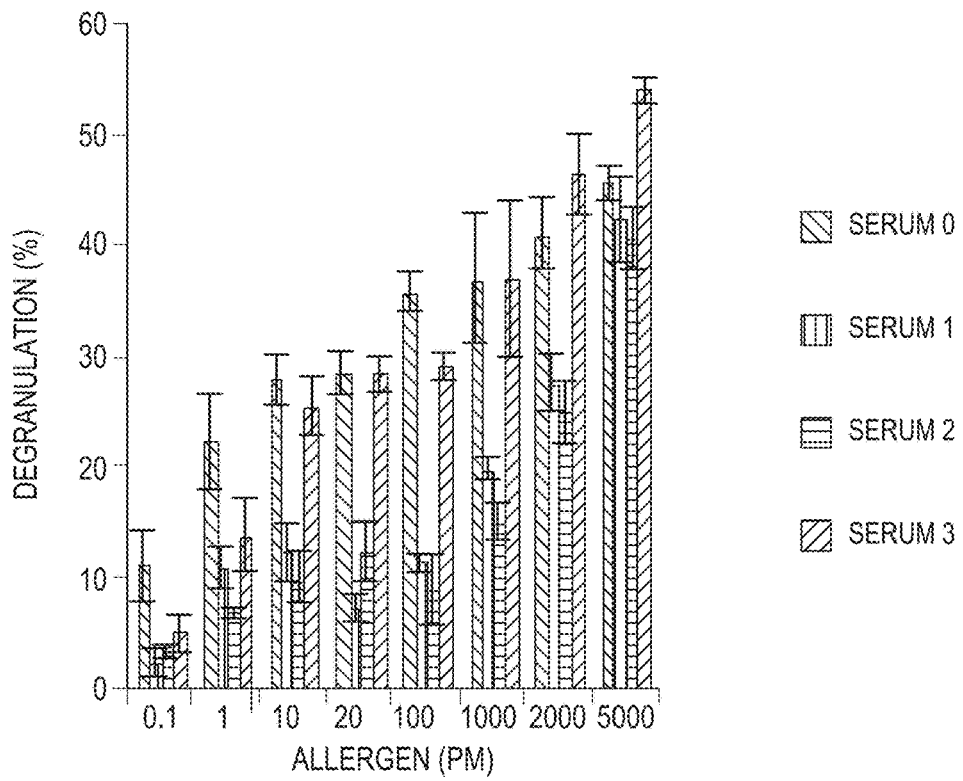
Figure 17E:
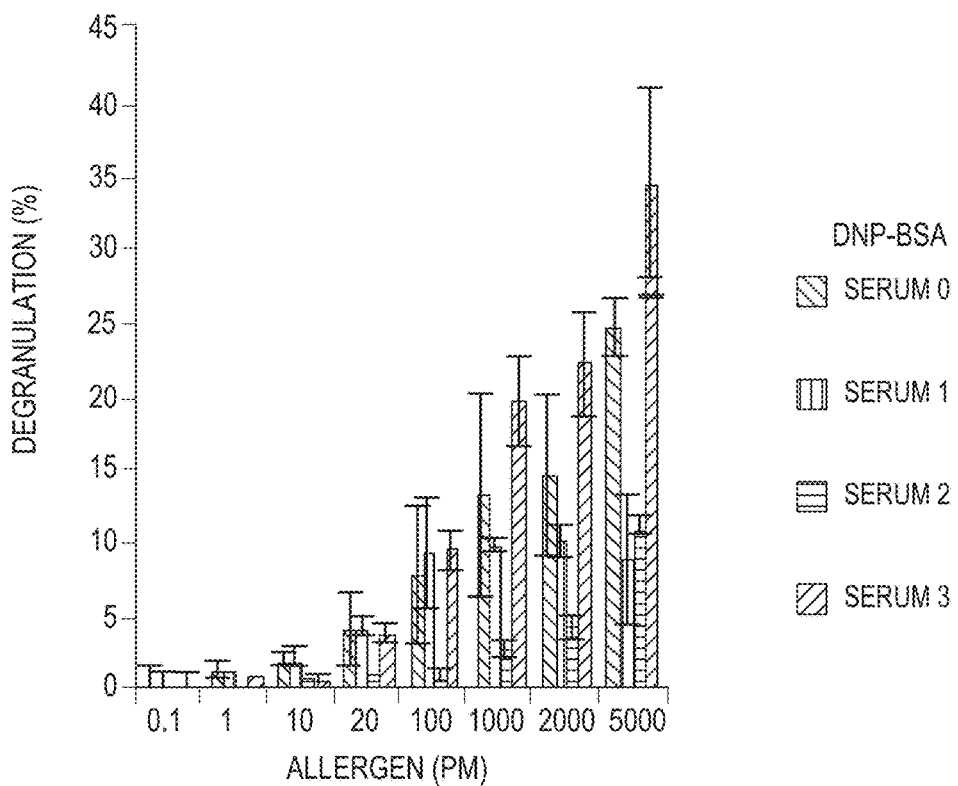
Figure 17F:
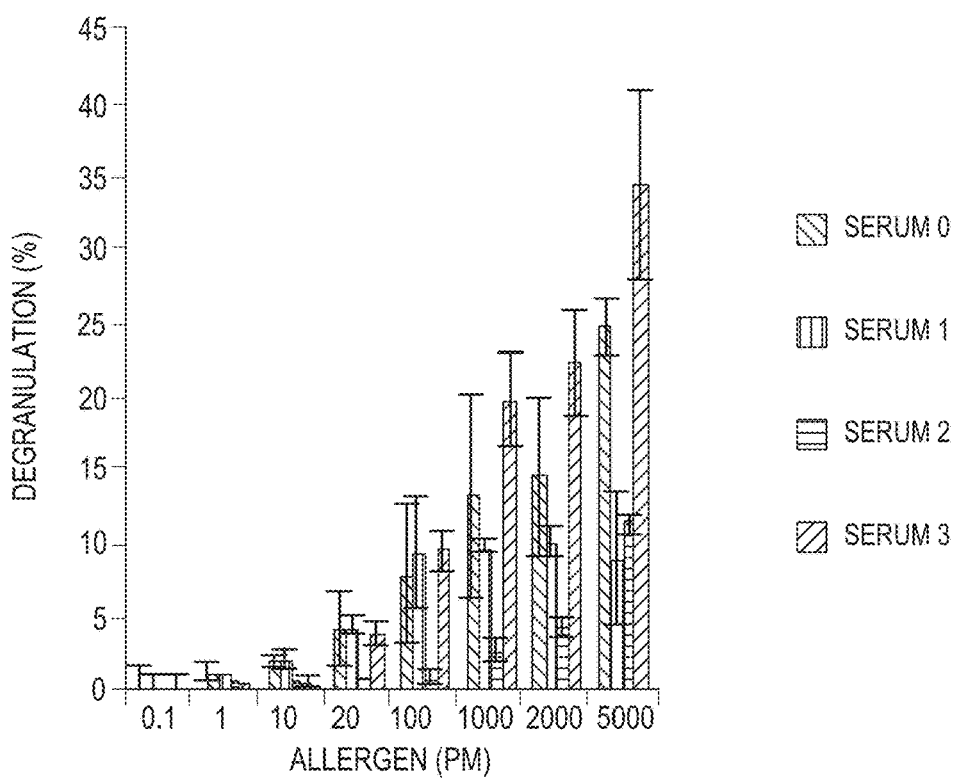
Figure 17G:
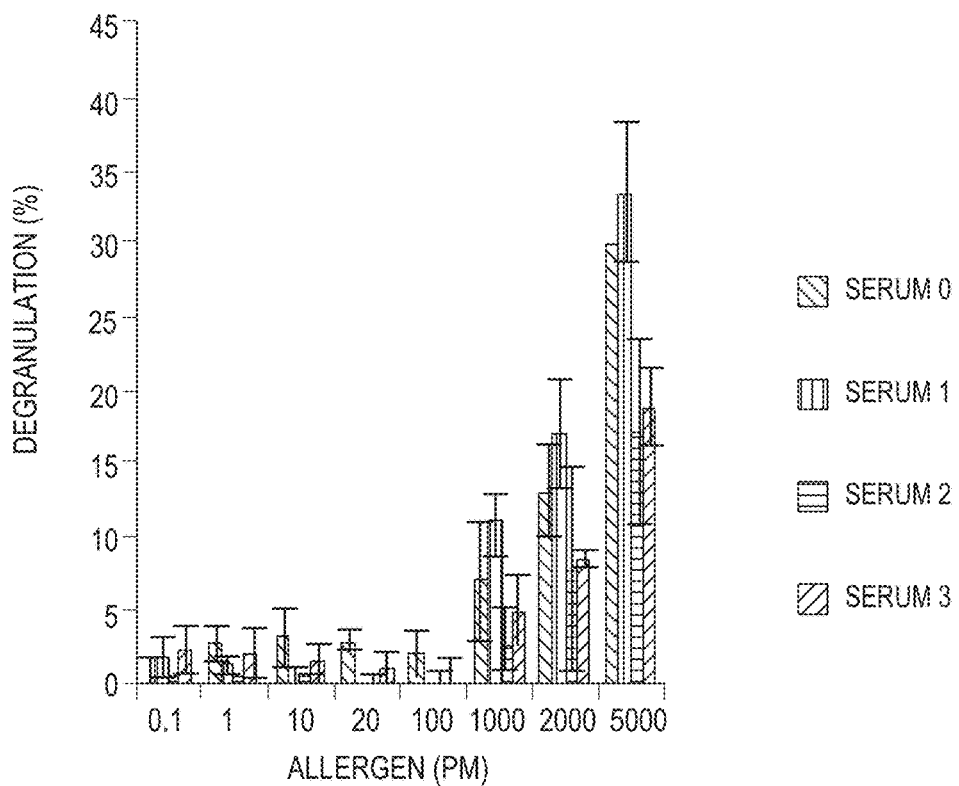
Figure 17H:
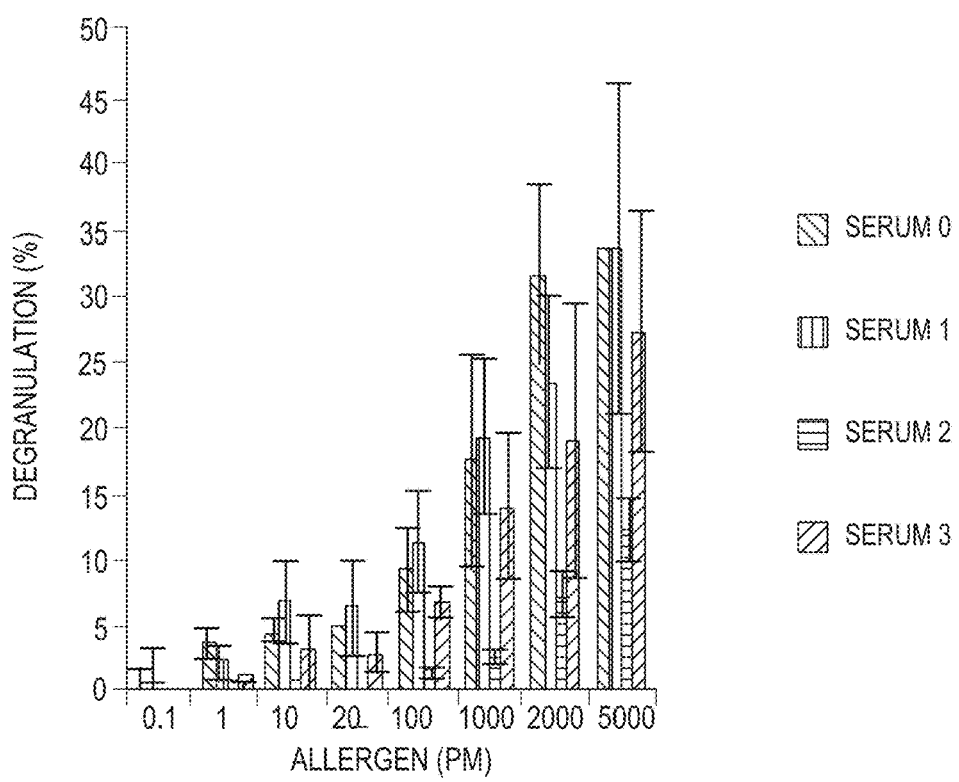
Figure 18A:
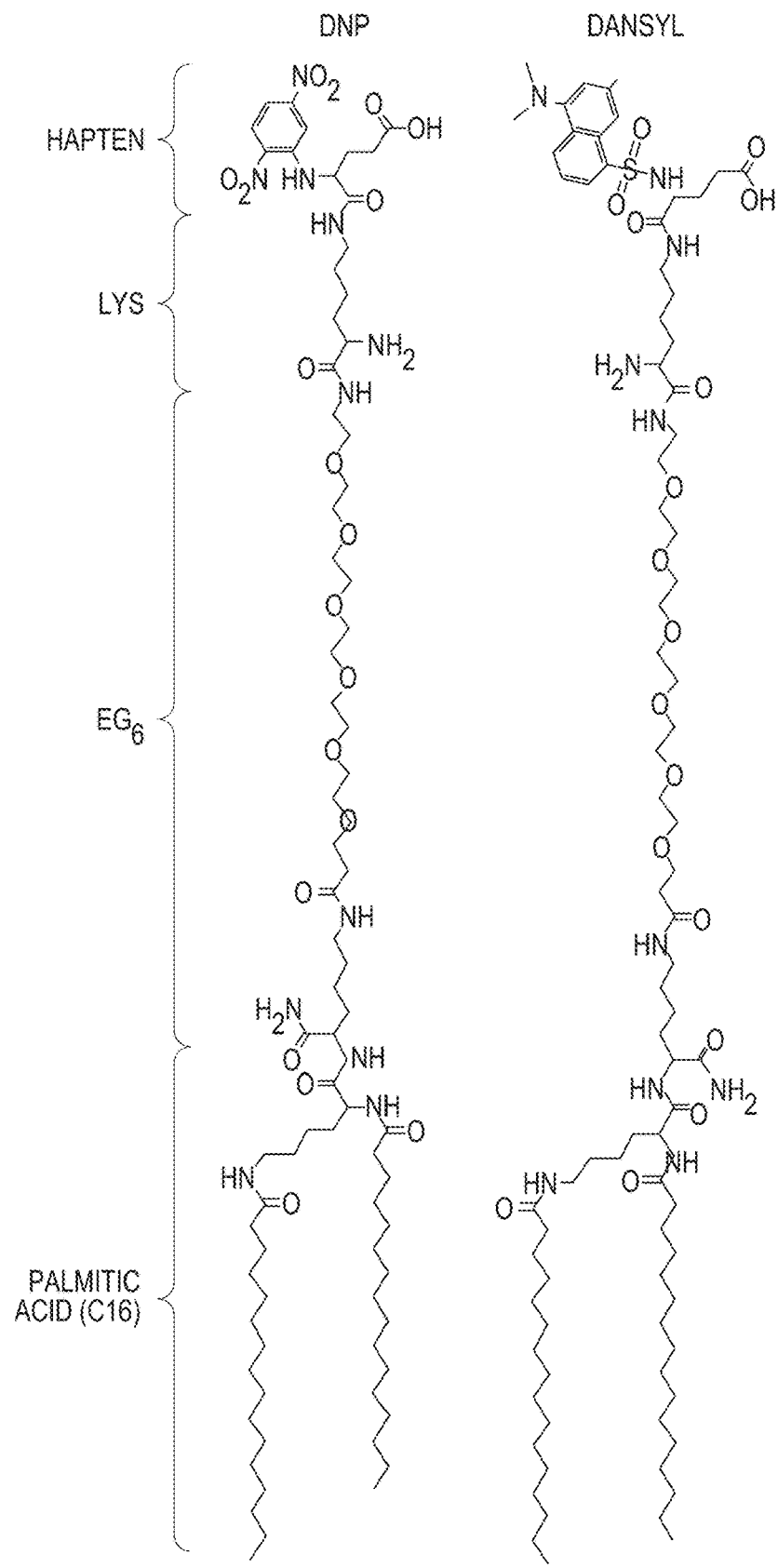
FIG. 18A-D. Nanoallergen Design and Formulation. (A) Chemical structures of Hapten-Lipid conjugates. (B) Schematic of nanoallegen liposome formulation demonstrating PEG2000 coating and haptens-lipid conjugates. Cartoons demonstrating mast cells (shown in grey) with primed FcεRI receptors with polyclonal IgE's responding to natural allergen protein (C) and mast cell degranulation induced through nanoallergen FcεRI receptor crosslinking crosslinking (D).
Figure 18B:
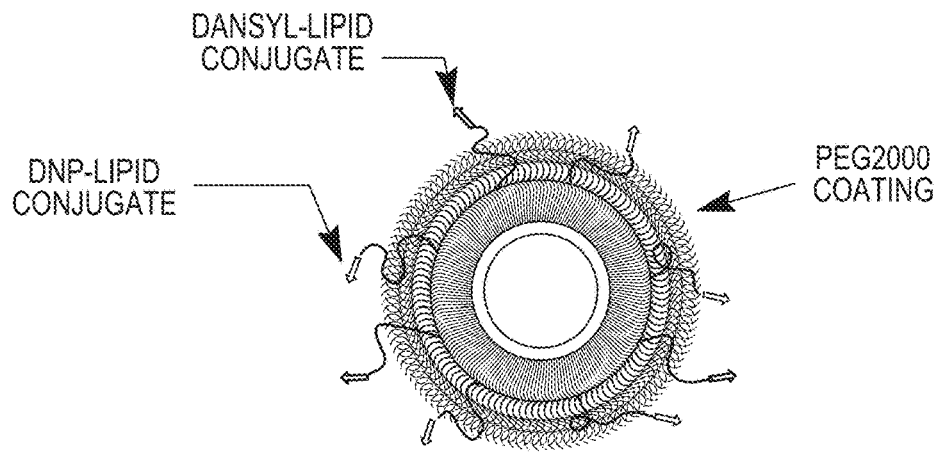
Figure 18C:
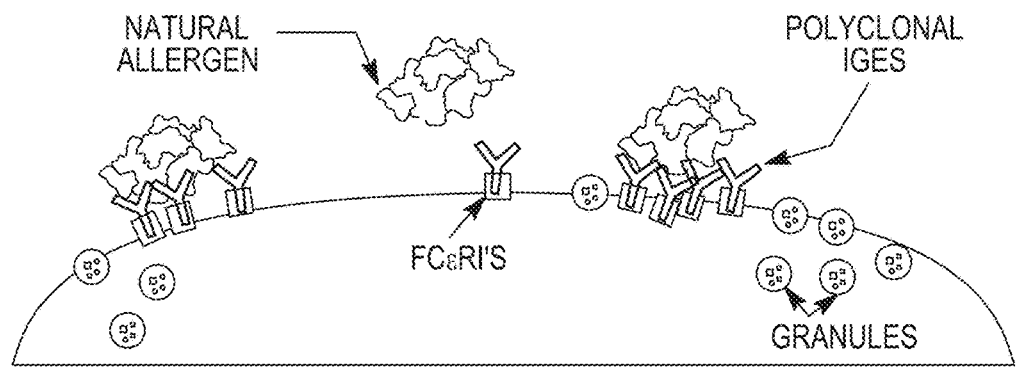
Figure 18D:
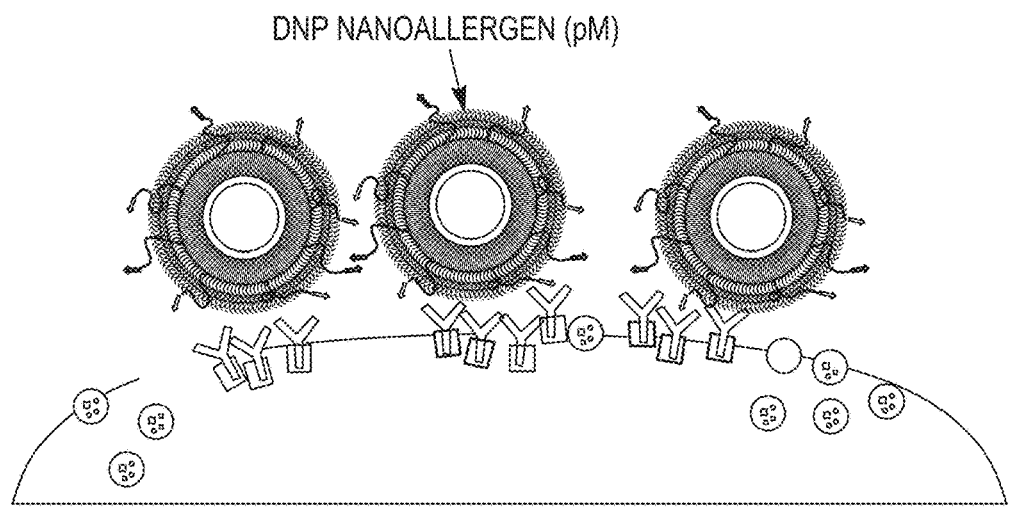

Decreasing degranulation responses at higher allergen concentrations is likely due to an increase of inhibitory cascades caused by overstimulation. Applicants performed a series of Western blots to observe increases in activating and inhibitory cascades in the presence of both Ara h 2 and nanoallergens with 2% epitope 2. Applicants observed phosphorylation of Bruton's tyrosine kinase (BTK) indicating activating signaling pathways. Applicants observed an increase in phosphorylation BTK nanoallergens, demonstrating their similar intracellular responses (FIG. 3). Applicants also confirmed the presence of both Ara h 2 and peptide 2 specific IgEs with ELISA (FIG. 11). Finally, in order to demonstrate the versatility of nanoallergens, nanoallergen size and epitope-lipid percentage were varied (FIG. 12). This demonstrates a predictable increase in degranulation response with increases in nanoallergen epitope valency.

Example 5. Nanoallergens Reveal Several Important Antigenic Epitopes of Ara h 2

Figure 4:
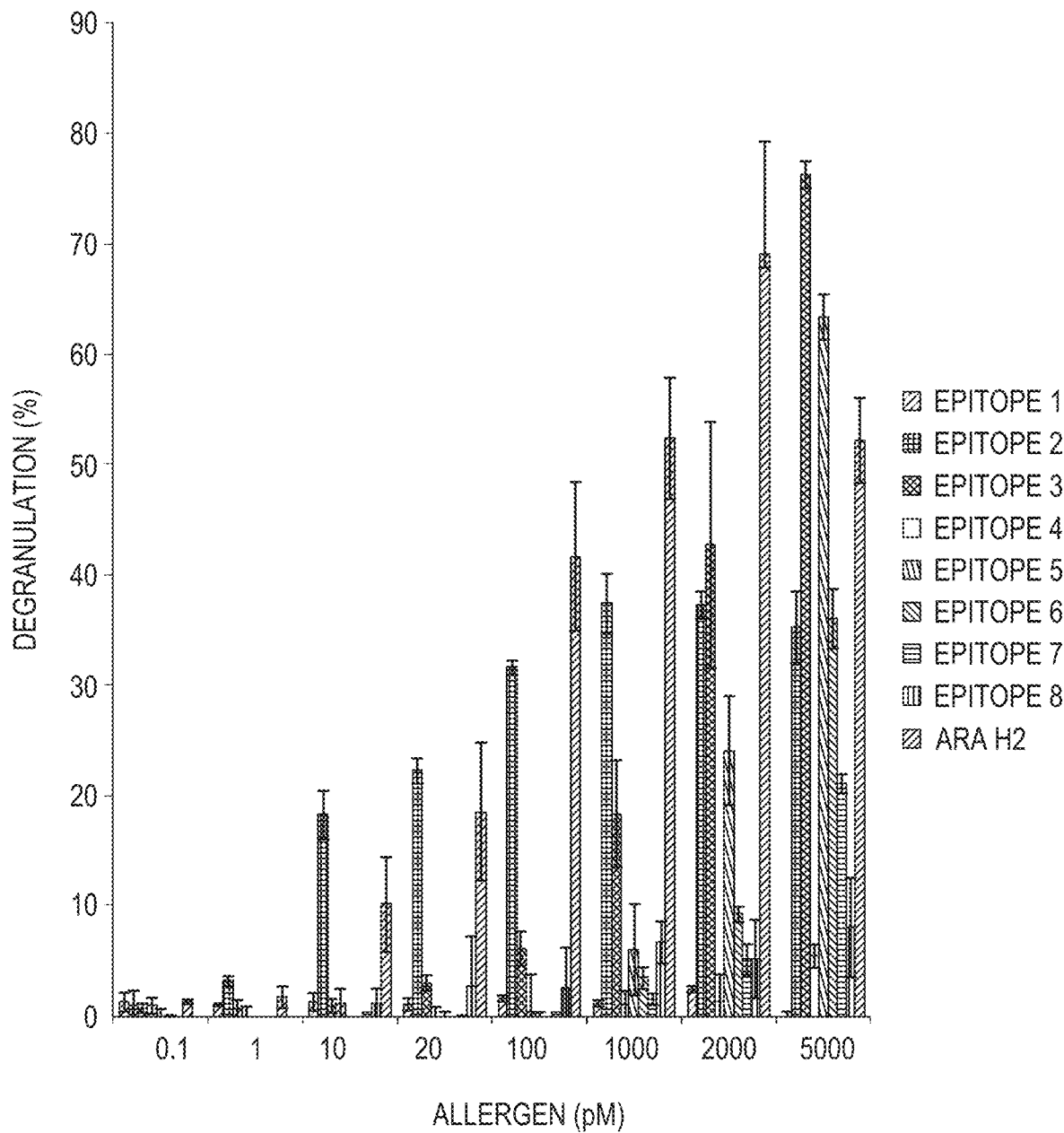
FIG. 4 illustrates that nanoallergens reveal several immunogenic epitopes on Ara h 2. Nanoallergens were loaded with 2% of each Ara h 2 IgE binding epitope-lipid conjugate and used to trigger degranulation. Note that epitope 1, 4 and 8 showed little or no degranulation response.
Figure 10:
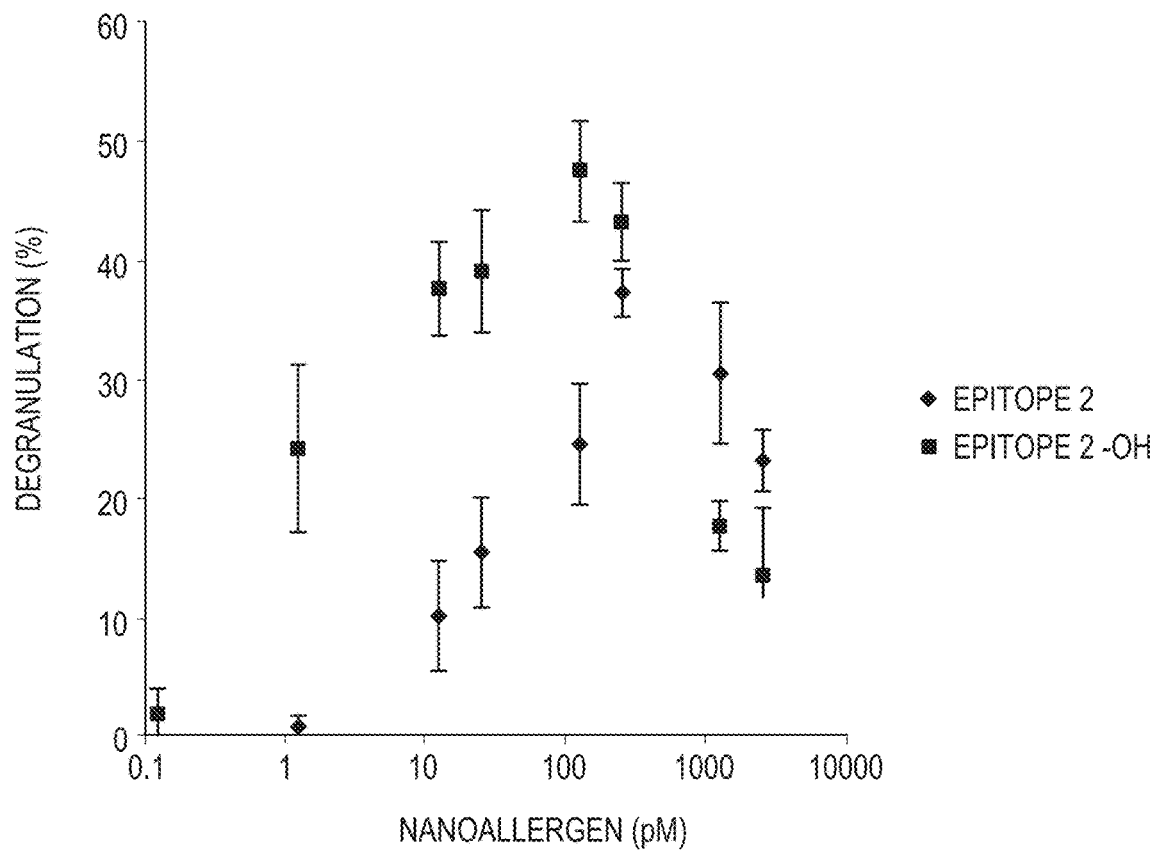
FIG. 10 illustrates epitope peptide 2 demonstrates an increase in response when proline hydroxylations are present. Epitope 2-lipid conjugate was made with and without the addition of proline hydroxylations and loaded at 2% in nanoallergens.

In addition to epitope 2 nanoallergens, applicants formed nanoallergens using all eight of the potential IgE binding epitopes. As demonstrated by FIG. 4, six of the eight epitope nanoallergens (2, 3, 4, 5, 6 and 7) simulate degranulation in a single patient serum while the remaining two epitope nanoallergens had little or no response. It is interesting to note that epitope 2 nanoallergens was able to stimulate degranulation at approximately 100 fold lower concentrations than the other immune-reactive epitope nanoallergens. The result suggests that epitope 2 has a higher monovalent affinity for its corresponding IgE than the other immune-reactive epitopes. The high degranulation response is also possibly due to two other factors. First, epitope 2 was the only epitope that had post-translational modifications in the form of proline hydroxylations. Applicants demonstrate that these hydroxylations increase the degranulation response (FIG. 10). Also, approximately 10% of all IgEs directed against Ara h 2 were specific for epitope 2, making this epitope likely the most crucial for this particular patient (FIG. 11).

Figure 5A:
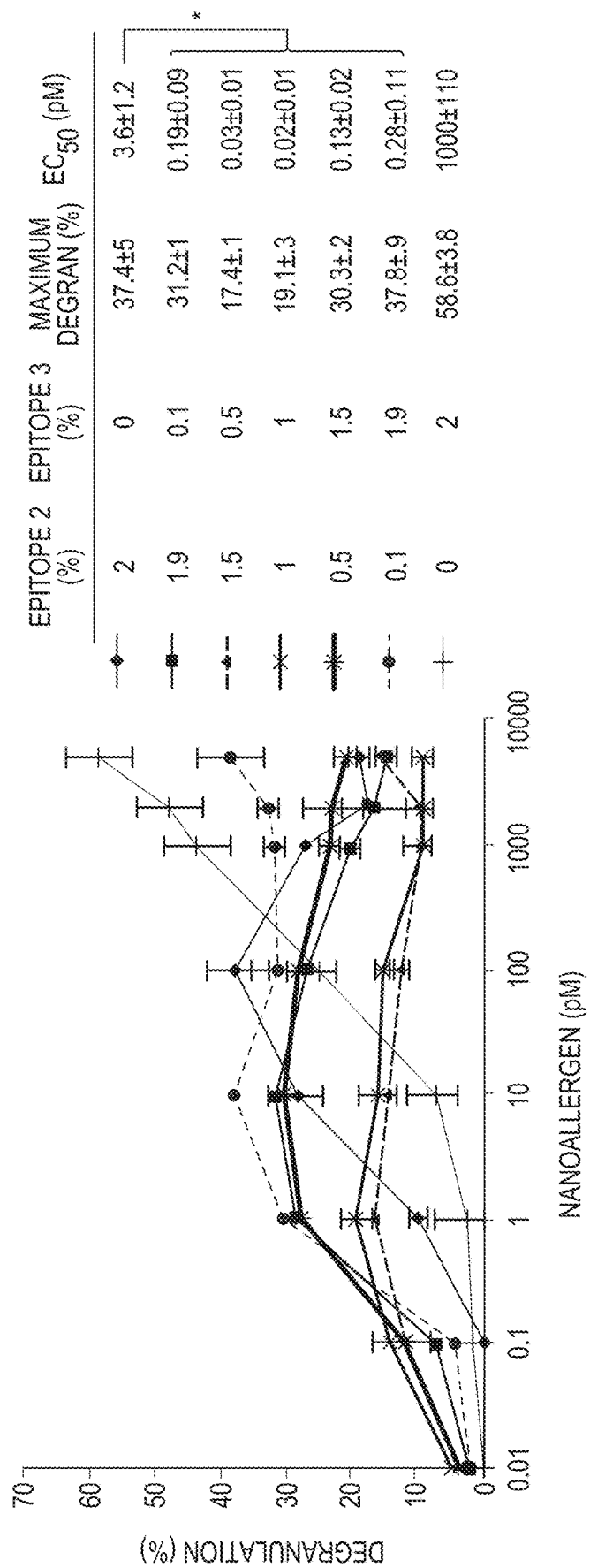
FIG. 5A-C illustrates that heterogeneous nanoallergens demonstrate crucial binding epitopes. Nanoallergens were formed at varying epitope-lipid ratios and their effects on triggering degranulation observed. In A., epitope 2 and 3 were mixed at varying ratios. In B., epitope 2, 3, 5, 6, and 7 were added one at a time while maintaining a constant total epitope-lipid loading of 2%. In C., a nanoallergen with a mixture of epitope-lipid 2, 3 and 5 was used to trigger degranulation in the presence of free epitope 2 (100 μM) or with epitope 2 lipid conjugate omitted from the formulation. Stars indicated p>0.05.

Example 6. Heterogeneous Nanoallergens Demonstrate Crucial Degranulation Inducing Epitopes Applicants formulated nanoallergens using varying ratios of several allergy epitopes while maintaining the total epitope loading at 2% of total lipid. First, applicants combined the low antigenic epitope 3 with the highly antigenic epitope 2 at various ratios and observed the results. This was done in order to simulate allergen proteins that generally possess both high and low affinity epitopes on the same protein molecule. As the ratio of high to low affinity epitope decreases, it appears to increase the degranulation response (FIG. 5A). This increase in degranulation response (demonstrated by a decrease in concentration where the maximum degranulation occurs) was also combined with a decrease in the maximum degranulation response a 1.5% and 1% epitope 2. However, this maximum value returned to the typical norm of 40% as the ratio of high to low affinity epitope continued to decrease. Interestingly, at 0.1% epitope 2, a similar response was seen to 1.9% epitope 2, demonstrating that a combination of epitopes amounted to an increase in degranulation response.

Figure 5B:
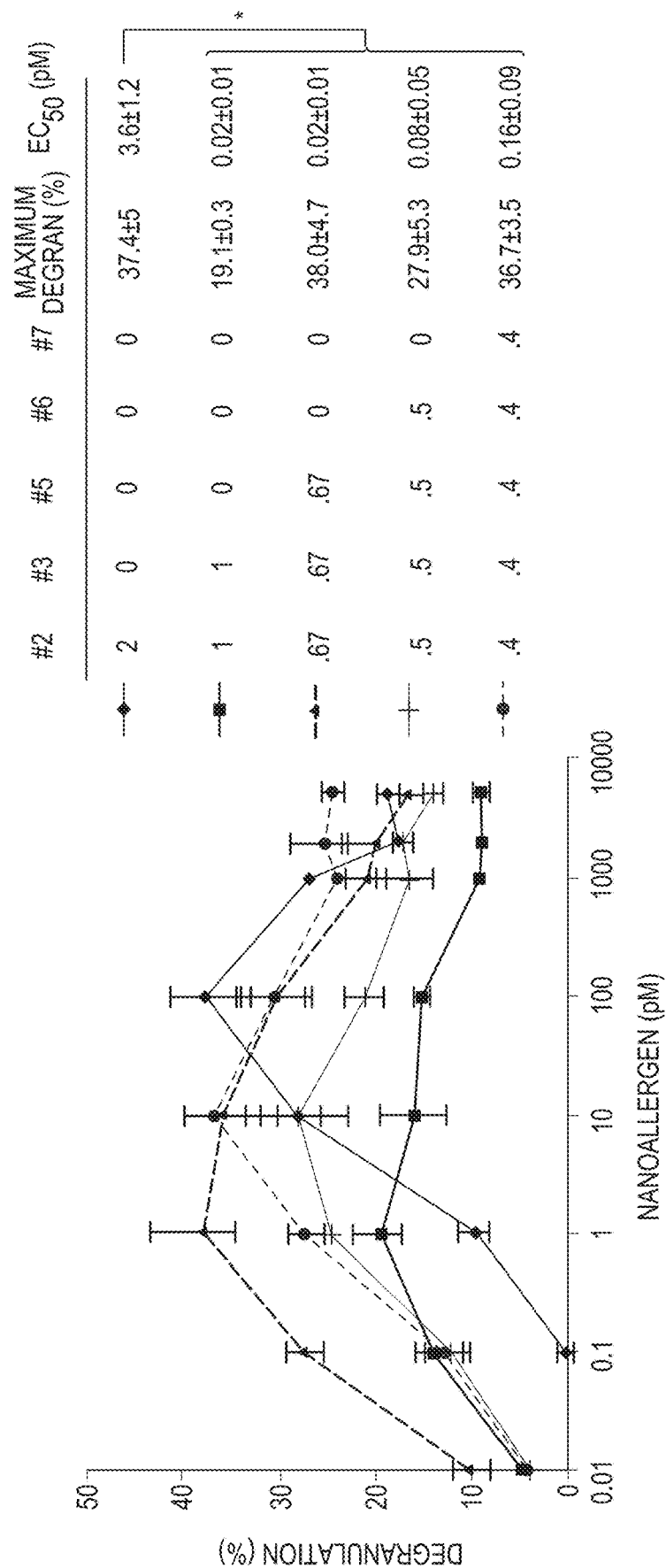

Allergens possess more than just two IgE binding epitopes on a single allergen protein. For example, Ara h2 has demonstrated up to seven IgE binding epitopes for a single clinical sample. To more accurately simulate multiple IgE binding to a single allergen protein, applicants increased the number of different epitopes on a single nanoallergen while maintaining a constant total epitope loading of 2%. Applicants decided to keep an even ratio of different epitopes in order to model the 1:1 ratio of epitopes that are present on a single allergen protein. As demonstrated by FIG. 5B, addition of new epitopes had varying effects on degranulation response. In each case, additional peptides increased RBL cell sensitivity to nanoallergens while having varying effects upon the maximum degranulation response. The data indicated that a 1:1:1 ratio of epitope 2, 3 and 5 had the most robust response, stimulating a maximum degranulation response of 37.5% at only 1 pM concentrations (FIG. 5B).

Figure 6:
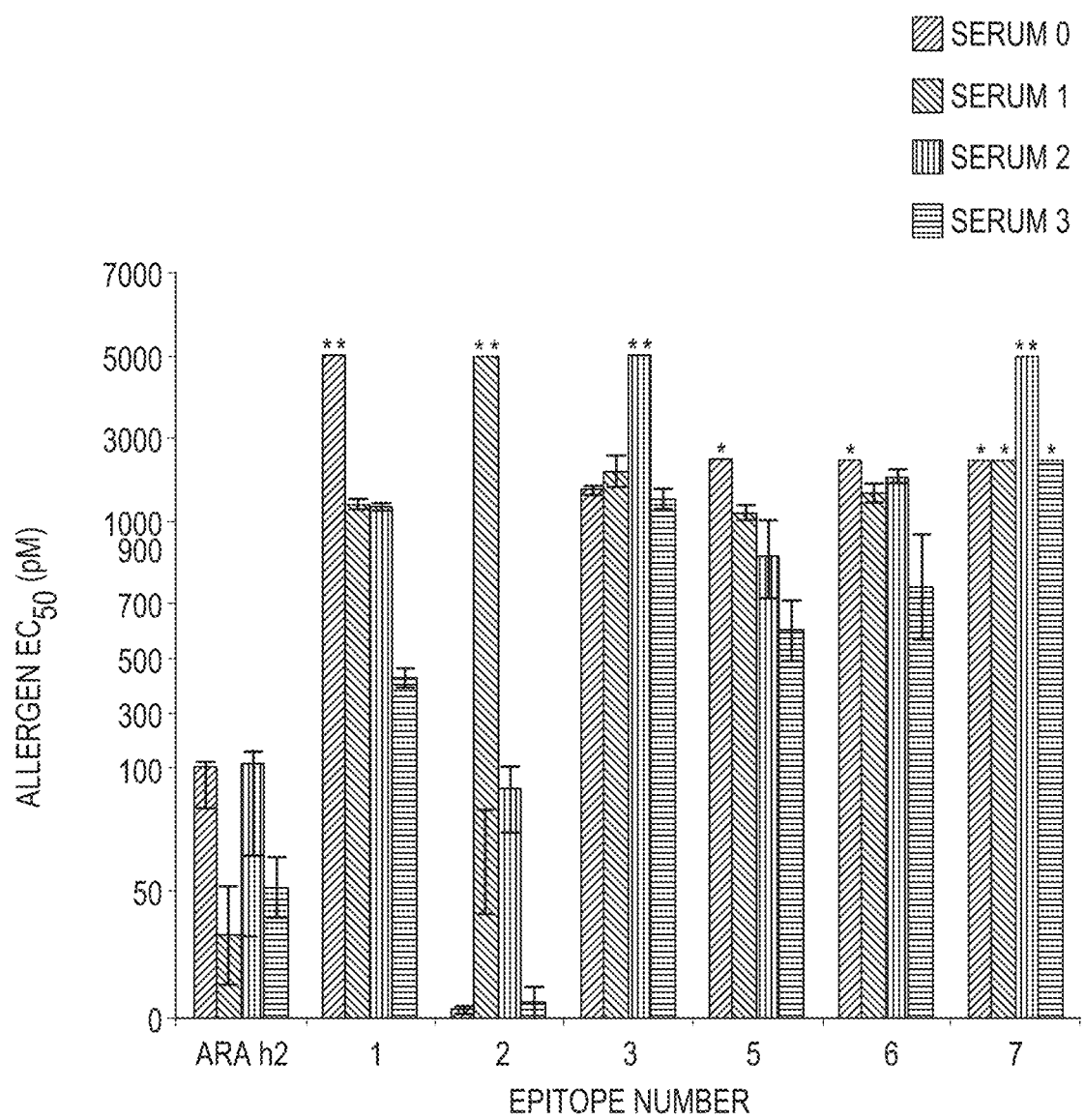
FIG. 6 illustrates that nanoallergens reveal epitopes that are crucial for several patient sera. Three additional patient sera were tested for degranulation response with 2% loaded Ara h 2 epitope-lipid conjugates. The EC50 values of the degranulation assays are shown. Note that epitope 8 did not demonstrate any degranulation in each of the patient sera. Stars indicate an EC50 values between 5000-2500 pM, double stars indicate an EC50 values >5000 pM.

Using the epitope 2, 3, 5 nanoallergens, applicants can then determine which of these epitopes is most crucial for such high degranulation responses. This high degranulation response can be evaluated by omitting an epitope from a nanoallergen formulation or co-incubating an excess of free epitope peptide to monovalently bind epitope reactive IgEs and inhibit them. Applicants omitted each epitope one by one from the formulation and observed the results. When epitope 2 was prevented from interacting with its specific IgEs either by omission or addition of free peptide, a greater than 1000-fold increase in the maximum degranulation concentration occurred (1 pM to >5000 pM, FIG. 5C). This result illustrates the importance of Ara h 2 epitope 2 for overall particle antigenicity. However, when Ara h 2 was incubated at varying concentrations with an excess (100 μM) of free epitope 2 peptide only a very small decrease in degranulation response was demonstrated (FIG. 13). This result indicates that inhibition of a single epitope on an allergen protein is not sufficient to prevent degranulation.

Example 7. Additional Clinical Samples

Given the variability of IgE binding epitopes in the clinical population, it was prudent to also test nanoallergens on additional patient serum. In light of the variability, applicants chose three additional patient serums that have both high peanut specific IgE concentrations and showed degranulation responses to Ara h 2 (Table 2, FIG. 16A). Applicants also confirmed the presence of IgE binding to both Ara h 2 and epitope 2 using ELISA (FIG. 14). Then, using the nanoallergen in vitro technique, applicants evaluated these patient seras for immunoreactivity to each Ara h 2 peptide. The patient samples showed some similar trends.

All four samples demonstrated similar moderate responses to epitope 5 and 6 and low responses to epitope 7 and no response to 4 or 8 (FIG. 6). Serum 1, 2 and 3 also demonstrated moderate responses to epitope 1 in contrast to Serum 0 (FIG. 6). Finally, the serums had the most dramatic difference in response to serum 2, ranging from no response to very high responses (FIG. 6).

TABLE 2

Listing of patient sera and the ImmunoCAP results for peanuts.

| Serum Number | Peanut IgE (kU/L) |
|---|---|
| 0 | 84.4 |
| 1 | 99.3 |
| 2 | 50 |
| 3 | 124.5 |

The studies presented herein demonstrate that nanoallergens can be effectively used in vitro with patient serum to identify immunodominant IgE binding epitopes. Nanoallergens offer more information about the immunogenicity of IgE binding epitopes than current epitope binding studies. This platform is versatile, tunable and, as this study demonstrates, can provide addition information about allergens and type I hypersensitivity-induced degranulation.

One of the most crucial aspects of nanoallergens is their ability to more directly describe the immunogenicity of an individual IgE binding epitope. By using a highly multivalent platform, nanoallergens more accurately simulate how the epitope would participate in crosslinking of FcεRI receptors. Additionally, even at 2% epitope loading and assuming half of them are confined to the inner core of the liposome, these particles would display around 800 epitopes each. The high degree of valency allows nanoallergens to overcome the decreased monovalent affinity for free peptides due to increases in conformational entropy. Therefore, nanoallergens can characterize epitopes that might not have high enough affinity to be detected with conventional binding studies such as ELISA.

The typical method for assessing IgE binding epitopes is either with a microarray or ELISA type assay for determining if binding occurs and to obtain an estimate of monovalent affinity. However, these metrics do not necessarily translate to physiological degranulation responses in vivo. One study by Osku et al. demonstrates that the estimate of affinity for an individual epitope does not necessarily correlate to clinical responses. Linear peptides not in the context of the protein are limited in that they do not demonstrate their unique contribution to the overall avidity of the allergen protein and because crosslinking reactions are inherently multivalent, this information is critical. Nanoallergens offer a more robust metric for epitope immunogenicity and even demonstrate the importance of lower affinity epitope that might be overlooked by ELISA assays. For example, in our study, epitope 3 and 5 did not demonstrate any binding through ELISA, but could trigger degranulation in a nanoallergen (FIG. 4).

More importantly, heterogeneous nanoallergens provide information about which epitopes are most crucial for trigger degranulation. By systematically removing a single epitope from a heterogeneous nanoallergen, applicants can provide a measure of how the single epitope impacts the immunogenicity of the allergen protein as a whole. The information gleaned from this data would be invaluable for future inhibitor designs. Additionally, with multiple patient seras, applicants demonstrate trends in immunogenic epitopes for Ara h 2 (FIG. 6) that can be used for future study.

Figure 5C:
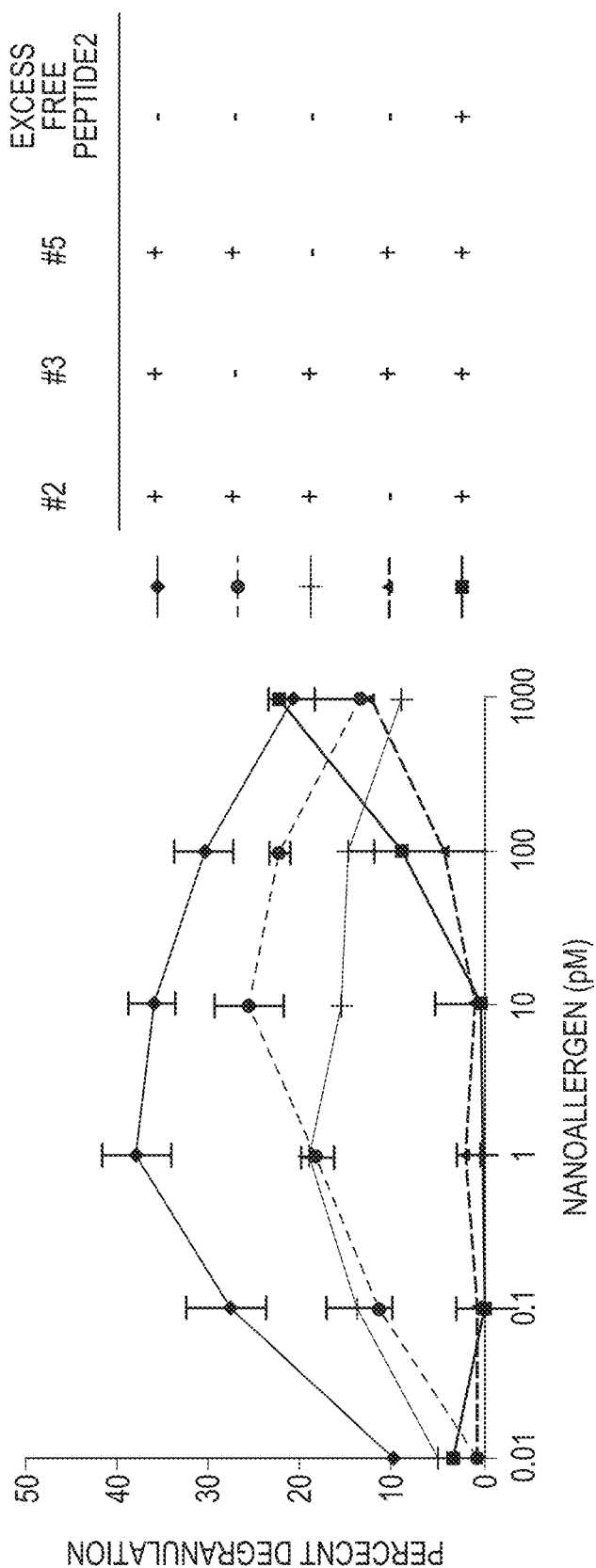

Nanoallergens can be used to also reveal new aspects of allergens and the degranulation response. Epitope 2 had a higher affinity than other epitope peptides, given that it was able to be detected binding by ELISA (FIG. 11). It was interesting to note that this was the only epitope with a post-translational proline hydroxylation. Removal of this epitope in particular greatly affected the immunogenicity of heterogeneous nanoallergens (FIG. 5C). As noted in other studies, post translationally modified IgE binding epitopes tend to have high binding affinity and are important for the overall protein immunogenic response.

Overall, nanoallergens provide important immunogenic information about potential IgE binding epitopes. Nanoallergens could even be used to screen for new potential IgE binding epitopes with greater ease than conventional binding studies. Epitope-lipid conjugates are easy to synthesize with standard peptide synthesis techniques and can rapidly be incorporated into nanoallergens allowing epitopes to be quickly characterized. Applicants also repeated this study with the second major peanut allergen protein, Ara h 6, and demonstrated the utility of nanoallergens with other allergen proteins (FIG. 17, Table 3, SEQ ID NO: 17-23). Finally, nanoallergens have the potential as epitope carries for in vivo allergen testing. This would allow patients to know not only the proteins they are allergic to but also the immunogenic epitopes.

TABLE 3

Ara h 6 Epitopes.

| Epitope # | Sequence | Number | Notes |
|---|---|---|---|
| 1 | MRRERGRGGDSSSS | 24-37 | |
| 2 | KPCEQHIMQRI | 45-55 | Homology to ara h2 epitope 11 |
| 3 | YDSYDIR | 35-68 | Similar to ara h2 epitope 2 |
| 4 | CDELNEMENTQR | 82-93 | Homology to ara h2 epitope 10 |
| 5 | CEALQQIMENQCD | 97-109 | Homology to ara h2 epitope 7 |
| 6 | KRELRMLPQQ | 120-129 | Homology to ara h2 epitope 7 |
| 7 | CNFRAPQRCDLDV | 130-142 | Homology to ara h2 epitope 8 |

Example 8. Nanoallergens: A Multivalent Platform for Studying and Evaluating

Potency of Allergen Epitopes in Cellular Degranulation Type I hypersensitivity is primarily caused by immune recognition of otherwise innocuous molecules, resulting in degranulation reactions in mast cells, releasing histamine, inflammatory cytokines, and other inflammation causing molecules into circulation.[1] Mast cell degranulation is typically triggered by the crosslinking of the high affinity immunoglobulin E receptor (FcεRI) through multivalent interactions between the allergen specific FcεRI bound immunoglobulin E (IgE) antibodies and the allergen protein.

Here, we describe a new liposome based synthetic allergen platform—nanoallergens—for stimulating degranulation responses that offer precise control over allergen characteristics such as antigen valency and epitope heterogeneity. The results of this study establish nanoallergens as a potent and versatile platform delivering reproducible outcomes that can be used to elucidate novel intricacies of allergen-IgE interactions and degranulation responses.

The biochemical interactions between allergen and IgE in degranulation responses are typically complex in nature due to multivalent binding events of allergen proteins and competing intracellular pathways. A single allergen molecule binds to multiple IgE antibodies attached to FcεRI receptors causing them to cluster on cell surface.[2-6] The crosslinking of receptors initiates an intracellular cascade that results in degranulation.[7] Until recently, most in vitro work on allergic reactions has sought to characterize the IgE-allergen binding, assuming that IgE binding affinity necessarily equates to immunogenicity.[8-11] However, clinical data does not seem to validate this assumption; multiple studies have demonstrated that there is not a direct correlation between allergen specific IgE binding affinity and clinical response to allergens.[12-15] Likewise, in our laboratory, we have demonstrated the importance of weaker affinity epitope during the degranulation response.[16,17]

This discrepancy between IgE-allergen binding affinity and clinical response is likely due to the complexities that arise both from the biological mechanisms of degranulation response and allergen protein structure. Biological factors such as intracellular inhibitory pathways, IgE clonal variability, differences in immunogenic epitope affinities and relative IgE concentrations in patients make it very difficult to directly assess allergen immunogenicity with current laboratory techniques.[13,18-21] Additionally, B-cells may or may not produce specific IgEs to individual epitopes on allergen proteins. The number of epitopes and the positions of those epitopes that have a specific IgE will be unique to each patient and drastically affect the apparent allergen protein-IgE complex affinity and therefore the degranulation response.

In cellular based allergy research, the most commonly used experimental model is a synthetic allergy system using small molecule 2,4-dinitrophenol (DNP) as the hapten, and a monoclonal anti-DNP IgE (IgE$^{DNP}$) with Rat Basophil Leukemia (RBL) cells. In order to appropriately simulate RBL cell degranulation in vitro, these DNP groups are covalently bonded to bovine serum albumin (BSA) to create a multivalent DNP-BSA allergen that can crosslink IgE$^{DNP}$ and trigger degranulation. Using similar methodology, other hapten-antibody pairs have also been used in degranulation studies. One of the more common is the small molecule dansyl chloride (dansyl).[21-23] The hapten-BSA system, while commonly used to trigger degranulation, does not accurately mimic protein allergens. Although the BSA protein has several reactive amine groups, it is difficult to control the specific number of conjugations on each individual BSA protein. Importantly, this system also does not reflect the epitope heterogeneity or the polyclonal nature of clinical IgE's hence is not an appropriate model to simulate and study a natural response.[21,24] Likewise, BSA-hapten conjugates have a limited valency (approximately 20, given the number of lysines for binding), which restricts their ability to stimulate degranulation with low affinity peptide mimetics. Given the limitations of the BSA system, a model system for accurate and reliable allergen epitope presentation is urgently needed for successful adaption of the in vitro allergy research towards clinically relevant allergen proteins.

Our laboratory has recently developed a tetravalent allergy model that can present multiple different hapten molecules on a single scaffold that can stimulate degranulation.[17,21,25-27] This design allowed control over the avidity between the allergen molecule to receptor bound IgE's. This system has been exceptionally valuable in studies of IgE-FcεRI clustering and enabled us to demonstrate the significance of weak affinity epitopes in triggering cellular degranulation.[17,27] However, we identified that this system has limited functionality with clinically relevant allergens, given that protein allergens can possess up to 12 epitopes for a single allergen molecule.[24,28] More importantly, natural allergen epitopes, when replicated as short peptide fragments, have a decreased affinity for their associated IgE and typically require a much higher valency to mimic protein allergens in stimulating degranulation at comparable concentrations.

In our laboratory, we have recently developed methods for effective display of different moieties on liposome surfaces.[29-32] The lipids comprising the liposome can be covalently linked with various bioactive molecules such as peptides or small molecules prior to liposome formation, giving precise control over molecule loading. This technique is well established for cancer targeting both in vivo and in vitro.[30,33,34] Precise control allows us to incorporate as many epitopes as necessary to form highly multivalent nanoparticles with tunable valency, heterogeneity and particle size, making liposomes ideal candidates to present immunoreactive epitopes and model allergens proteins. In this paper, we demonstrate the utility of the nanoallergens platform using DNP and dansyl nanoallergens. The nanoallergen platform is designed to provide a means to analyze additional aspects of allergens and determine which IgE/epitope interactions carry higher significance for stimulating the degranulation responses.

Materials and Methods

Materials.

N-Fmoc-amido-dPEG$_6$-acid [Fmoc is also known as fluoren-9-ylmethoxycarbony] was purchased from Quanta BioDesign. N-Fmoc-Glu(OtBu)-OH, Boc-Lys(Fmoc)-OH, Fmoc-lys(ivDde)-OH, NovaPEG Rink Amide resin, HBTU [2-(1H-benzotriazol-1-yl)-1,1,3,3-tetramethyluroniumhexafluorophosphate], Fmoc-Arg(pfb)-OH and BSA (Bovine Serum Albumin) was purchased from EMD Biosciences. IgE$^{DNP}$ (clone SPE-7), dansyl chloride, 1-Fluoro-2,4-dinitrobenzene (DNFB), DIEA (N,N-diisopropylethylamine), TFA (trifluoroacetic acid), Triisopropylsilane (TIS), hydrazine, Cholesterol, Dichloromethane, 2-proponol, ACN (acetonitrile) and piperidine were from Sigma and DMF (dimethylformamide) (>99.8%), chloroform, DiD fluorescent dye (3H-Indolium, 2-(5-(1,3-dihydro-3,3-dimethyl-1-octadecyl-2H-indol-2-ylidene)-1,3-pentadienyl)-3,3-dimethyl-1-octadecyl-, perchlorate), Minimum Essential Media was purchased from Thermo Fisher. IgE$^{dansyl}$ (clone 27-74) were purchased from BD Biosciences. DSPC (1,2-di stearoyl-sn-glycero-3-phosphocholine), DSPE-mPEG2000 (1,2-distearoyl-sn-glycero-3-phosphoethanolamine-N-[methoxy(polyethylene glycol)-2000] (ammonium salt)), membranes and all mini extruder components were purchased from Avanti Polar Lipids (Alabaster, Ala., USA). DNP-BSA conjugate was purchased from Invitrogen.

Statistical Evaluation.

Unless otherwise stated all error bars represent the standard deviation of triplicates in a single experiment. For degranulation experiments, the data is a representative experiment of several experiments; all others were a single experiment. EC$_{50}$ values and error were calculated using Origin 7 software. All p values were calculated using an unpaired student's t test.

Synthesis of Hapten-Conjugated BSA Molecules.

The BSA-dansyl was prepared as previously described.[21] Briefly, BSA at 10 mg mL$^{-1}$ in 1 mL of bicarbonate buffer (0.1 M, pH 9.0) and 100 µl of 10 mg/mL of dansyl chloride DMF were combined and incubated at room temperature for 2 hours. The conjugated BSA was purified using a 0.5 ml 10 kDa molecular mass cut-off spin concentrator (Millipore). RP-HPLC was used to determine purity on an Agilent 1200 series system using a Zorbax C8 poroshell column with a two phase, 90/10 ACN/water and water mix with a flow rate of 2 mL/min at 60° C. The gradient was 5% water to 100% ACN/water mix in 5 minutes. The dansyl-BSA (elution time 4.8 min) was estimated to be >97%. There were 18 dansyl molecules per BSA as determined by the absorbance ratio of 335 nm to 280 nm.

Synthesis and Purification of Lipid-Hapten Conjugates.

Figure 23:
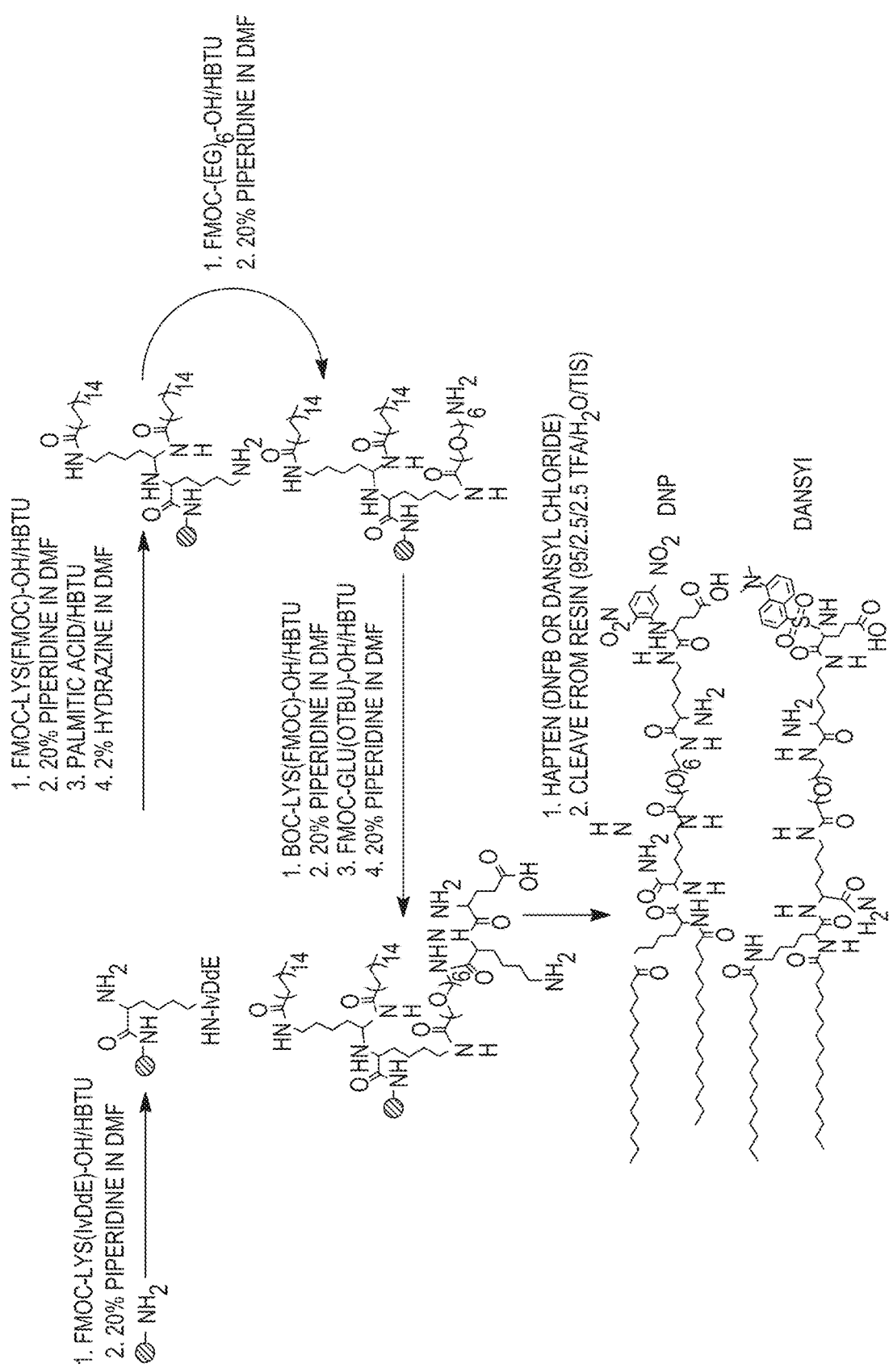
FIG. 23. Synthetic Scheme of Hapten-Lipid conjugates. DNP and Dansyl haptens were conjugated using Fmoc chemistry on a solid support.
Figure 24A:
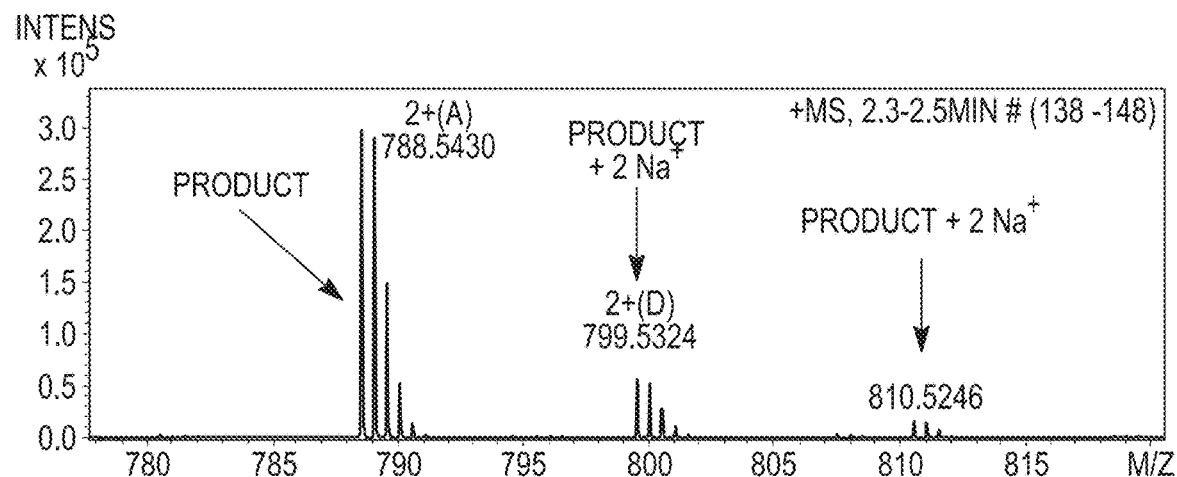
FIG. 24A-B. Mass Spectrometry analysis of Lipid-Hapten conjugates. Lipid-Dansyl product had an expected mass of 1575.06 Da and was seen in A.) with a doubly charged peak with a m/z of 1575.08. Likewise, the Lipid-DNP conjugate had an expected mass of 1508.01 Da, demonstrated in B.) with a doubly charged peak corresponding to a m/z of 1508.04. Both products also had two sodium adducts.
Figure 24B:
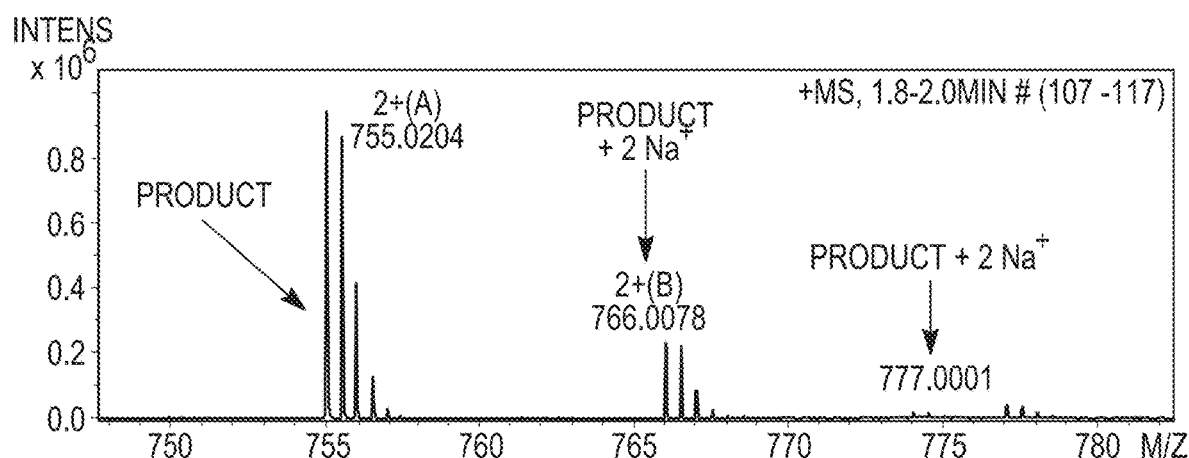
Figure 25A:
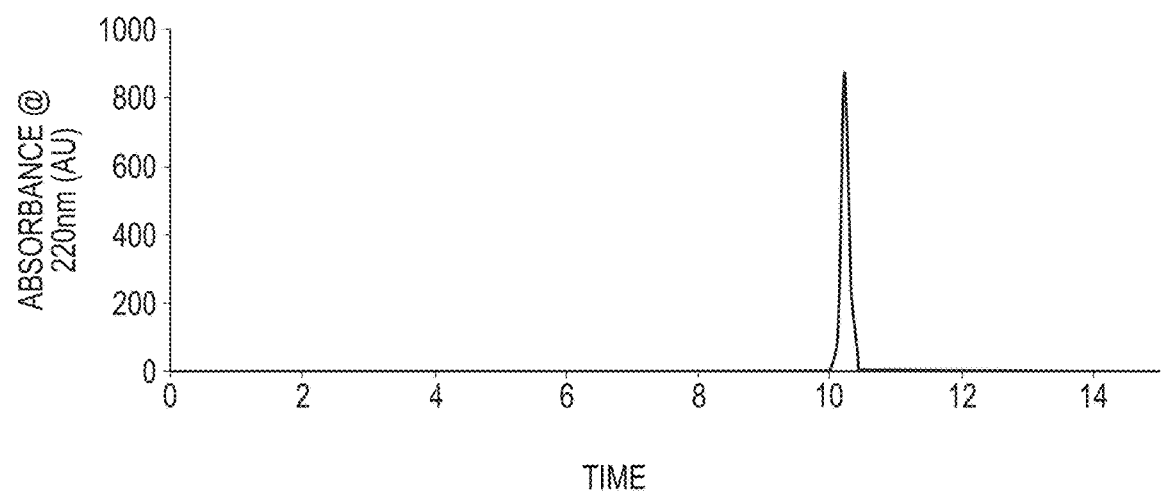
FIG. 25A-B. RP-HPLC Purity Analysis. Both molecules demonstrated >95% purity by peak area using RP-HPLC described in the methods section. The lipid-DNP conjugate (A) and lipid-dansyl (B) conjugate both showed a single peak at 220 nm at around 10 minutes.
Figure 25B:
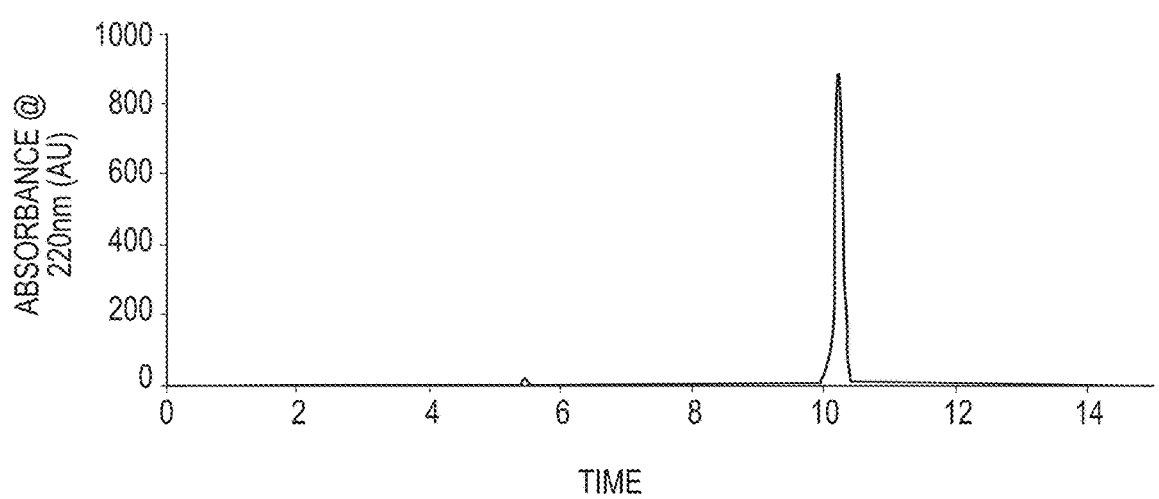

The Lipid-dansyl and Lipid-DNP conjugates were synthesized using Fmoc chemistry on solid support using NovaPEG Rink Amide resin as previously described.[21] The synthetic scheme is described in FIG. 23. Briefly, protected molecules with terminal acid groups were activated with HBTU and a four-fold molar excess of DIEA for 5 minutes and then conjugated to the resin over 30 minutes. Fmoc was deprotected with 20% piperidine in DMF and IvDdE was deprotected using 2% hydrazine in DMF. Deprotection and coupling steps were monitored with Kaiser tests. Lipid-hapten conjugates were cleaved using a 95/2.5/2.5 TFA/water/TIS solution for 45 minutes. Lipid hapten molecules were purified using 1200 Agilent RP-HPLC using a semi-preparative Zorbax C3 column. A two phase water and 70/20/10 IPA/ACN/water mix was used for purification with a gradient of 60-100% IPA mix over 10 minutes at a flow rate of 3 mL min$^{-1}$. Hapten-amino acid conjugates were purified using a Zorbax C18 column, using a two phase water/ACN system with a gradient of 20-50% ACN in 10 minutes. The product was confirmed using a Bruker microTOF II mass spectrometer (FIG. 24). Absorbance peaks at 220 nm and 280 nm were collected and verified for purity with analytical injections (>95%) (FIG. 25).

Synthesis of Hapten-BSA Conjugates.

Both DNP-BSA and dansyl-BSA conjugates were synthesized as described previously.[21]

Nanoallergen Preparation.

Liposomal nanoallergens were prepared using a procedure as previously described.[29,30] Briefly, DSPC, mPEG-2000-DSPC, Cholesterol, and Lipid-hapten conjugates were dissolved in chloroform, lyophilized, rehydrated in PBS at 60° C. and then extruded through a 200, 100, 80 or 50 nm polycarbonate filter (Avanti). For some homogeneous nanoallergens (i.e. only DNP or dansyl-lipid loaded), a lipid with an arginine head-group was added at 0.5% of total lipid to ensure particle homogeneity. This lipid followed a similar synthetic scheme as the hapten-lipid conjugates but with the addition of two arginine resides in place of hapten molecules.

Particle Characterization.

Liposomes were measured for size using DLS (Dynamic Light Scattering) analysis via the 90Plus nanoparticle size analyzer (Brookhaven Instruments Corp.), using 658 nm light observed at a fixed angle of 90° at 20° C. Liposome samples were diluted with 0.22 LM filter sterilized PBS to a 1.25 nM liposome concentration immediately after extrusion, placed in a 50 μL quartz cuvette and particle sized.

Cell Culture.

RBL-2H3 cells were cultured in Minimum Essential Media (Gibco) with 10% fetal bovine serum (Gemini Bio-Products) as previously described.[25] Degranulation Assays. RBL degranulation assays were performed as previously described, expect using nanoallergens as the allergen.[23] Additionally, RBL cells were incubated with 1 μg/mL of total IgE overnight prior to nanoallergen incubation using 75% IgE$^{cyclinA}$ as an orthogonal IgE (i.e. an IgE specific to a molecule, cyclinA, which is not used in this study) to simulate physiological conditions for all degranulation assays.[21]

Fluorescence Quenching Assay.

The binding constants for dansyl conjugates were determined as previously described.[27] Briefly, Dansyl conjugates were titrated into wells containing 15 nM IgE$^{dansyl}$ and then the fluorescence read at various concentration points (Ex=280 nm, Em=335).

Flow Cytometry.

RBL-2H3 Cells were plated in 0.5 mL wells for 6 hours then incubated with 1 μg/mL of 50%/50% IgE$^{DNP}$/IgE$^{dansyl}$ overnight. Cells were then washed with 1 mL of tyrodes buffer containing 0.05 mg/mL BSA to prevent nonspecific interactions. Nanoallergens containing 0.5% DiD were added to cells with tyrodes/BSA buffer, incubated for 5 minutes at room temperature, washed again with tyrodes/BSA buffer, quickly scrapped and analyzed with a Guava EasyCyte flow cytometer (EMD Millipore).

Kinetic Experiments.

RBL-2H3 cells were diluted 1 to 3 from a confluent plate then added into a 24 well dish and allowed to adhere to the plate overnight. The cells were then incubated with 1 μg mL$^{-1}$ of 25% IgE$^{DNP}$ using 75% IgE$^{cyclinA}$ as orthogonal IgE to simulate physiological conditions for 24 hours. Cells were then placed on ice for 1 hour, washed with ice cold Tyrode's buffer containing 0.05 mg/mL BSA to prevent nonspecific interactions. Nanoallergens were formed at 50, 100 and 200 nm containing 2% DNP hapten and 5% mPEG2000 and DiD dye added to ensure 600 dye molecules per liposome. These nanoallergens were added to the wells and incubated for 2-120 minutes, quickly washed with ice cold Tyrode's/BSA buffer, scrapped and analyzed with a Guava EasyCyte flow cytometer.

Western Blot.

RBL cells were plated at approximately 50000 cells per mL into 6 well dishes. Then the cells were washed twice with Tyrode's Buffer, incubated at 37° C. for 30 minutes. RBL cells were incubated with varying concentrations of nanoallergens containing an 85/5/5/5 DSPC/HSPC-mPEG200/DNP-Lipid/Dansyl Lipid with 50% cholesterol of total lipid added for 5 minutes at room 37° C. Following stimulation, cells were washed, scraped and placed on ice and lysed with 0.5% NP-40 and 0.5% deoxycholate in 4° C. phosphorylation solubilization buffer. Samples were normalized with a Bradford assay for total protein content and immune-precipitated using agarose conjugated monoclonal anti-SHIP antibody (P1C1) from Santa Cruz Biotechnology with three subsequent washing steps with phosphorylation buffer containing 0.5% NP-40. Cell lysates were then analyzed with a western blot using anti-p-Tyr antibody (PY99) or free anti-SHIP antibody (P1C1) from Santa Cruz Biotechnology as previously described.[35]

Results

Nanoallergen Design.

In the design of nanoallergens we used a liposomal functional group display platform that was developed in our laboratory, where the ligands are covalently attached to lipids using appropriate linkers and then purified and characterized prior to incorporating into the liposome formation.[29,30] The two most commonly used haptens in modeling allergy systems are DNP and dansyl, due to their differing monovalent affinities and commercially available specific IgE clones. Anti-DNP IgE (IgE$^{DNP}$) has a stronger affinity for DNP than anti-dansyl IgE (IgE$^{dansyl}$) has for dansyl ($K_d^{DNP}$=15 nM; $K_d^{dansyl}$=147 nM), making them an excellent pair to study for the effects of varying epitope affinities, and thus making the system physiologically relevant (Table 8-1).[17,21,25,36]

TABLE 8-1

Nanoallergen Particle Sizing. The particle sizes of 2% loaded DNP and dansyl nanoallergens were determined using DLS analysis. Different pore sizes on extrusion filters created particles of varying size.

| Liposome | Average Diameter (nm) (2% DNP) | Average Diameter (nm) (2% Dansyl) |
|---|---|---|
| 50 nm | 57.1 ± 0.2 | 57.4 ± 0.2 |
| 80 nm | 89.3 ± 2.8 | 88.4 ± 1.1 |
| 100 nm | 110.1 ± 1.4 | 113.5 ± 1.2 |
| 200 nm | 180.5 ± 1.1 | 175.8 ± 0.7 |

In order to facilitate hapten presentation on the liposome surface, hapten-lipid conjugates were synthesized using a similar approach previously developed in our laboratory (FIG. 18).[21,29,30] The hapten conjugates varied from 0.01-10% of total lipid while the remainder of the liposomes consisted of DSPC (Table 8-2).

TABLE 8-2

Homologous particle characterization. Liposomal area was estimated assuming a sphere and the total number of lipids calculated. The hapten spacing was calculated from the hapten density assuming the haptens are evenly spaced on a hexagonal grid.

| Diameter nm | DNP-Lipid (%) | Dansyl-Lipid (%) | Liposome Area nm2 | Number of Lipid/Liposome | Total Haptens (Est*) | Hapten Density (nm$^2$/hapten) | Hapten Spacing (nm) | EC$_{50}$ pM |
|---|---|---|---|---|---|---|---|---|
| 50 | 2 | 0 | 7850 | 18142.5 | 181.4 | 43.3 | 8.2 | 2790 ± 670 |
| 80 | 2 | 0 | 20096 | 50002.5 | 500.0 | 40.2 | 7.9 | 1000 ± 138 |
| 100 | 2 | 0 | 31400 | 80092.5 | 800.9 | 39.2 | 7.8 | 10.9 ± 2 |
| 200 | 2 | 0 | 125600 | 336742.5 | 3367.4 | 37.3 | 7.6 | 59.9 ± 11.9 |
| 50 | 0 | 2 | 7850 | 18142.5 | 181.4 | 43.3 | 3.2 | 5580 ± 380 |
| 80 | 0 | 2 | 20096 | 50002.5 | 500.0 | 40.2 | 7.9 | 1140 ± 98 |
| 100 | 0 | 2 | 31400 | 80092.5 | 800.9 | 39.2 | 7.8 | 279 ± 108 |
| 200 | 0 | 2 | 125600 | 336742.5 | 3367.4 | 37.3 | 7.6 | 337 ± 115 |

TABLE 8-2-continued

Homologous particle characterization. Liposomal area was estimated assuming a sphere and the total number of lipids calculated. The hapten spacing was calculated from the hapten density assuming the haptens are evenly spaced on a hexagonal grid.

| Diameter nm | DNP-Lipid (%) | Dansyl-Lipid (%) | Liposome Area nm2 | Number of Lipid/Liposome | Total Haptens (Est*) | Hapten Density (nm$^2$/hapten) | Hapten Spacing (nm) | EC$_{50}$ pM |
|---|---|---|---|---|---|---|---|---|
| 100 | 0.01 | 0 | 31400 | 80092.5 | 4.0 | 7840.9 | 109.9 | 354 ± 70.1 |
| 100 | 0.1 | 0 | 31400 | 80092.5 | 40.0 | 784.1 | 34.7 | 267 ± 40 |
| 100 | 1 | 0 | 31400 | 80092.5 | 400.5 | 78.4 | 11.0 | 222 ± 41.4 |
| 100 | 5 | 0 | 31400 | 80092.5 | 2002.3 | 15.7 | 4.9 | 27.4 ± 5.24 |
| 100 | 10 | 0 | 31400 | 80092.5 | 4004.6 | 7.8 | 3.5 | 162 ± 25.8 |
| 100 | 0 | 0.01 | 31400 | 80092.5 | 4.0 | 7840.9 | 109.9 | 2490 ± 78.3 |
| 100 | 0 | 0.1 | 31400 | 80092.5 | 40.0 | 784.1 | 34.7 | 1250 ± 27.7 |
| 100 | 0 | 1 | 31400 | 80092.5 | 400.5 | 78.4 | 11.0 | 1140 ± 110 |
| 100 | 0 | 5 | 31400 | 80092.5 | 2002.3 | 15.7 | 4.9 | 324 ± 42 |
| 100 | 0 | 10 | 31400 | 80092.5 | 4004.6 | 7.8 | 3.5 | 354 ± 35.4 |

For most studies, the nanoallergens consisted of 2% lipid-hapten conjugate unless otherwise specified. Liposomes of 50, 80, 100 and 200 nm diameters were prepared using extrusion methods, and unless otherwise stated, 100 nm diameter particles were used for most studies. We confirmed the particle sizes by Dynamic Light Scattering analysis (Table 8-3).

TABLE 8-3

EC$_{50}$ values and maximums of heterogeneous nanoallergens.

| Antibody | | | Percent Lipid-Hapten Loading (DNP/Dansyl) | | | | | |
|---|---|---|---|---|---|---|---|---|
| | Ratio | | 0/2 | | 0.1/0.9 | | 1/1 | |
| Cyclin A | DNP | Dansyl | EC$_{50}$ | Max | EC$_{50}$ | Max | EC$_{50}$ | Max |
| 75 | 0 | 25 | 280 ± 100 | 20.7 ± 2.38 | 430 ± 90 | 29.5 ± 1.9 | 1600 ± 200 | |
| 75 | 1 | 24 | 440 ± 150 | 18.0 ± 1.9 | 750 ± 120 | 25.7 ± 1.4 | 1450 ± 130 | |
| 75 | 5 | 20 | 670 ± 200 | 20.6 ± 2.6 | 620 ± 55 | 30.6 ± 0.9 | 1180 ± 420 | |
| 75 | 12.5 | 12.5 | 310 ± 80 | 20.3 ± 1.9 | 600 ± 50 | 44.1 ± 3.0 | 365 ± 100 | |
| 75 | 20 | 5 | 700 ± 100 | 11.7 ± 1.1 | 1040 ± 190 | 28.3 ± 2.1 | 1120 ± 210 | |
| 75 | 24 | 1 | 1470 ± 1150 | 11.5 ± 0.6 | 1230 ± 170 | 28.9 ± 2.1 | 1600 ± 310 | |
| 75 | 25 | 0 | >6250 | N/A | 720 ± 140 | 30.5 ± 2.1 | 970 ± 150 | |

| Antibody | | | Percent Lipid-Hapten Loading (DNP/Dansyl) | | | | |
|---|---|---|---|---|---|---|---|
| | Ratio | | | 1.9/0.1 | | 2/0 | |
| Cyclin A | DNP | Dansyl | Max | EC$_{50}$ | Max | EC$_{50}$ | Max |
| 75 | 0 | 25 | 14.8 ± 1.5 | >6250 | N/A | >6250 | N/A |
| 75 | 1 | 24 | 14.3 ± 1.5 | 1280 ± 170 | 19 ± 1.4 | 1200 ± 600 | 13.1 ± 1.7 |
| 75 | 5 | 20 | 24.8 ± 3.3 | 1300 ± 250 | 36 ± 3.3 | 110 ± 53 | 28.7 ± 2.7 |
| 75 | 12.5 | 12.5 | 28.5 ± 2.3 | 160 ± 42 | 30.5 ± 1.9 | 39.5 ± 8.4 | 29.1 ± 1.2 |
| 75 | 20 | 5 | 39.8 ± 2.4 | 560 ± 160 | 37.8 ± 6.6 | 74.0 ± 20 | 36.6 ± 2.3 |
| 75 | 24 | 1 | 40.8 ± 3.8 | 270 ± 120 | 40.2 ± 3.9 | 24.5 ± 4.7 | 35.6 ± 1.2 |
| 75 | 25 | 0 | 44.7 ± 2.3 | 180 ± 19 | 41.1 ± 1.2 | 18.4 ± 4.2 | 40.1 ± 1.8 |

Nanoallergens Trigger Degranulation Using Single Haptens.

Figure 19A:
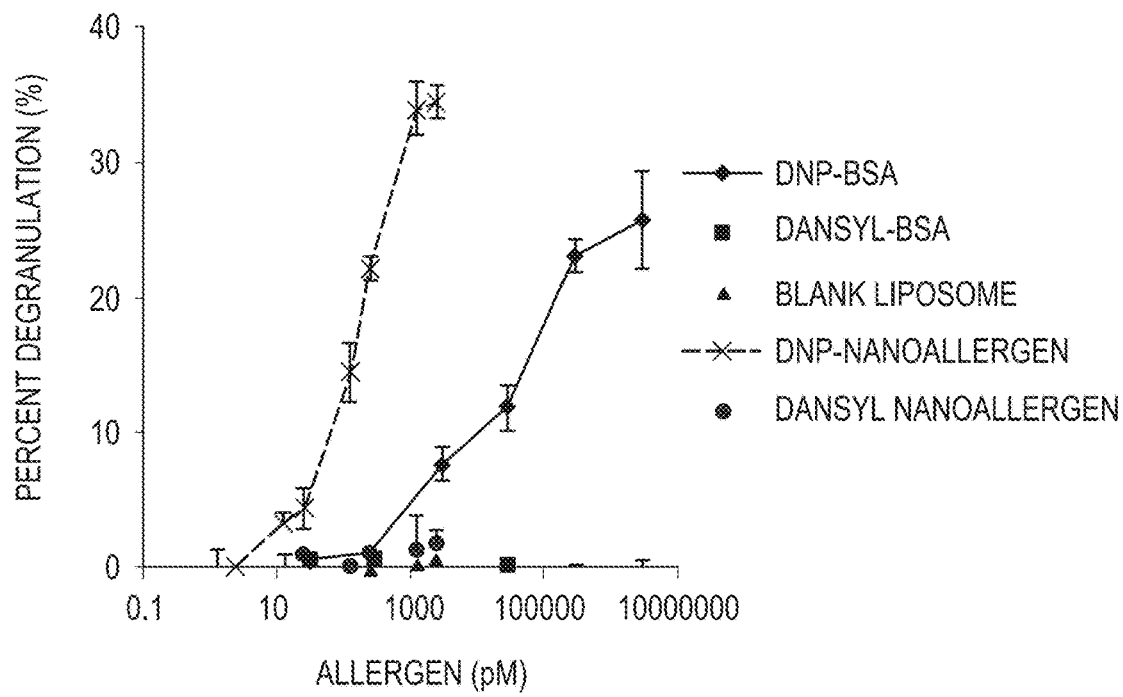
FIG. 19A-E. Nanoallergens stimulate degranulation in RBL-2H3 cells. RBL cells primed with 25% IgE$^{DNP}$ (A) or IgE$^{Dansyl}$ (B) and 75% orthogonal IgE$^{CyclinA}$ demonstrate degranulation responses similar to BSA-Hapten conjugates. Flow cytometry (C) demonstrates specific binding to RBL cells primed with 50%/50% IgE$^{DNP}$/IgE$^{Dansyl}$ to 2% hapten loaded Nanoallergens at varying Nanoallergen concentrations. D.) Cells were overstimulated with Nanoallergens loaded with 5% DNP, 5% Dansyl and 50% cholesterol to achieve overstimulation. (E) Western blots demonstrating phosphylated SHIP-1 protein and total SHIP protein using the same stimulation conditions as the degranulation assay in part (D). RFU represents relative fluorescence units.
Figure 19B:
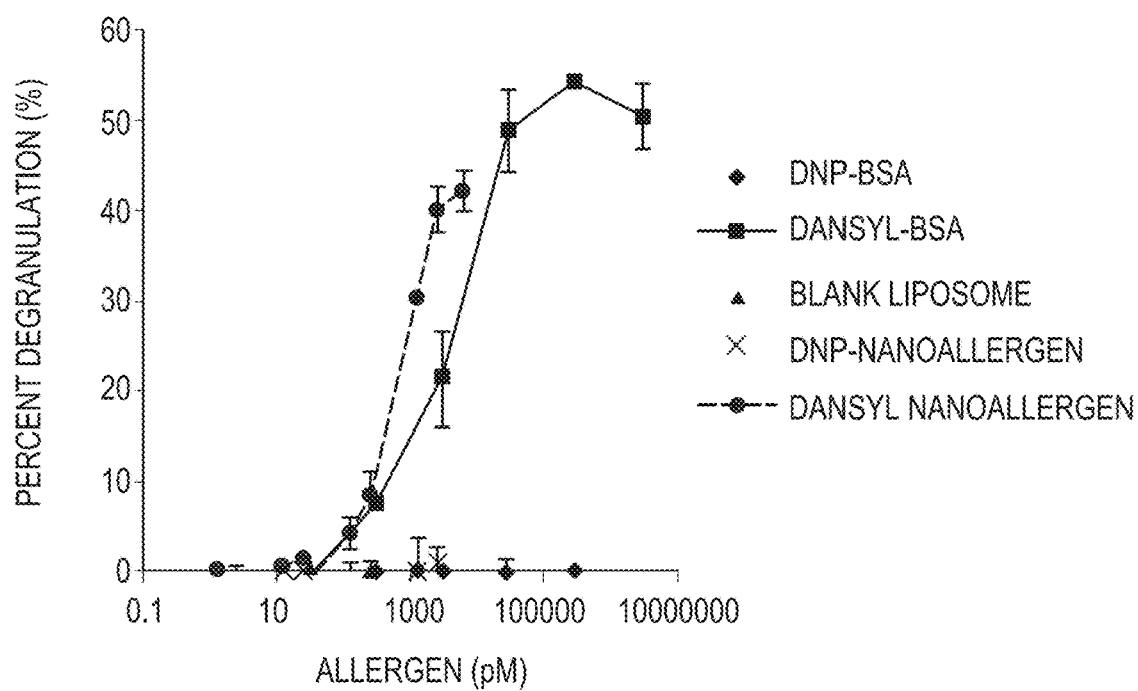

We first evaluated the ability of a single hapten system to trigger degranulation using RBL-2H3 cells primed with either IgE$^{DNP}$ or IgE$^{dansyl}$ by using either DNP-lipid or dansyl-lipid loaded liposomes. Both DNP and dansyl presenting nanoallergens stimulated similar degranulation response to the hapten-BSA conjugated allergen at a 100 and 10 fold lower concentrations respectively demonstrating the higher potency of the platform (FIG. 19A, 19B). Furthermore, any cross-reactions with liposomes without hapten-lipid conjugates (Blank) or cells primed with the other hapten specific IgE was not detected. This confirmed nanoallergen specificity, and that the intensity of response was dependent on nanoallergen concentration. The nanoallergens presented a similar response curve to hapten-BSA conjugates and common protein allergen molecules, indicating that they triggered the degranulation response in a similar manner.

Figure 19C:
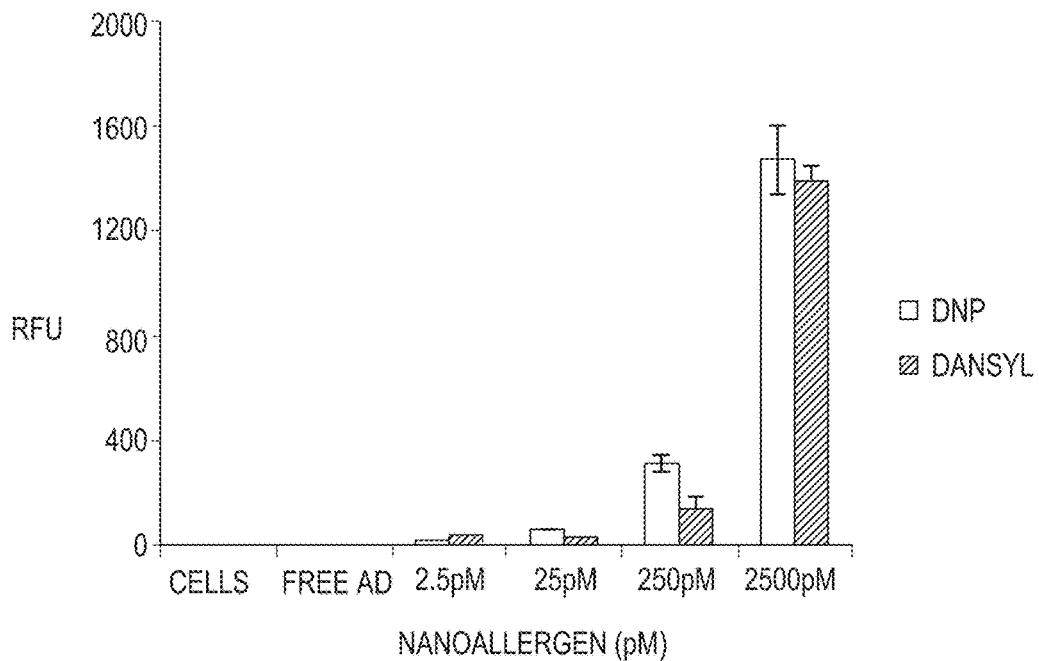

To confirm that the nanoallergens were binding specifically only to those RBL cells that present the corresponding IgEs on their surface prior to initiating degranulation, we performed flow cytometry experiments. Our results indicated that both dansyl and DNP nanoallergens demonstrated specific binding to RBL cells only primed with the analogous hapten specific IgE (FIG. 19C). The nanoallergens demonstrated a tapering of response at high concentrations. This was likely due to supraoptimal concentrations of the allergen causing excess IgE crosslinking and stimulating intracellular inhibitory pathways.[16] In order to confirm the activation of inhibitory pathways when the degranulation response plateaued, we concurrently performed a degranulation assay and a western blot with a nanoallergen loaded with both haptens, 5% DNP and 5% dansyl, to observe the expression of SHIP-1 protein during degranulation (FIG.

19D, 19E). SHIP-1 was phosphorylated when a supraoptimal concentration of allergen caused overstimulation and activation of intracellular inhibitory pathways.[35] During the plateau of degranulation response, we demonstrated that SHIP-1 protein was phosphorylated, indicating the activation of intracellular inhibitory pathways.

Nanoallergen Particle Size and Loading Affects Degranulation Response.

Figure 20A:
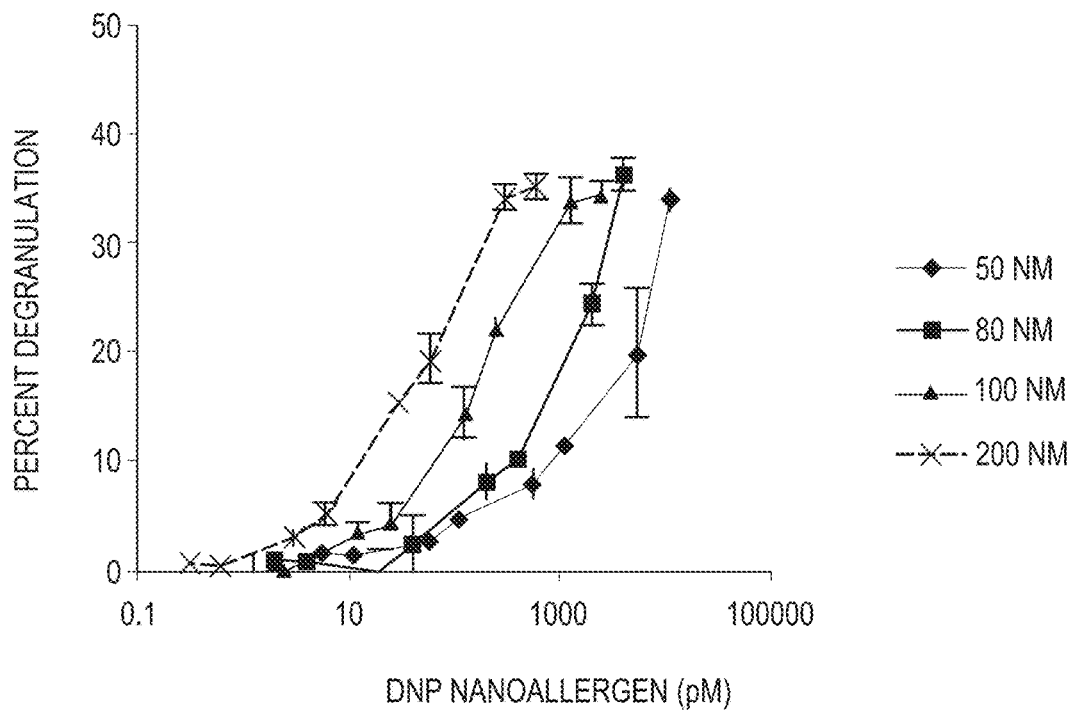
FIG. 20A-D. Nanoallergen formulations varying with particle size (50, 80, 100, 200 nm) and hapten loading (0.01, 0.1, 1, 2, 5 and 10% of total lipid) affect degranulation response. Nanoallergen particle sizes alter the degranulation response for a DNP Nanoallergen (A.) and Dansyl Nanoallergen (C.) at 2% hapten loading. Variation in degranulation response is seen in both DNP (B.) and Dansyl (D.) Nanoallergens when hapten loading is varied on a 100 nm particle.
Figure 20B:
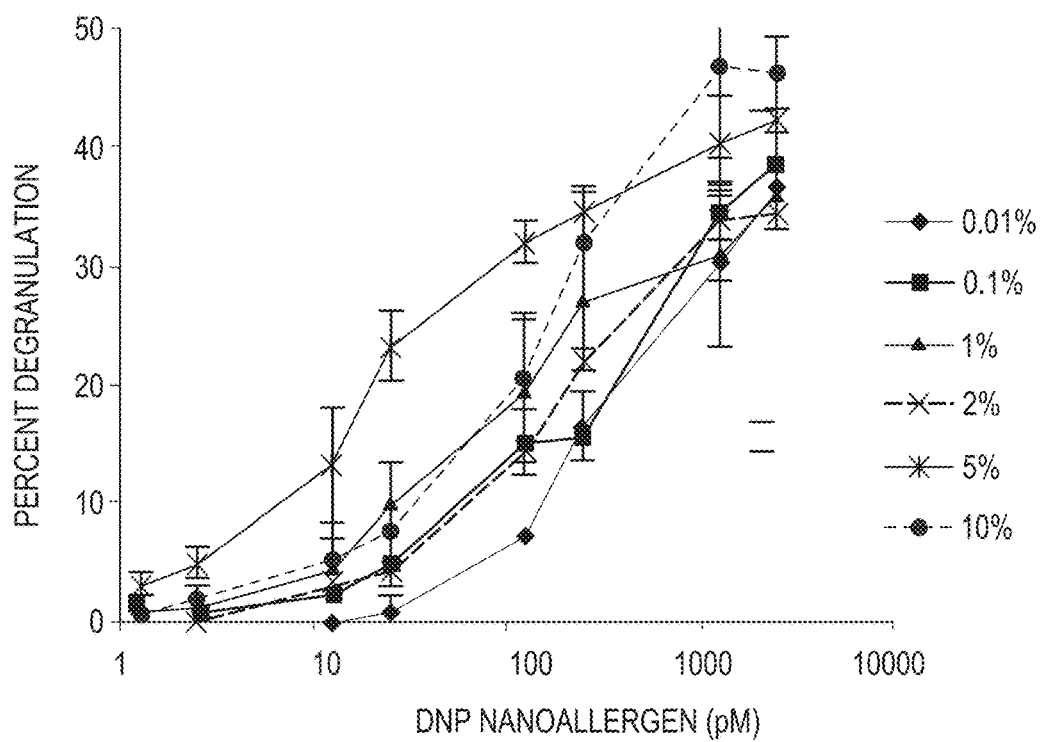
Figure 20C:
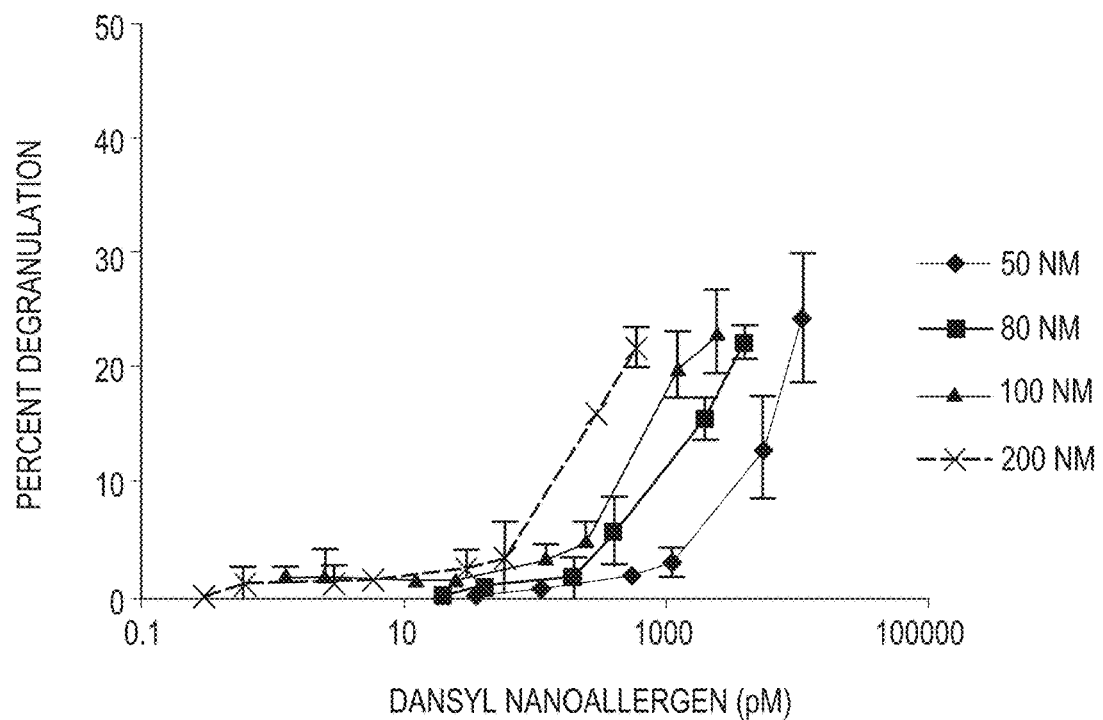
Figure 20D:
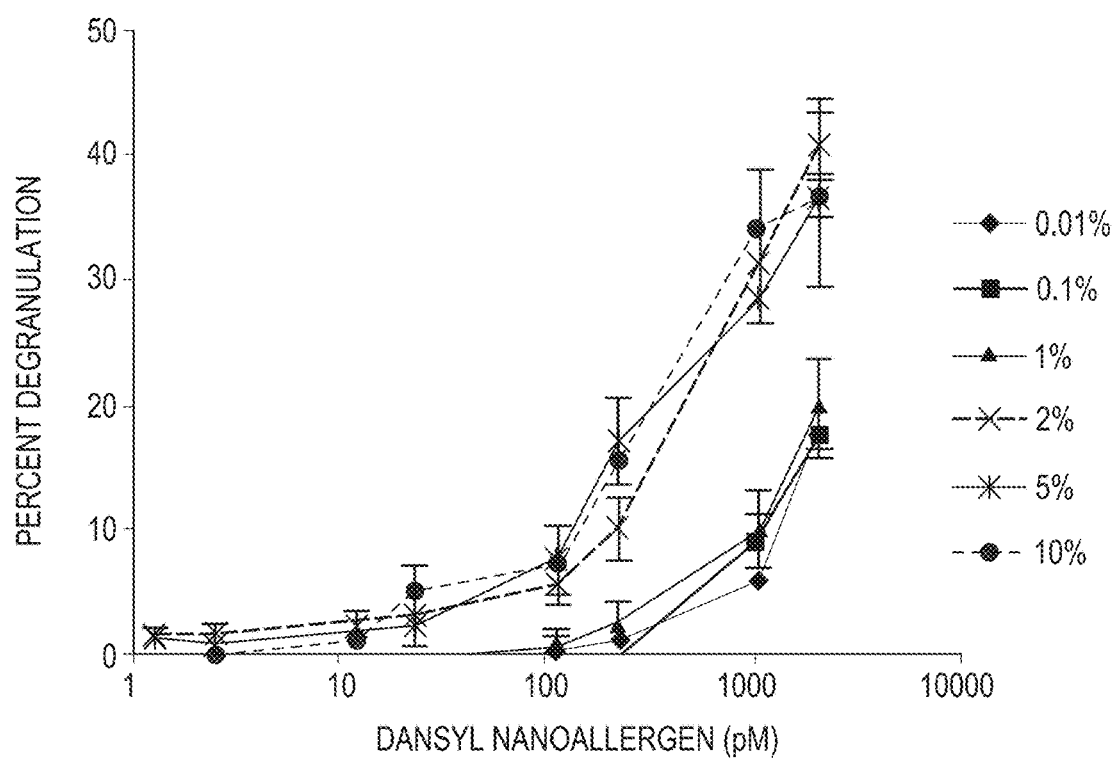

Particle size and peptide density can greatly affect the avidity a liposome has for the specified cell surface. We demonstrated that increasing particle size (50, 80, 100, 200 nm diameter sizes were tested) while keeping other parameters (such as hapten loading) constant results in more potent degranulation responses (FIG. 20A, 20C). Additionally, increasing the percent of loaded hapten-lipid conjugates (0.01, 0.1, 1, 2, 5 and 10% of total lipid) increased the maximum percent degranulation for similar reasons (FIG. 20B, 20D). For the DNP nanoallergen, the percent loading did not have a significant effect on the degranulation, however, DNP nanoallergens demonstrated greater responses at lower concentrations with higher (10% and 5%) loading. The lower affinity dansyl nanoallergen demonstrated a drastic increase in degranulation response between 1% and 2% loading (FIG. 20D). Overall, this data indicated the reliability of these single hapten loaded nanoallergens at inducing a strong degranulation response.

Nanoallergen Binding and Degranulation Kinetics.

Figure 19D:
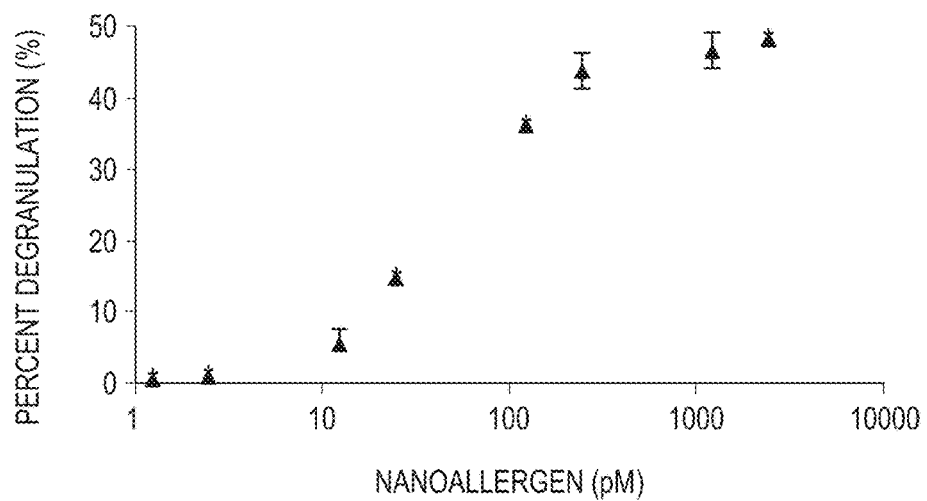
Figure 21:
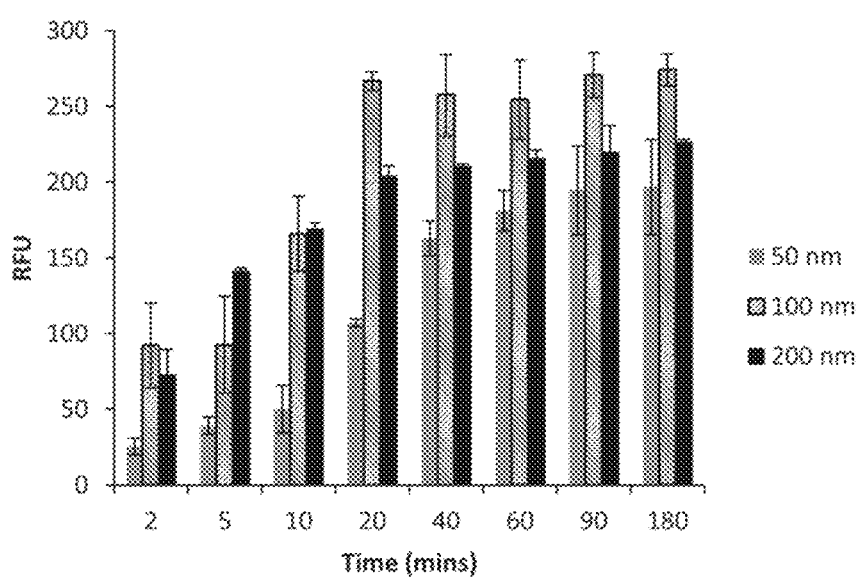
FIG. 21. Kinetic binding of DNP nanoallergens. Nanoallergens of 50, 100 and 200 nm were loaded with 2% DNP-lipid and 600 molecules of fluorescent Did dye per particle and incubated with RBL cells primed with IgE$^{DNP}$ and then analyzed by flow cytometry at various time points.
Figure 26:
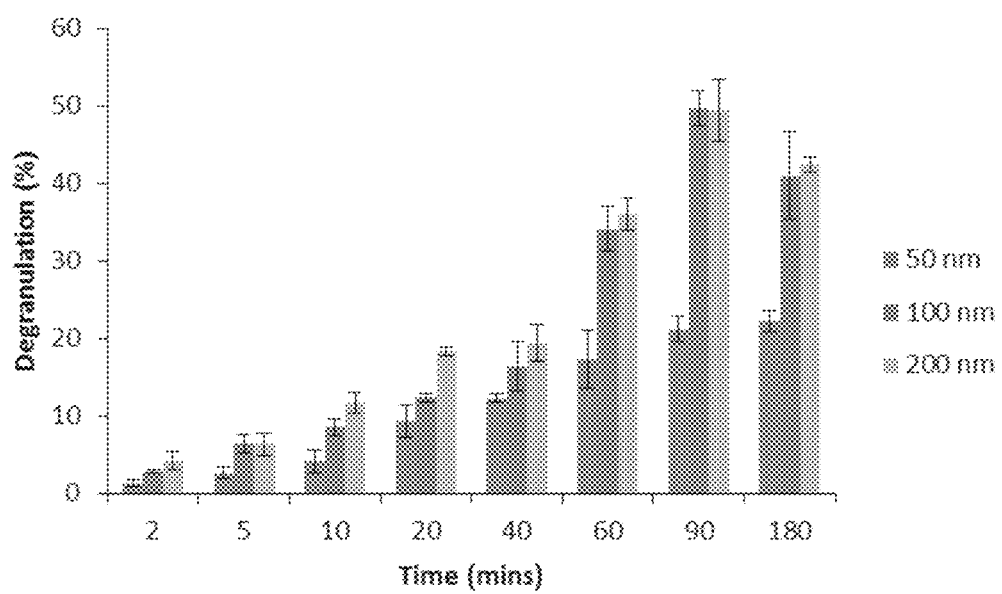
FIG. 26. Nanoallergen degranulation increases over time. RBL cells primed with IgE$^{DNP}$ demonstrate increasing responses to 2% loaded DNP nanoallergens over the course of two hours.
Figure 27A:
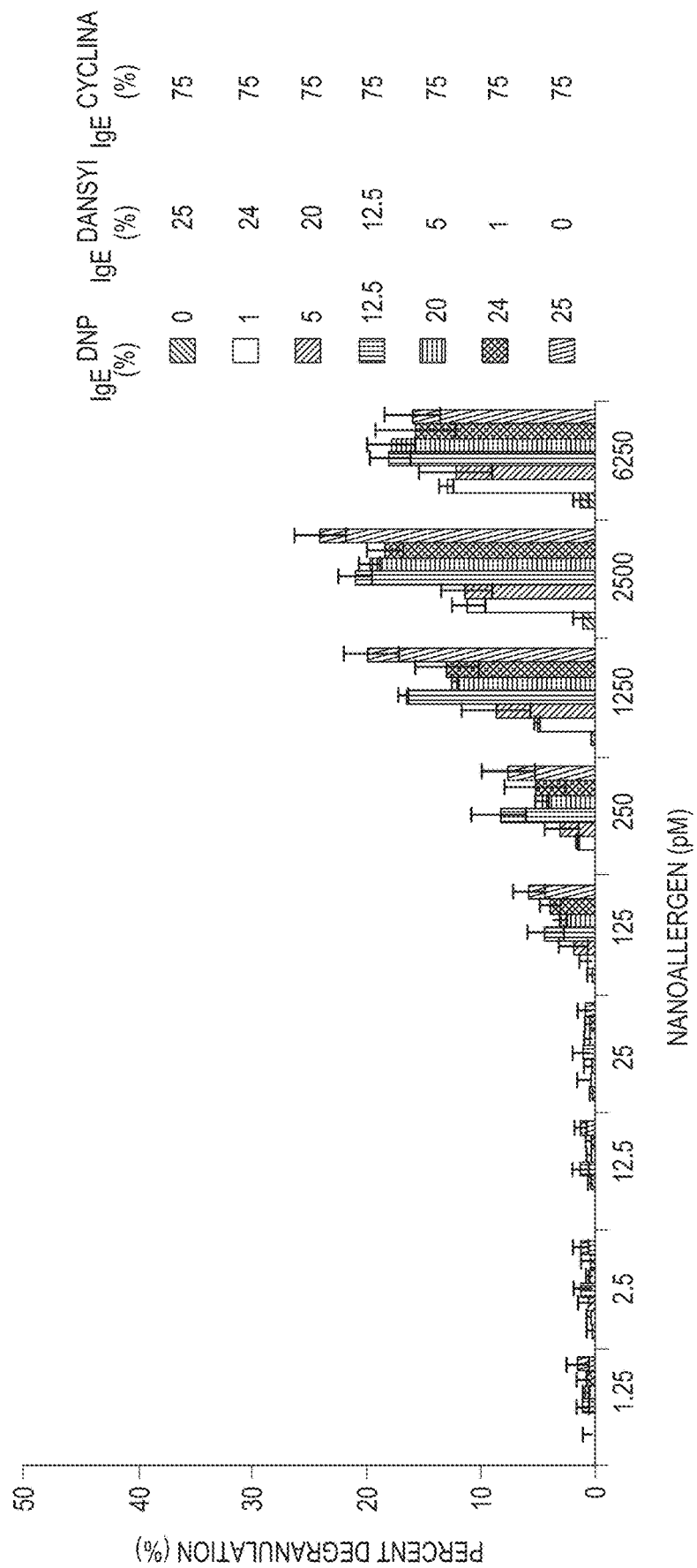
FIG. 27A-E. Hapten and IgE combinations demonstrate varying degranulation response. 100 nm Nanoallergens with 2% hapten loading were incubated with cells primed with 75% orthogonal IgE$^{CyclinA}$ and between 0-25% IgE$^{DNP}$ with IgE$^{Dansyl}$ comprising the remainder. Liposomes consisted of 0% DNP (A.), 0.1% DNP (B.) 1% DNP (C.), 1.9% DNP (D.) and 2% DNP (E.) with the remainder Dansyl for a total of 2% by mole hapten loading.
Figure 27B:
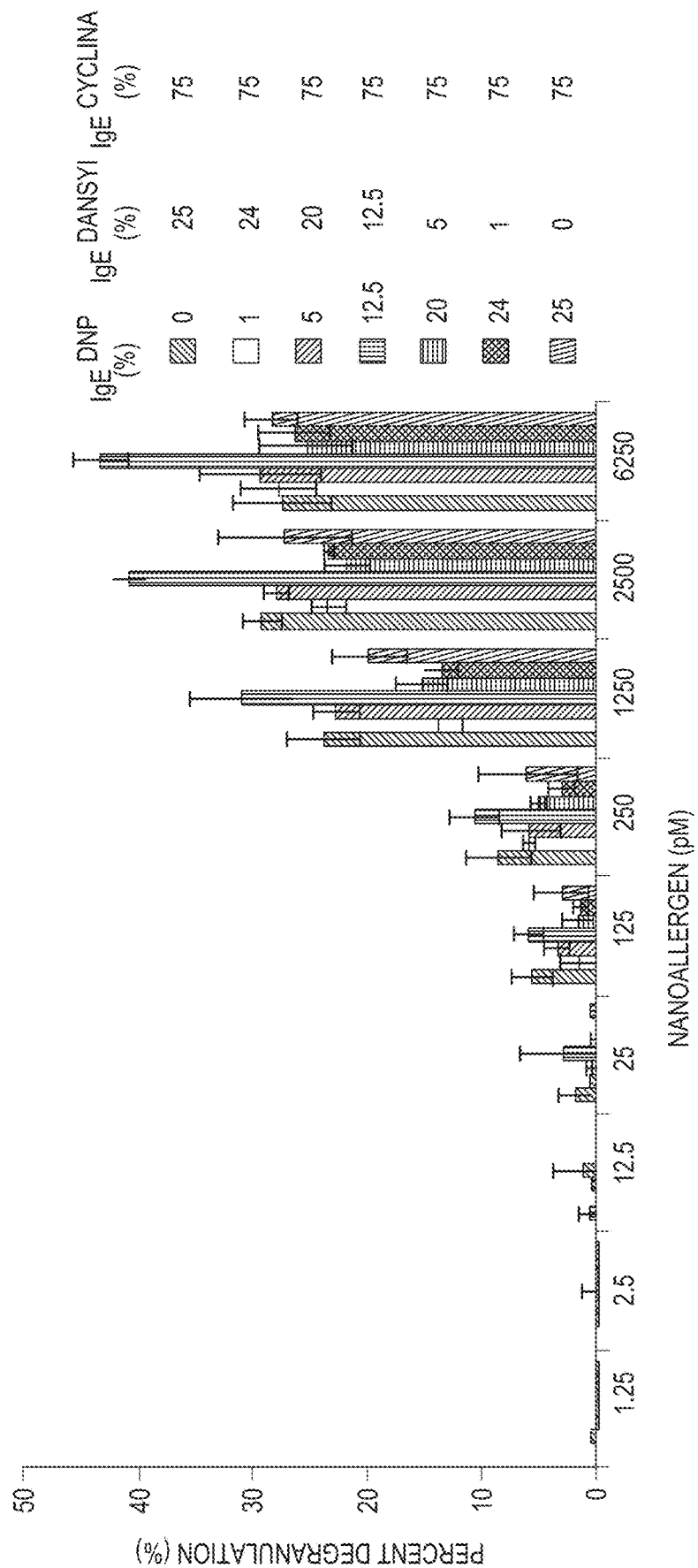
Figure 27C:
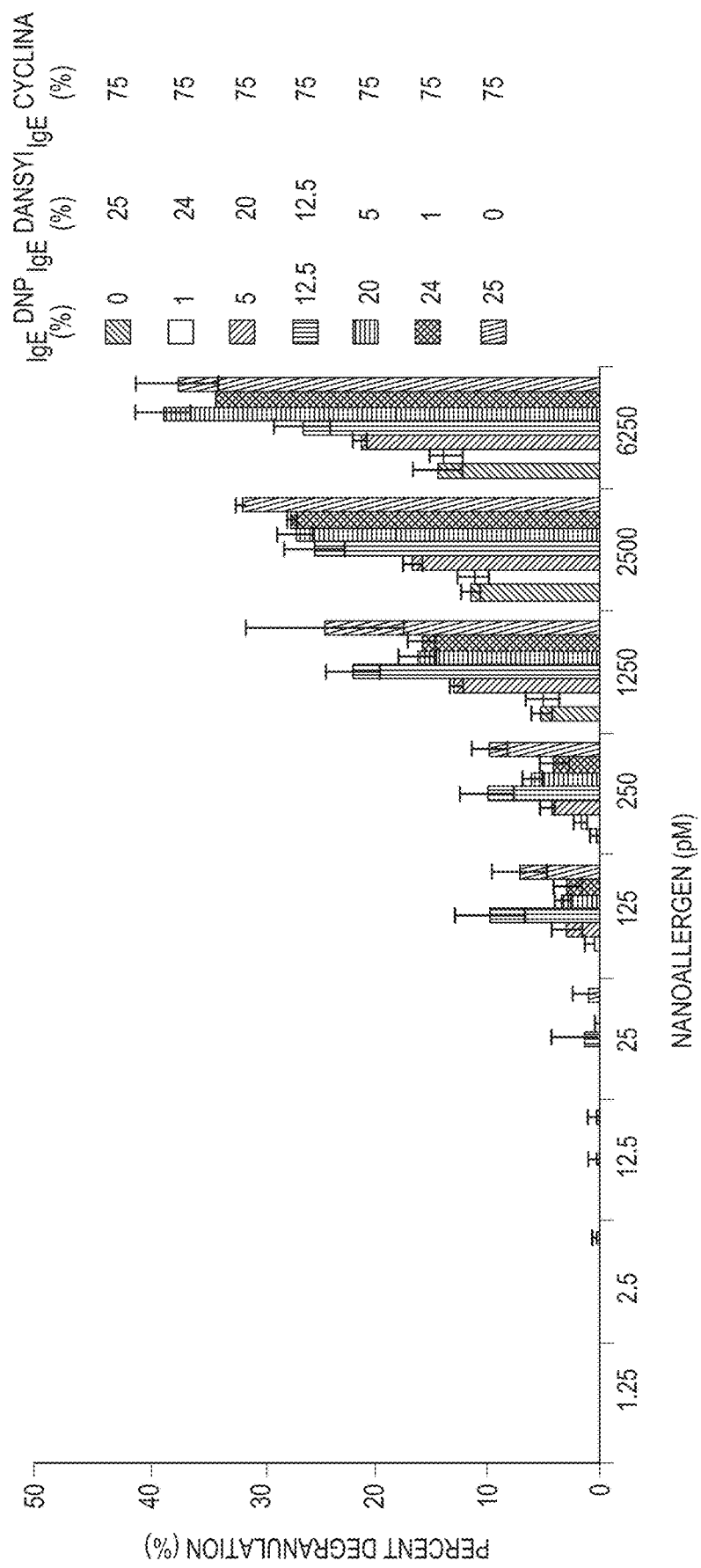
Figure 27D:
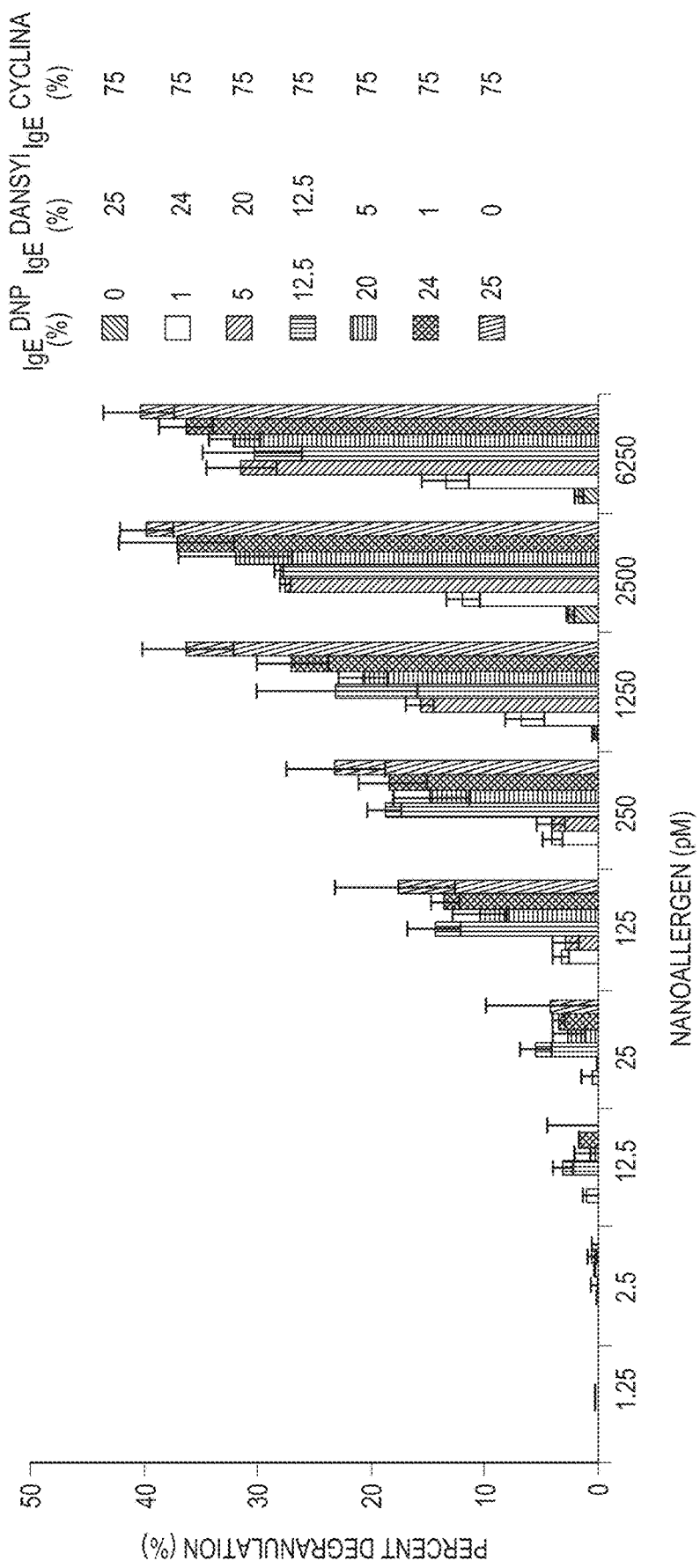
Figure 27E:
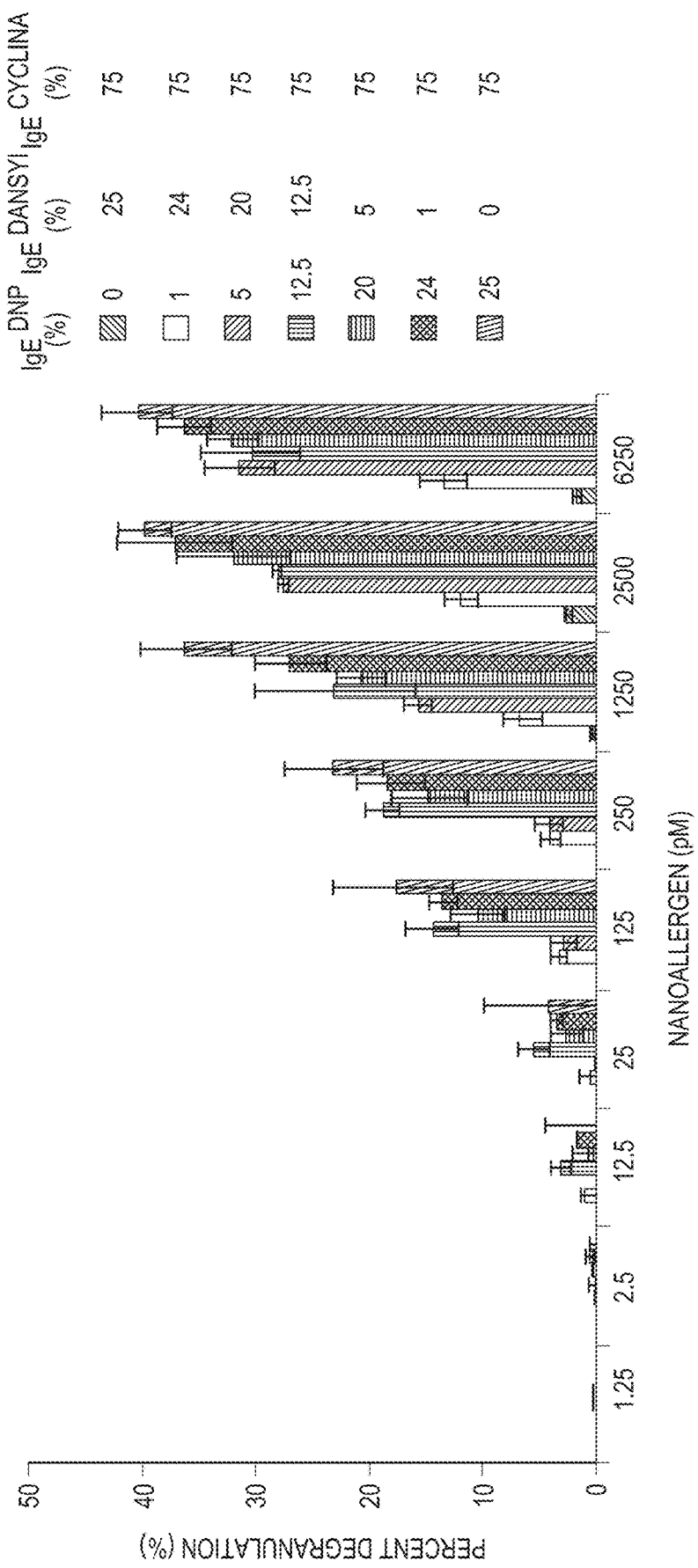

To further demonstrate the utility of the nanoallergen platform, we performed a kinetic binding experiment. As demonstrated in FIG. 19D, the maximum nanoallergen binding to the cells did not relate to the maximum degranulation response. The data demonstrates that there is a threshold of binding necessary to stimulate maximum degranulation response, but any additional binding did not result in an increase in degranulation response. To address this question, we tested varying sizes of DNP nanoallergens using RBL cells primed with 25% DNP specific IgE and observed their degranulation response at various time points between 2 and 120 minutes at 4° C. (FIG. 21). The data indicates that the number of bound particles increases between 1-20 minutes for the 100 nm and 200 nm particles, while the 50 nm particles steadily bound over one hour. Additionally, the large liposomes had higher initial binding than the 50 nm liposome. We simultaneously observed degranulation from these same 50, 100 and 200 nm particles (FIG. 26). The degranulation experiments demonstrated an increasing degranulation response over 90 minutes for all particle sizes. However, the 50 nm particles triggered less degranulation at all time points, suggesting the slower binding kinetics of the smaller particles influenced the degranulation response.

Hapten and IgE Combinations Affect Degranulation Response.

The versatility of the nanoallergen platform is best exemplified when multiple types of haptens were loaded into the bilayer. Because protein allergens present multiple IgE binding epitopes on the same allergen, nanoallergens could readily emulate protein allergens through epitope heterogeneity and precise epitope loading. By loading both DNP and dansyl haptens on the same particle, we used nanoallergens to demonstrate the effects of antigen heterogeneity on degranulation response. We loaded nanoallergens with various ratios of DNP-lipid to dansyl-lipid while maintaining the total hapten-lipid loading at 2% of total lipid. Additionally, we varied epitope specific IgE ratios when priming the RBL cells to simulate the variability in clinical IgE content (FIG. 27A-E, Table 8-4).

TABLE 8-4

Hapten-lipid variations. Listed here are the respective hapten-lipids molecules, the amino acid residue conjugated to the hapten, the monovalent affinity of the hapten-amino acid conjugate to its respective IgE, and the $EC_{50}$ value and maximum degranulation of a 2% loaded hapten-lipid nanoallergen. Degranulation experiments were performed using RBL-2H3 cells primed with 25% specific hapten IgE and 25% orthogonal IgE. Stars (*) indicate data from manuscript by Handlogten et al.

| Hapten | Reside | $K_d$ (nM) | $EC_{50}$ (pM) | Max (%) |
|---|---|---|---|---|
| DNP | Glu | 15 ± 2.5* | 10.7 ± 2 | 28.1 ± 0.6 |
|  | Lys | 105 ± 15* | 45.4 ± 4 | 24.6 ± 0.6 |
| Dansyl | Glu | 147 ± 45 | 279 ± 108 | 20.7 ± 2.4 |
|  | Lys | 23 ± 12 | 23 ± 13 | 33.3 ± 3 |

Figure 22A:
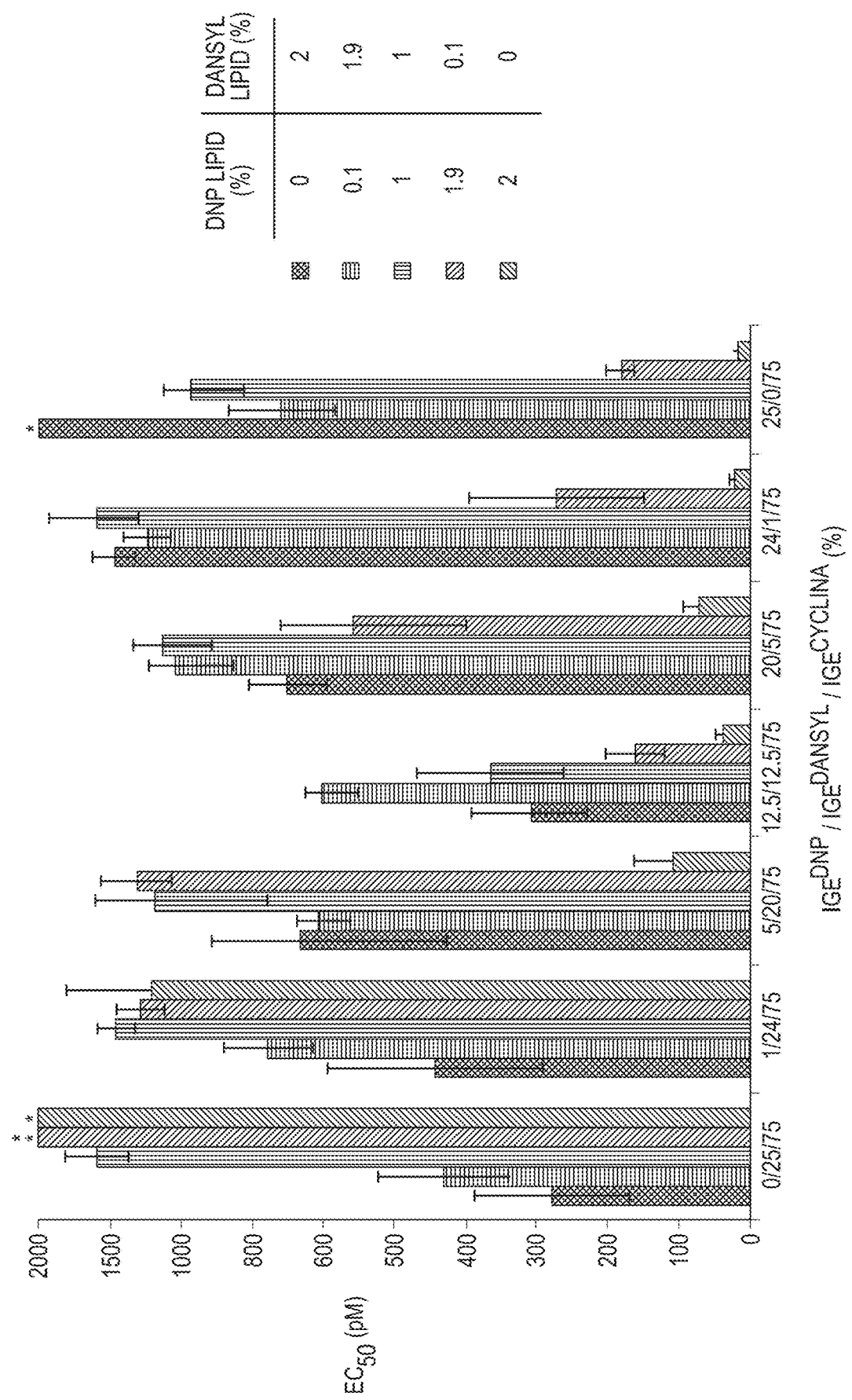
FIG. 22A-B. $EC_{50}$ and maximum degranulation values for DNP-Dansyl combination Nanoallergen. The IgE ratios used to prime the RBL-2H3 cells were varied as demonstrated on the X axis. Each color bar graph corresponds to hapten-lipid loading ratios. Note: Stars indicate a lack of response at all concentrations tested. Double stars indicate $EC_{50}$ values above 5000 pM. $EC_{50}$ values are in A. and maximum degranulation values are shown in B.
Figure 22B:
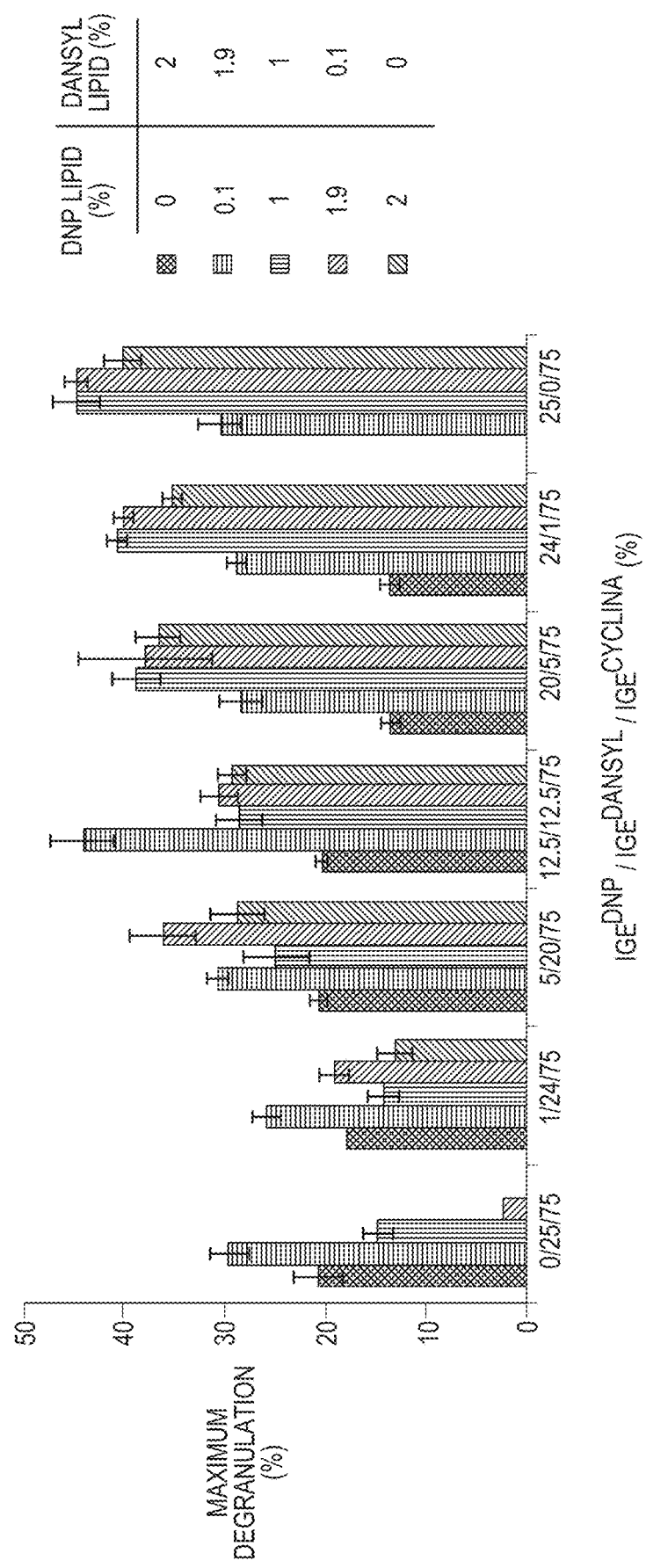

FIG. 22 presents the $EC_{50}$ values and maximum for each of these curves. The data demonstrates the complexity of the degranulation response and how many factors influence degranulation response, such as particle valency, IgE ratios and allergen concentration. Nevertheless, some trends were fairly apparent. For example, the optimal degranulation response occurred for all lipid loading ratios at 12.5% $IgE^{DNP}$ and 12.5% $IgE^{dansyl}$. Also, for most nanoallergens, there is a larger maximum response (30-40% of maximum) at low nanomolar nanoallergen, demonstrating nanoallergens ability to mimic protein allergen potency in vitro.

Discussion.

The results presented in this paper establish the nanoallergen platform as a versatile and effective method for reliable and reproducible activation of cellular degranulation. The platform addresses several challenges of in vitro allergy models such as the difficulty of relating allergen binding affinity directly to a degranulation response given the complex nature of degranulation. Degranulation is affected by both allergen binding attributes such as size of IgE-FcεRI clusters and number of clusters as well as cellular properties such as downstream signal transduction. Here, we used the nanoallergen platform to systematically dissect and investigate aspects of allergen binding such as valency and monovalent affinity and observe their direct effects on degranulation responses using established in vitro degranulation assays.

By using hapten molecules with known affinities, we demonstrate the complexities of the allergen binding-degranulation relationship. As stated earlier, $IgE^{DNP}$ and $IgE^{dansyl}$ have different affinities for their respective haptens. Moreover, in an effort to widen their affinity difference, we conjugated both haptens to a glutamic acid residue (FIG. 23). The result was a nearly ten-fold difference in affinity, making the haptens a suitable pair for heterogeneous nanoallergens ($K_d^{DNP}$=15 nM; $K_d^{dansyl}$=147 nM, Table 8-4, FIG. 29).[17] This difference in monovalent affinity translates to a stronger degranulation response for the higher affinity DNP nanoallergen than the dansyl nanoallergen (Table 8-3). Likewise, increasing hapten loading, and therefore valency, increases the degranulation response, although not in a linear fashion (FIG. 20). For the dansyl nanoallergen, there was a large increase in response between 1% loading and 2%, loading, but the DNP nanoallergen did not have as clear a trend, instead only demonstrating marginally higher responses for higher hapten loading. This is likely due to the ten-fold difference in monovalent affinity between DNP-$IgE^{DNP}$ and dansyl-$IgE^{dansyl}$ interactions causing longer disassociation half-lives for a single DNP-$IgE^{DNP}$ interaction. Degranulation requires the clustering of three or more IgE-FcεRI complexes, but given the high valency of nanoallergens and the rapid diffusion of IgE-FcεRI on the cell surface, it appears that one of the most crucial steps in a degranulation response is the binding of the second IgE-FcεRI complex.[7,37]

Reduced dissociation kinetics from the cell surface increases the likelihood of a second IgE-FcεRI receptor diffusing to the nanoallergen and forming larger clusters. A weaker monovalent affinity would be reflected in a larger $k_{off}$ for the dansyl-IgE$^{dansyl}$, resulting in a shorter disassociation half-life and increasing the likelihood of nanoallergen disassociating from the cell surface before a second IgE interaction can be formed. This suggests that there is a critical spacing distance between haptens which facilitates bivalent binding to the same IgE molecule, allowing nanoallergen-cell interactions to have increased half-lives, thereby increasing the likelihood of IgE-FcεRI cluster formation. This bivalent IgE binding is a plausible explanation for the increase in degranulation response between 1% and 2% for dansyl nanoallergens (FIG. 20D, Table 8-2).

Figure 29B:
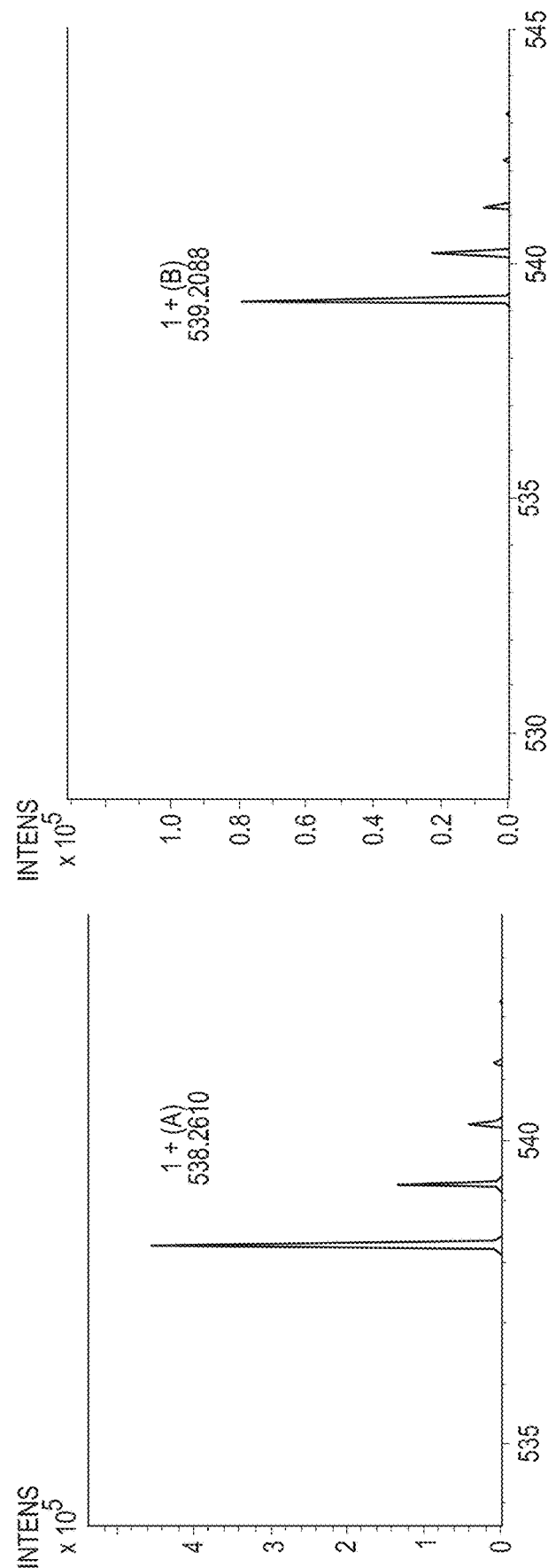
Figure 29C:
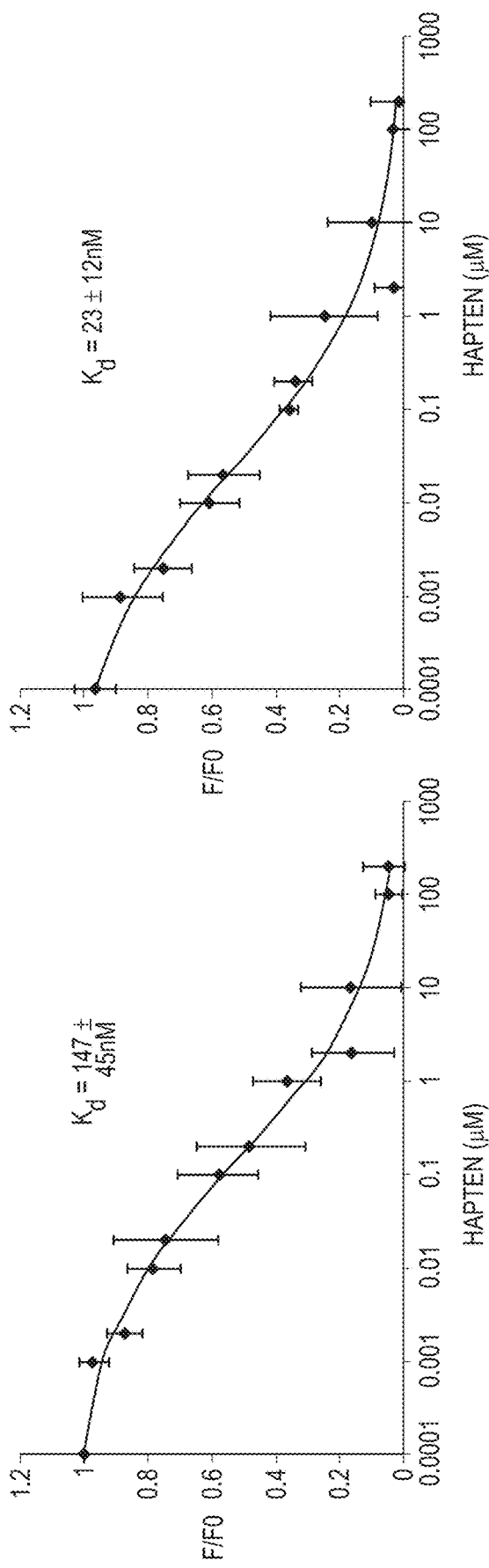

Another important factor that impacts degranulation response was epitope heterogeneity. The higher affinity (DNP) hapten caused the strongest response at lower concentrations when it was the only epitope present, due likely to its high monovalent affinity (FIG. 22). Nevertheless, when nanoallergens were prepared presenting both DNP as well as dansyl haptens at varying ratios, intensity of cell response varied at different concentrations. For example, the $EC_{50}$ value for the 12.5/12.5/75% IgE$^{DNP}$/IgE$^{dansyl}$/IgE$^{dansyl}$ ratio increased from 310±80 pM with the 2% loaded dansyl nanoallergen to 600±50 pM for the 0.1/1.9% dansyl/DNP hapten loaded nanoallergens, demonstrating a p value of less than 0.01 (FIG. 22A and FIG. 27). Even though a higher affinity hapten (DNP) was added to the nanoallergen, the data demonstrates a decrease in degranulation response. We predict the difference originating from the 2% loading density providing the critical distance for hapten separation that can accommodate bivalent binding of dansyl haptens to a single IgE$^{dansyl}$ (Table 8-2). The incorporation of DNP hapten into the nanoallergens results in a slight decrease in the density of dansyl on the particle surface and decreasing the statistical likelihood of an IgE$^{dansyl}$ molecule from binding bivalently to a nanoallergen, resulting in a reduction in the avidity of the nanoallergen (FIG. 29). Nevertheless, for nanoallergens of greater than 1% DNP loading, this reduction in bivalent binding was offset by the increased monovalent affinity of DNP and resulted in enhanced degranulation responses. For example, the $EC_{50}$ value for 12.5/12.5/75% IgE$^{DNP}$/IgE$^{dansyl}$/IgE$^{dansyl}$ ratio decreased as the DNP hapten ratio was increased from 0.1 to 1% (p<0.05, FIG. 22A and FIG. 27). Additionally, this effect is seen when reversing the two haptens; as 0.1% dansyl is introduced into a DNP nanoallergen, a statically significant (p<0.01) increase in $EC_{50}$ value occurs at every IgE ratio except 25% and 24% IgE$^{dansyl}$ (FIG. 22A). While a small decrease in affinity would be expected due to the introduction of a lower affinity hapten, such large $EC_{50}$ value differences suggest that the introduction of dansyl haptens on the surface is also preventing bivalent IgE$^{DNP}$ binding.

Figure 19E:
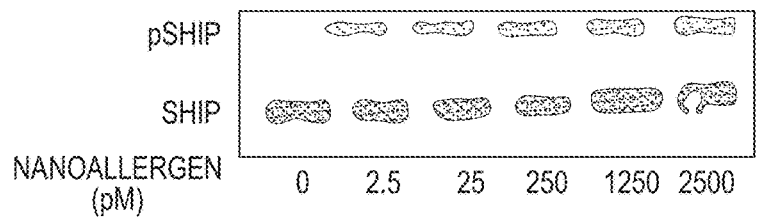

The nanoallergen studies presented here also reveal several more nuanced aspects of a degranulation response. The higher the overall nanoallergen valency, the more IgE-hapten interactions can be formed and the stronger the degranulation response (Table 8-2). Additionally, avidity was not the only factor determining the potency of nanoallergens. The non-linear relationship between hapten surface density and the degranulation response demonstrated that there was an optimal avidity for the intensity of the maximum degranulation response for a given nanoallergen formulation, and this optimal response was also mediated through intracellular inhibitory cascades. Our data indicates that the maximum degranulation response did not occur when the highest number of nanoallergens was bound on the cell surface. As demonstrated in FIG. 19, nanoallergen binding was highest at 2.5 nM for 2% loaded DNP nanoallergens, while the maximum degranulation response occurred at 250 pM when these same nanoallergens were used to stimulate degranulation (FIG. 27). A possible explanation for this is the presence of intracellular inhibitory cascades that activate during overstimulation.[38] Furthermore, as demonstrated by FIGS. 19D and 19E, nanoallergens at supraoptimal concentrations stimulated intracellular inhibitory cascades (SHIP protein).

Studies conducted using nanoallergens has the potential to reveal detailed and critical information about allergen proteins and their epitopes that even the purified natural allergen proteins themselves cannot deliver. Factors such as affinity, valency, epitope heterogeneity and intracellular inhibitory cascades are crucial complicating factors for degranulation responses. Nanoallergens allow for precise control over affinity, valency and provide immunogenic data on individual epitopes. Meanwhile, without sophisticated binding experiments, it is difficult to decipher which epitopes on allergen proteins are binding and the kinetics of these interactions. Finally, allergen proteins can only have their specific epitopes be altered with site specific directed mutagenesis, which is rather time consuming and challenging, making screening for important allergy epitopes very difficult. In addition, nanoallergens can be used to assess the kinetics of allergen binding (FIG. 21) due to their ability to readily incorporate fluorescent dyes. Likewise, nanoallergens offer method to assess the influence on parameters such as allergen size on degranulation kinetics (FIG. 26).

In conclusion, the nanoallergen platform presented in this paper provides an efficient and versatile platform for allergy research. Nanoallergens offer several advantages over the current BSA-hapten system. The ability to generate very nanoallergens of very high valency allows them to trigger degranulation responses at similarly low (nanomolar to picomolar) concentrations as native allergen proteins. For example, peanut allergens, Ara h2 and Ara h6, have been identified to have $EC_{50}$ values in cellular studies in the low picomolar range using various sera from highly allergic individuals, and these potent responses are not possible to emulate with linear peptide epitopes without a highly multivalent platform such as nanoallergens.[40] Even with the high affinity DNP hapten, DNP-BSA with a valency of 18 that was used in this study as a control was only able to trigger degranulation in the nanomolar range ($EC_{50}$=26±9 nM) while a 2% loaded DNP nanoallergen (valency of 800) was able to trigger degranulation in the picomolar range ($EC_{50}$=180±20 pM) (FIG. 19). In addition to the increase of valency, nanoallergens can also take advantage of simultaneous bivalent interactions on a single IgE antibody and further intensify the degranulation response. The atypical size and capacity to display epitopes at a very high valency make nanoallergens a very viable platform for studying and sufficiently ranking peptide epitopes with low affinities. Furthermore, nanoallergens offer precise control over allergen valency, which in turn can be used to study the kinetics of IgE-FcεRI clustering. These particles can be easily tagged with fluorescent molecules, facilitating studies of IgE-FcεRI cluster size and shape on immunogenicity. Finally, and most importantly, nanoallergens can be formulated with epitope heterogeneity and precise control over epitope ratios on the particles. For this study only two hapten molecules were used, but nanoallergens can readily display any number of hapten molecules or epitope peptides in any combination. This means nanoallergens can easily be formulated to emulate various immunogenic proteins simply by changing the epitope loading ratios. This process could also be used to select epitopes most crucial in stimulating degranulation and provide critical information for future degranulation inhibitor designs.

In summary, degranulation caused by type I hypersensitivity (allergies) is a complex biophysical process, and available experimental models for studying relevant immunoglobulin E (IgE) binding epitopes on allergen proteins lack the ability to adequately evaluate, rank and associate these epitopes individually and with each other. In this study, we propose a new allergy model system for studying potential allergen epitopes using nanoallergens, liposomes modified to effectively display IgE binding epitopes/haptens. By utilizing the covalently conjugated lipid tails on two hapten molecules (dinitrophenol and dansyl), hapten molecules were successfully incorporated into liposomes with high precision to form nanoallergens. Nanoallergens, with precisely controlled high particle valency, can trigger degranulation with much greater sensitivity than commonly used bovine serum albumin (BSA) conjugates. In RBL cell experiments, nanoallergens with only 2% hapten loading were able to trigger degranulation in vitro at concentrations as low as 1 nM. Additionally, unlike BSA-hapten conjugates, nanoallergens allow exact control over particle size and valency. By varying the nanoallergen parameters such as size, valency, monovalent affinity of hapten, and specific IgE ratios, we exposed the importance of these variables on degranulation intensity while demonstrating nanoallergens' potential for evaluating both high and low affinity epitopes. The data presented in this article establish nanoallergen platform as a reliable and versatile allergy model to study and evaluate allergen epitopes in mast cell degranulation.

Example 8 Citations

1. Tang A W. A practical guide to anaphylaxis. *Am Fam Physician.* 2003; 68(7):1325-1332.
2. Metzger H. Transmembrane signaling—the joy of aggregation. *J Immunol.* 1992; 149(5):1477-1487.
3. Metzger H. The receptor with high-affinity for IgE. *Immunol Rev.* 1992; 125:37-48.
4. Metzger H. Larger oligomers of ige are more effective than dimers in stimulating rat basophilic leukemia-cells. *Journal of Immunology.* 1980; 125(2):701-710.
5. Grasberger, B. et al. Interaction between proteins localized in membranes. *Proc Natl AcadSci USA.* 1986; 83(17):6258-6262.
6. Crothers D M, Metzger H. Influence of polyvalency on binding properties of antibodies. *Immunochemistry.* 1972; 9(3):341-&.
7. Mahajan A, Barua D, Cutler P, Wilson B S. Optimal aggregation of FcεRI with a structurally defined trivalent ligand overrides negative regulation driven by phosphatases. *ACS Chemical Biology.* 2014; 9:1508-1519.
8. Das R, Baird E, Goldstein B, Coates G, Holowka D, Baird B. Effectiveness of PEG based ligands as potent inhibitors of IgE mediated signaling is determined by specific features of ligand-IgE binding. *Biophys J.* 2003; 84(2): 396A-397A.
9. Tanabe S. Epitope peptides and immunotherapy. *Curr Protein Peptide Sci.* 2007; 8(1):109-118.
10. Basciano L K, Berenstein E H, Kmak L, Siraganian R P. Monoclonal-antibodies that inhibit ige binding. *J Biol Chem.* 1986; 261(25): 1823-1831.
11. Albrecht M, Kuehne Y, Ballmer-Weber B K, et al. Relevance of IgE binding to short peptides for the allergenic activity of food allergens. *J Allergy Clin Immunol.* 2009; 124(2):328-336.
12. Palmer G W, Dibbern Jr. D A, Burks A W, et al. Comparative potency of ara h 1 and ara h 2 in immunochemical and functional assays of allergenicity. *Clinical Immunology.* 2005; 115(3):302-312.
13. McDermott R A, Porterfield H S, El Mezayen R, et al. Contribution of ara h 2 to peanut-specific, immunoglobulin E-mediated, cell activation. *Clinical and Experimental Allergy.* 2007; 37(5):752-763.
14. Porterfield H S, Murray K S, Schlichting D G, et al. Effector activity of peanut allergens: A critical role for ara h 2, ara h 6, and their variants. *Clin Exp Allergy.* 2009; 39(7):1099-1108.
15. Otsu K, Guo R, Dreskin S C. Epitope analysis of ara h 2 and ara h 6: Characteristic patterns of IgE-binding fingerprints among individuals with similar clinical histories. *Clinical & Experimental Allergy.* 2014.
16. Michael W. Handlogten, Peter E. Deak and Basar Bilgicer. Two-allergen model reveals complex relationship between IgE crosslinking and degranulation. *Chemistry & Biology.* 2014: dx.doi.org/10.1016/j.chembiol.2014.08.019.
17. Handlogten M W, Kiziltepe T, Serezani A P, Kaplan M H, Bilgicer B. Inhibition of weak-affinity epitope-IgE interactions prevents mast cell degranulation. *Nat Chem Biol.* 2013; 9:789-795.
18. Posner R G, Lee B, Conrad D H, Holowka D, Baird B, Goldstein B. Aggregation of ige receptor complexes on rat basophilic leukemia-cells does not change the intrinsic affinity but can alter the kinetics of the ligand ige interaction. *Biochemistry.* 1992; 31(23):5350-5356.
19. Harris N T, Goldstein B, Holowka D, Baird B. Altered patterns of tyrosine phosphorylation and syk activation for sterically restricted cyclic dimers of IgE-fc epsilon RI. *Biochemistry.* 1997; 36(8):2237-2242.
20. Collins A M, Thelian D, Basil M. Antigen valency as a determinant of the responsiveness of ige-sensitized rat basophil leukemia-cells. *Int Arch Allergy Immunol.* 1995; 107(4):547-556.
21. Handlogten M W, Kiziltepe T, Bilgicer B. Design of a heterotetravalent synthetic allergen that reflects epitope heterogeneity and IgE antibody variability to study mast cell degranulation. *Biochem J.* 2013; 449:91-99.
22. Xu K L, Goldstein B, Holowka D, Baird B. Kinetics of multivalent antigen DNP-BSA binding to IgE-fc epsilon RI in relationship to the stimulated tyrosine phosphorylation of fc epsilon RI. *J Immunol.* 1998; 160(7):3225-3235.
23. Handlogten M W, Kiziltepe T, Serezani A P, Kaplan M H, Bilgicer B. Inhibition of weak-affinity epitope-IgE interactions prevents mast cell degranulation. *Nat Chem Biol.* 2013; 9(12):789-795.
24. Stanley J, King N, Burks A, et al. Identification and mutational analysis of the immunodominant IgE binding epitopes of the major peanut allergen ara h 2. *Arch Biochem Biophys.* 1997; 342(2):244-253.
25. Handlogten M W, Serezani A P, Sinn A L, Pollok K E, Kaplan M H, Bilgicer B. A heterobivalent ligand inhibits mast cell degranulation via selective inhibition of allergen-IgE interactions in vivo. *J Immunol.* 2014; 192(5): 2035-2041.

26. Handlogten M W, Kiziltepe T, Serezani A P, Kaplan M H, Bilgicer B. Selective inhibition of weak-affinity epitope-IgE interactions via heterobivalent inhibitor design prevents mast cell degranulation. *Nature Chemical Biology.* 2013; in print.
27. Handlogten M W, Kiziltepe T, Alves N J, Bilgicer B. Synthetic allergen design reveals the significance of moderate affinity epitopes in mast cell degranulation. *ACS Chem Biol.* 2012; 7(1554-8937 (Electronic); 1554-8929 (Linking); 11):1796-1801.
28. Christensen L H, Holm J, Lund G, Riise E, Lund K. Several distinct properties of the IgE repertoire determine effector cell degranulation in response to allergen challenge. *J Allergy Clin Immunol.* 2008; 122(2):298-304.
29. Stefanick J F, Ashley J D, Kiziltepe T, Bilgicer B. A systematic analysis of peptide linker length and liposomal polyethylene glycol coating on cellular uptake of peptide-targeted liposomes. *ACS Nano.* 2013; 7 (4):2935-2947.
30. Stefanick J F, Ashley J D, Bilgicer B. Enhanced cellular uptake of peptide-targeted nanoparticles through increased peptide hydrophilicity and optimized ethylene glycol peptide-linker length. *ACS Nano.* 2013; 7 (9):8115-8127.
31. Stefanick J F, Kiziltepe T, Bilgicer B. Improved peptide-targeted liposome design through optimized peptide hydrophilicity, ethylene glycol linker length, and peptide density. *J Biomed Nanotechnol.* 2014: In Print.
32. Ashley J D, Stefanick J F, Schroeder V, Suckow M A, Kiziltepe T, Bilgicer B. Liposomal bortezomib nanoparticles via boronic ester prodrug formulation for improved therapeutic efficacy in vivo. *J Med Chem.* 2014: In print.
33. Ashley J D, Stefanick J F, Schroeder V A, Suckow M A, Kiziltepe T, Bilgicer B. Liposomal bortezomib nanoparticles via boronic ester prodrug formulation for improved therapeutic efficacy in vivo. *J Med Chem.* 2014; 57(12):5282-5292.
34. Ashley J D, Stefanick J F, Schroeder V A, et al. Liposomal carfilzomib nanoparticles effectively target multiple myeloma cells and demonstrate enhanced efficacy in vivo. *J Controlled Release.* 2014; 196(0):113-121.
35. Gimborn K, Lessmann E, Kuppig S, Krystal G, Huber M. SHIP down-regulates fc epsilon R1-induced degranulation at supraoptimal IgE or antigen levels. *J Immunol.* 2005; 174(1):507-516.
36. Weetall M, Holowka D, Baird B. Heterologous desensitization of the high affinity receptor for IgE (fc epsilon R1) on RBL cells. *The journal of immunology.* 1993; 150(9):4072-4083.
37. Goldstein B, Posner R G, Torney D C, Erickson J, Holowka D, Baird B. Competition between solution and cell-surface receptors for ligand-dissociation of hapten bound to surface antibody in the presence of solution antibody. *Biophys J.* 1989; 56(5):955-966.
38. Huber M. Activation/inhibition of mast cells by supraoptimal antigen concentrations. *Cell Commun Signal.* 2013; 11:7.
39. Kunze A, Bally M, Hook F, Larson G. Equilibrium-fluctuation-analysis of single liposome binding events reveals how cholesterol and Ca2+ modulate glycosphingolipid trans-interactions. *Scientific Reports.* 2013; 3:1452.
40. Blanc F, Adel-Patient K, Drumare M-, Paty E, Wal J-, Bernard H. Capacity of purified peanut allergens to induce degranulation in a functional in vitro assay: Ara h 2 and ara h 6 are the most efficient elicitors. *Clinical & Experimental Allergy.* 2009; 39(8):1277-1285.

Example 9. Design of Inhibitors to Drug Induced Type I Hypersensitivity

Drug allergies are a type of adverse drug reaction that afflicts over 2 million people per year in the US. These allergies are particularly dangerous because unlike other adverse drug reactions, they are unpredictable and can have a wide variety of symptoms and triggers, and these reactions occur to very commonly used drugs such as sulfa drugs and antibiotics. In particular, immediate immunoglobulin E (IgE) mediated hypersensitivity reactions caused by drugs can be the most life threatening because they cause rapid and severe anaphylaxis reactions. Furthermore, over half of allergy fatalities are due to anaphylaxis reactions to drugs. Currently, the only FDA approved treatments for drug allergies are post-reaction treatments such as antihistamines or corticosteroids, both of which have not shown dependable prevention of anaphylaxis responses, likely due to the rapid onset of anaphylaxis. The only treatment for anaphylaxis reactions to drugs is treatment with epinephrine, which only delays onset of the symptoms for several minutes so that the patient can reach proper medical care. Given the prevalence of these reactions and the lack of adequate treatments, there is a need for development of preventative and/or more rapidly acting treatments for drug reactions. In this example, we discuss the synthesis and in vitro and in vivo characterization of a new design of allergy inhibitor that can be used to prevent IgE mediated allergic reactions triggered by drug molecules.

Severe drug allergy reactions are due to a process called haptenization in which drug molecules covalently bind multivalently to a carrier protein (typical serum albumins) and stimulate immune reactions. This is important because the major IgE mediated hypersensitivity response, degranulation responses are triggered by multivalent cross linking of an allergen protein with several IgE-constant fragment epsilon receptor (FcεRI) complexes, which are present on the surfaces of mast cells and basophils. This crosslinking event then triggers the release of histamine and other inflammatory compounds into systemic circulation. This haptenization process causes drug allergies to differ from food or environmental allergens in that instead of many different IgE binding epitopes on a single allergen protein, the immune system produces IgEs directed against epitopes that contain the drug molecule of interest and therefore all allergy binding epitopes for a particular drug allergy share a common target. This characteristic of severe IgE mediated drug reactions is very advantageous for potential inhibitor designs, as potentially a single inhibitor could significantly inhibit or prevent all IgE recognition of haptenized serum proteins and therefore significantly inhibit or prevent IgE hypersensitivity reactions.

β-lactam antibiotic drug allergies (e.g. penicillin drugs and penicillin derivatives) are of particular concern. β-lactam rings are reactive to primary amines and can readily haptenize serum albumins, causing allergic reactions. Although rates of severe reactions to β-lactam antibiotics are low, given the wide usage of these types of antibiotics, penicillin antibiotics account for over half of the fatal reactions to drugs. Given that β-lactam antibiotics are the most widely prescribed class of antibiotic, any potential drug that can be co-administered to assuage fears of allergic reactions would be extremely valuable. In this example, we describe the synthesis and in vitro and in vivo evaluation of a new class of allergy inhibitors we call covalent heterobivalent inhibitors (cHBIs) designed to specifically and permanently inhibit binding of drug reactive IgE molecules to haptenized proteins. We synthesized inhibitors to two compounds, Penicillin G (a β-lactam antibiotic), and a small molecule frequently used in allergy models, dansyl chloride (dansyl).

Inhibitor Design and Hapten Selection.

The cHBI design consists of three unique chemical moieties that function in concert to provide specific and potent inhibition of IgE mediated degranulation reactions to a specific allergen. This molecule is similar to heterobivalent inhibitors (HBIs) previously reported in our laboratory in that these molecules contain both an antigen binding site (ABS) ligand and a nucleotide binding site (NBS) ligand. The NBS is an underutilized conserved binding site located proximal to the ABS between the heavy and light chain of all immunoglobulins (FIG. 30A). In our laboratory we have identified a few small molecules with low micromolar affinities for the NBS with a wide range of applications. In this example, NBS ligands are used to increase the overall avidity of the inhibitor molecule with the target IgE to improve specificity and potency of the inhibitors. We selected an NBS ligand, 2-naphteleneacetic acid, which we demonstrated to have a 1.8±0.3 μM $K_d$ for IgEs (FIG. 30B, C). Likewise, we also selected two ABS ligands to demonstrate the versatility of these inhibitors, penicillin G and dansyl (FIG. 30D). For the sake of clarity, it is important to note while frequently described as an allergy to penicillin G, the actual ABS ligand is the conjugate of penicillin G with a lysine side chain, forming a penicilloyl group and all ABS ligands for penicillin were synthesized with the penicilloyl group (see methods for further details on cHBI synthesis). Additionally, although the goal of our study is the prevention of allergic reactions to drugs, such as penicillin G, given the lack of commercially available IgEs specific to any penicillin drugs, we used another hapten, dansyl, to establish our experimental in vitro model.

The most crucial aspect of the cHBI design is a reactive group that can form covalent bonds with bound IgE molecules, essentially permanently inhibiting them, in contrast to HBIs which only form reversible interactions (FIG. 31A). In order words, cHBIs are a type of "suicide inhibitor" that irreversibly binds to a target IgE molecule. However, cHBIs have increased specificity due to their heterobivalent targeting of only antibodies that target drug molecules, making them particularly specific. One of the major challenges of suicide inhibitors is to form covalent bonds quickly with intended targets without unacceptable levels of off target conjugation. Therefore, the reactivity of these types of inhibitors needs to be carefully selected to provide optimal specific binding of these molecules to amino acid side chains of proteins of interest, such as allergy reactive IgEs without conjugating off target proteins. Our cHBI design uses an isothiocynate (ITC) reactive moiety to form covalent bonds with specific allergy reactive IgEs. ITC compounds are frequently found in nature and have been shown to have anti-cancer and anti-microbial qualities. ITC groups form thiourea bonds with primary amines rapidly in elevated pH solutions (>9) but react rather slowly under physiological pH (7.4). This means that under normal physiological conditions, ITC inhibitors will react very slowly to form off target bonds. However, when selectively bound to a protein of interest, the increased effective concentration of primary amines from lysine side chains dramatically increases the reaction kinetics of thiourea bond formation. Using this design, we synthesized two cHBI molecules using two different ABS ligands, a dansyl cHBI and a penicilloyl cHBI (Table 9-1).

TABLE 9-1

Disassociation constants for hapten-Napht conjugates.

| Molecule | $K_d$ | Fold Change | |
|---|---|---|---|
| Dansyl | 29.9 ± 10 nM | | |
| | | | P < 0.05 |
| Dansyl HBI | 6.4 ± 2.5 nM | 4.7 | |
| Penicilloyl | 20 ± 4 μM | | |
| | | | P < 0.01 |
| Penicilloyl-DNP HBI | 0.96 ± 0.11 μM | 21 | |

Due to complexities of penicilloyl group, additional design considerations were required to synthesize penicilloyl-cHBI's but the same basic molecule design was used for both cHBI's; see methods for further details.

As demonstrated in FIG. 31B, allergy reactive IgE inhibition is a three step process. First, either the ABS or NBS ligand will bind to the IgE of interest depending on the relative affinities of the two moieties. Next, bivalent binding will occur, further increasing the stability of the overall inhibitor-IgE bond. Finally, due to increased effective concentration of the inhibitor molecule near the IgE of interest, the inhibitor will form a covalent bond with a lysine side chain near the NBS. We have assessed the crystal structures of several IgE molecules and observed a lysine within 10 nm of the central tryptophan of the NBS in each case (FIG. 35). In some cases, more than one lysine was observed, further increasing the odds of covalent conjugation. We have further detailed the kinetics of this reaction and the specificity of the conjugation in previous examples, above. By permanently binding a competitive inhibitor (the ABS ligand) to the IgE of interest, the resulting increase in effective concentration can overcome the multivalent effects and increased monovalent affinities of natural allergens to their respective IgEs. By preventing this allergen-IgE binding interaction and respective crosslinking, we can inhibit or prevent degranulation and the consequences of IgE mediated allergic reactions (FIG. 31C). In this example, we demonstrate that cHBI molecules bivalently bind drug allergy reactive antibodies, specifically form covalent interactions and can prevent antigen binding and therefore degranulation in biological systems.

HBI Molecule Design Increases Avidity.

In order to demonstrate the importance of a bivalent system for binding, we performed fluorescence quenching binding assays on HBI molecules (e.g. cHBI molecules synthesized without an ITC moiety). In order to observe quenching, we tagged penicilloyl molecules with a dinitrophenol (DNP) group; the dansyl molecules required no DNP addition, as dansyl itself quenches fluorescence from tryptophan residues. We synthesized four molecules, a dansyl control, a dansyl-napht HBI, a penicilloyl-DNP control, and a penicilloyl-DNP HBI and tested them for binding with a monoclonal antibody for either penicillin or dansyl (Table 9-1). The results demonstrate a nearly five-fold and 20-fold increase respectively in observed $K_d$ for the dansyl and penicilloyl molecules when the NBS ligand is added. This increase in avidity for the HBI indicates bivalent binding is occurring. It is important to note that due to the lack of commercially produced penicilloyl specific antibodies, we used a penicillin G specific antibody (e.g. specific to the penicillin molecule with an intact beta lactam ring) to test binding of the penicilloyl molecules. This explains why the monovalent affinity was measured in the micromolar range and why a bivalent approach more drastically increased apparent affinity.

cHBIs Specifically Bind Target IgEs.

In order to assert that any degranulation inhibition from cHBIs is due to the proposed IgE binding mechanism rather than a non-specific cellular disruption or another phenomenon, we assessed the level of specific conjugation of cHBI molecules to a target antibody using both ELISA and flow cytometry. In order to quantify conjugation of cHBI molecules, both penicilloyl and dansyl cHBI were synthesized with biotin tags and incubated with specific antibodies, purified with membrane filtration and characterized for cHBI binding using ELISA (Table 9-1). Dansyl-biotin cHBIs demonstrated a near saturated level of conjugation at concentrations as low as 10 nM at pH 7.4 (FIG. 32A). We also assessed conjugation at an increased pH of 9.6 as a positive control as well as conjugation to an orthogonal IgE specific to the small molecule DNP as a negative control. This demonstrates that specific conjugation occurs up to 5000 nm when a predictable level of non-specific conjugation occurs, likely due to the napht interaction with the conserved NBS. Additionally, there was no significant difference between pH 7.4 and pH 9.6 for the cHBI molecules, indicating a high level of specific binding. We also performed a similar ELISA with a penicilloyl cHBI that was tagged with a biotin using a monoclonal anti-Penicillin IgG (Table 9-1, FIG. 32B). Even though the monovalent affinity of penicilloyl for the anti-penicillin IgG was 20 µM, we observed maximum conjugation at 1 µM and little conjugation to a bovine serum albumin control, likely due to bivalent effects (FIG. 32B). Finally, in order to confirm that this specific conjugation can occur on IgEs when bound to FcεRI, rat basophil leukemia (RBL) cells were primed with either IgE$^{dansyl}$ or IgE$^{DNP}$ and then incubated with cHBI$^{dansyl}$ with fluorescein (FITC) tags then analyzed with flow cytometry (Table 9-1, FIG. 32C). The data indicates that cHBI molecules bind significantly more to IgE$^{dansyl}$ rather than IgE$^{DNP}$ on the surfaces of RBL cells at for concentration 10, 100 and 1000 nM, indicating selective binding (FIG. 32C, p<0.01). These results indicate specific attachment of cHBI molecules in the nanomolar range.

cHBIs Demonstrate Degranulation Inhibition In Vitro with Monoclonal Antibodies.

Figure 33A:
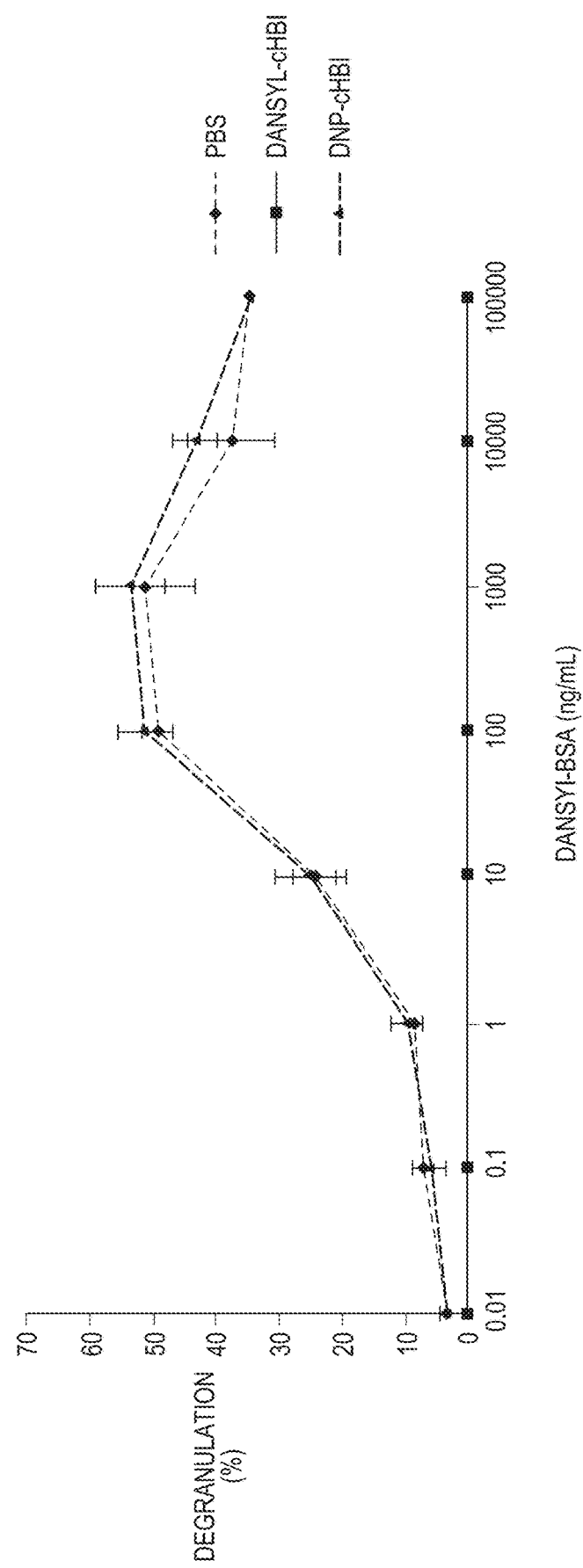
FIG. 33A-C. Dansyl cHBIs inhibit degranulation in vitro using RBL-2H3 cells. Degranulation assay results from RBL cells sensitized with IgE$^{dansyl}$, incubated for 5 hours with 1 µM of either DNP or dansyl cHBI or a PBS control, then challenged with varying concentrations of danysl-BSA (A). Percent degranulation inhibition for dansyl cHBI at various incubation times and concentrations when challenged with 100 ng/mL dansyl-BSA. (B). RBL cells were sensitized and then incubated with dansyl cHBI's at varying concentrations overnight, washed with buffer and then challenged on consecutive days with 100 ng/mL dansyl-BSA.
Figure 33B:
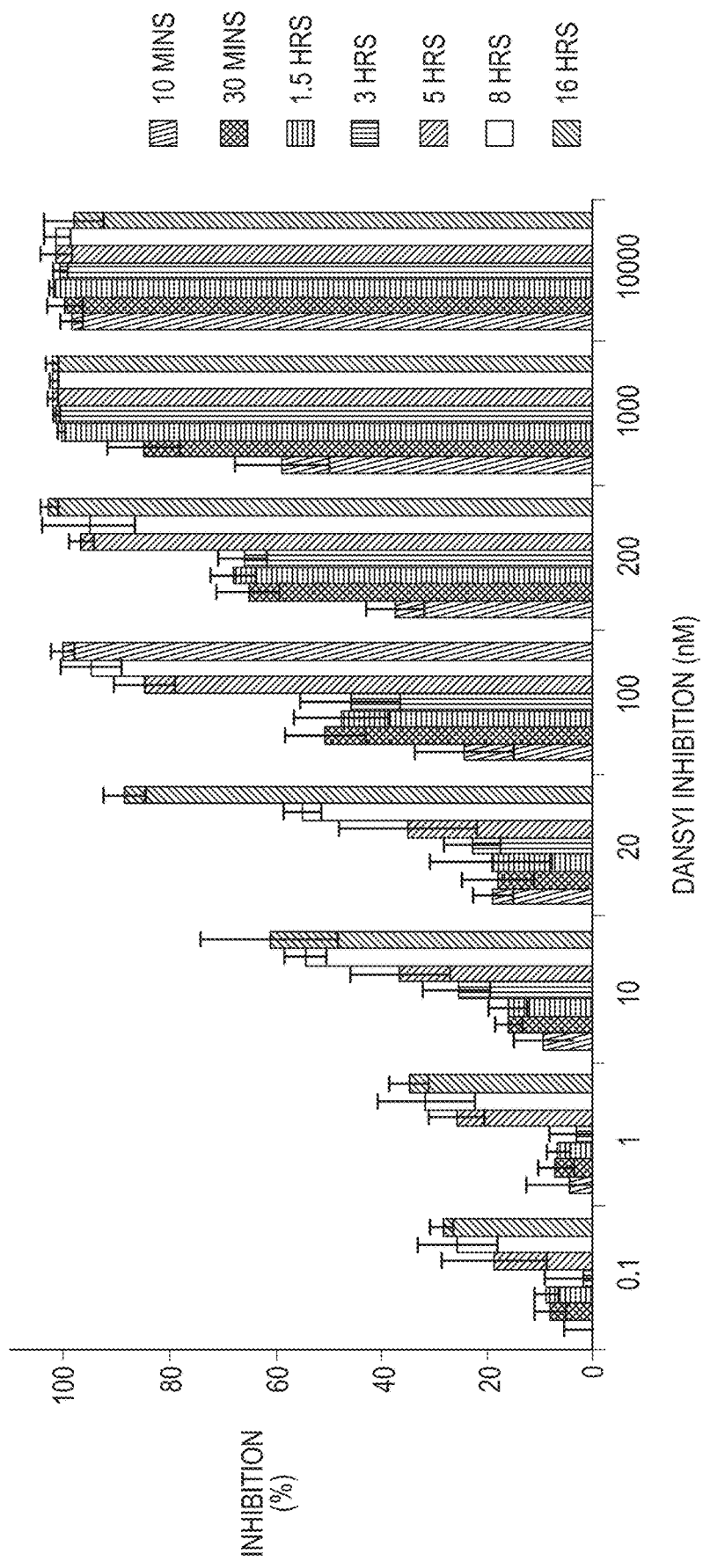
Figure 37:
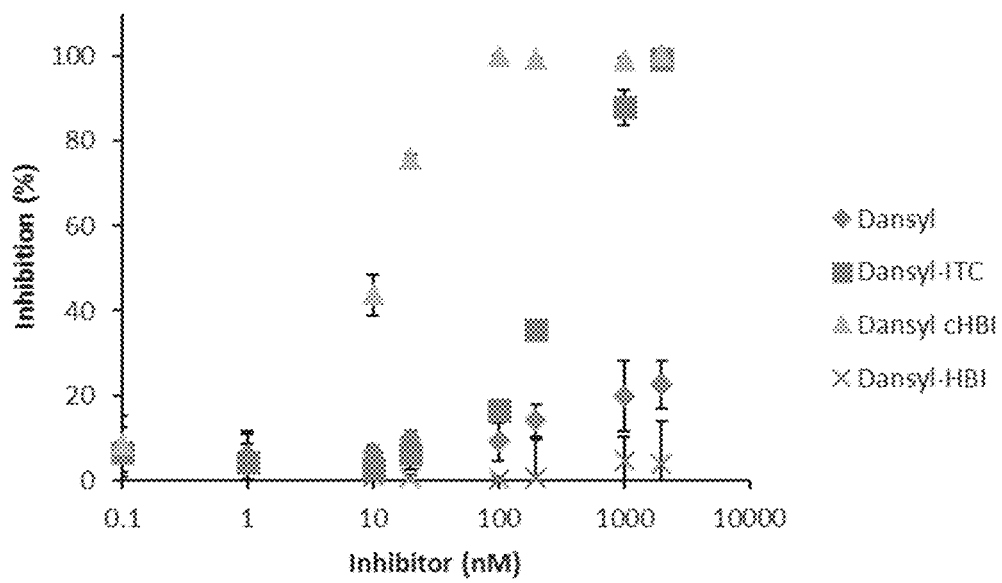
FIG. 37. Degranulation triggered with 1000 ng/mL dansyl-BSA after a 16-hour incubation with inhibitor molecules.
Figure 38:
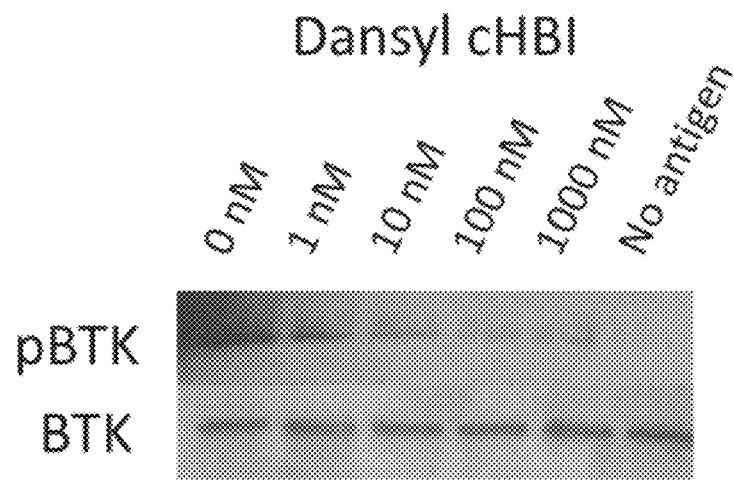
FIG. 38. Western blot of RBL cell lysates after 5-hour incubation with dansyl cHBIs. Degranulation was triggered with 1 µg/mL of dansyl-BSA prior to lysis and probing with anti-BTK or anti-pBTK antibodies.

After confirming the specific covalent attachment of cHBI molecules to allergy reactive IgE's, we next sought to demonstrate inhibition of allergy reactions using an in vitro system. We tested cHBIs with a well-established degranulation assay using rat basophil leukemia (RBL) cells with monoclonal IgEs and haptenized bovine serum albumin (BSA) as the IgE/allergen. As demonstrated by FIG. 33A, when dansyl cHBI was incubated with IgE$^{dansyl}$ primed RBL cells at a constant concentration of 1 µM, there was a complete inhibition of degranulation responses over a wide range of dansyl-BSA allergen stimulation. A cHBI molecule specific to an orthogonal molecule, dinitrophenol (DNP), did not inhibit degranulation responses to dansyl-BSA, demonstrating the specificity of these inhibitors (FIG. 33A). In order to further confirm degranulation inhibition, we observed a marked decrease in phosphorylation of Bruton's tyrosine kinase, a well-established marker for RBL and mast cell degranulation activation (FIG. 37). Likewise, cHBI molecules inhibited degranulation much more effectively than HBI's or hapten-ITC conjugates likely due to washing steps prior to allergen incubation causing most unconjugated molecules to be removed, demonstrating the necessity of all three moieties for proper cHBI design (FIG. 38). Furthermore, these molecules inhibit degranulation over a wide number of experimental conditions, demonstrating their potential clinical versatility. The dansyl cHBI was able to effectively inhibit degranulation at concentrations as low as 20 nM and in as rapidly as 10 minutes (with a dose of 1000 nM, FIG. 33B). The cHBI molecules have long lasting inhibitory effects as well. As demonstrated by FIG. 33C, even after washing away the initial cHBI dose, there was no significant effect in the inhibitory effect of dansyl-cHBI's even after a 72-hour incubation in cell culture media. This indicates that cHBI molecules could provide long lasting inhibition of IgE mediated degranulation to drugs with only a single dose.

cHBIs Inhibit Degranulation to Mouse Sera Primed RBL Cells.

Figure 39:
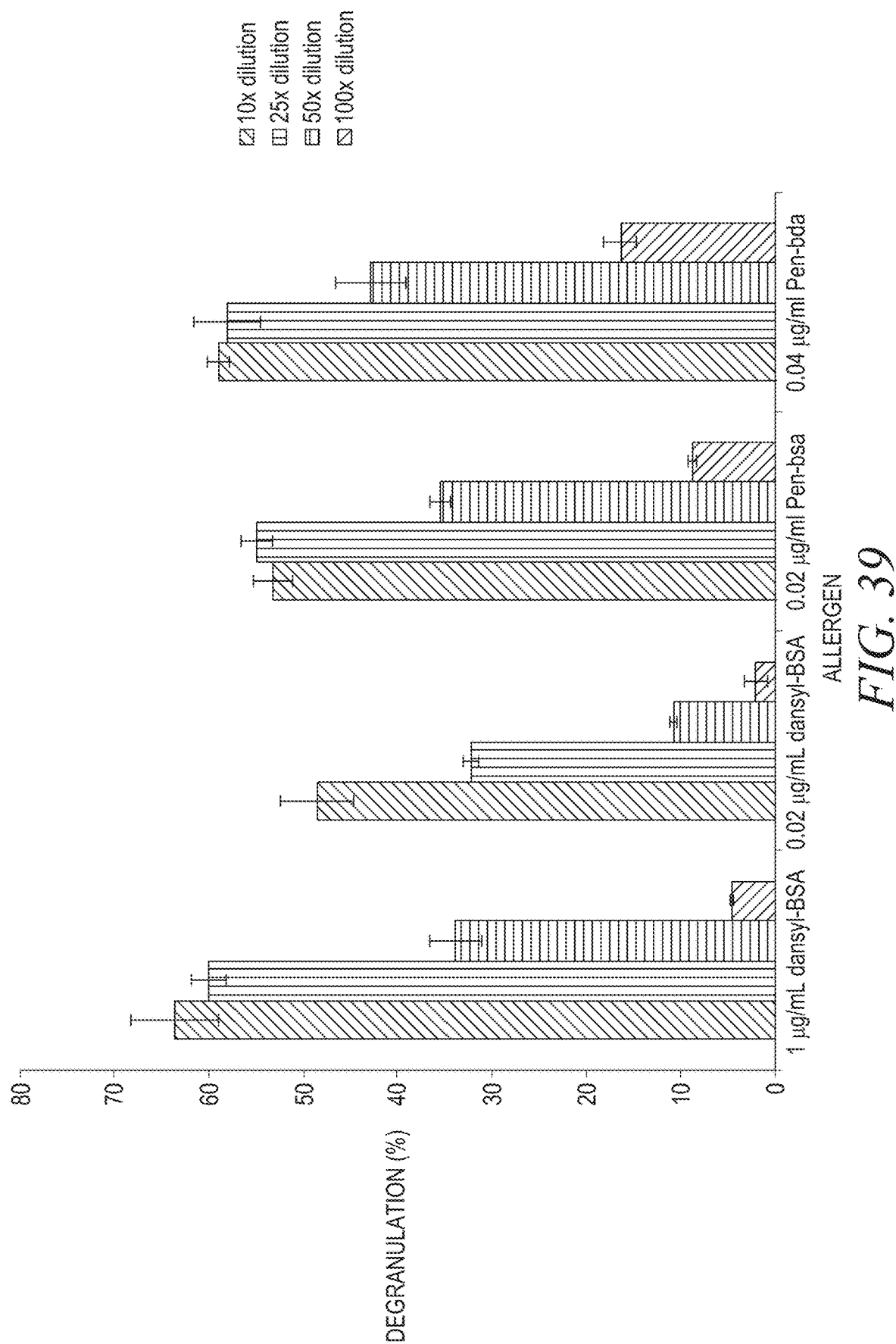
FIG. 39. Pooled mouse sera from 5 mice sensitized to either dansyl-OVA or Pen-OVA were used to sensitize RBL cells at various dilutions of sera. Degranulation was observed to hapten-BSA conjugates.

In order to further examine the cHBIs inhibitory characteristics in a more physiologically relevant in vitro system, we primed RBL cells with serum taken from mice sensitized to ovalbumin (OVA) that had been haptenized with either dansyl or penicillin G (see methods section below). After incubating RBL cells with the reactive sera, degranulation was triggered with either dansyl-BSA or penicilloyl-BSA conjugates confirming the presence of hapten specific IgEs in the sera (FIG. 39). Both the dansyl and penicilloyl cHBI demonstrated significant inhibition of degranulation when exposed to various concentrations of their respective hapten-BSA allergen (p<10$^{-4}$, FIG. 34A). We also varied inhibitor concentrations of both cHBI and HBI molecules to dansyl and penicilloyl to determine optimal concentration ranges. As demonstrated by FIG. 34B, cHBI molecules to both haptens inhibited degranulation in a significant fashion down to 100 nM (p<0.01). The optimal inhibition occurred between 1 and 10 µM for both dansyl and penicilloyl, with a >95% and >80% maximum inhibition respectively (FIG. 34B). Finally, the cHBI's demonstrated a significantly higher inhibition than HBI's at every inhibitor concentration except for the lowest concentration point for dansyl and the lowest two points for penicilloyl, demonstrating the importance of the ITC domain (p<0.05, FIG. 34B). This result demonstrates that cHBI molecules can prevent degranulation to a clinically relevant drug, penicillin, and that cHBI molecules maintain inhibitory characteristics even to a more physiologically relevant polyclonal IgE mixture.

cHBIs Inhibit Degranulation In Vivo.

Finally, in order to further evaluate cHBIs as a potential clinical tool, these molecules were administered to mice that had been previously sensitized to either dansyl or penicillin.

Conclusion.

Figure 33C:
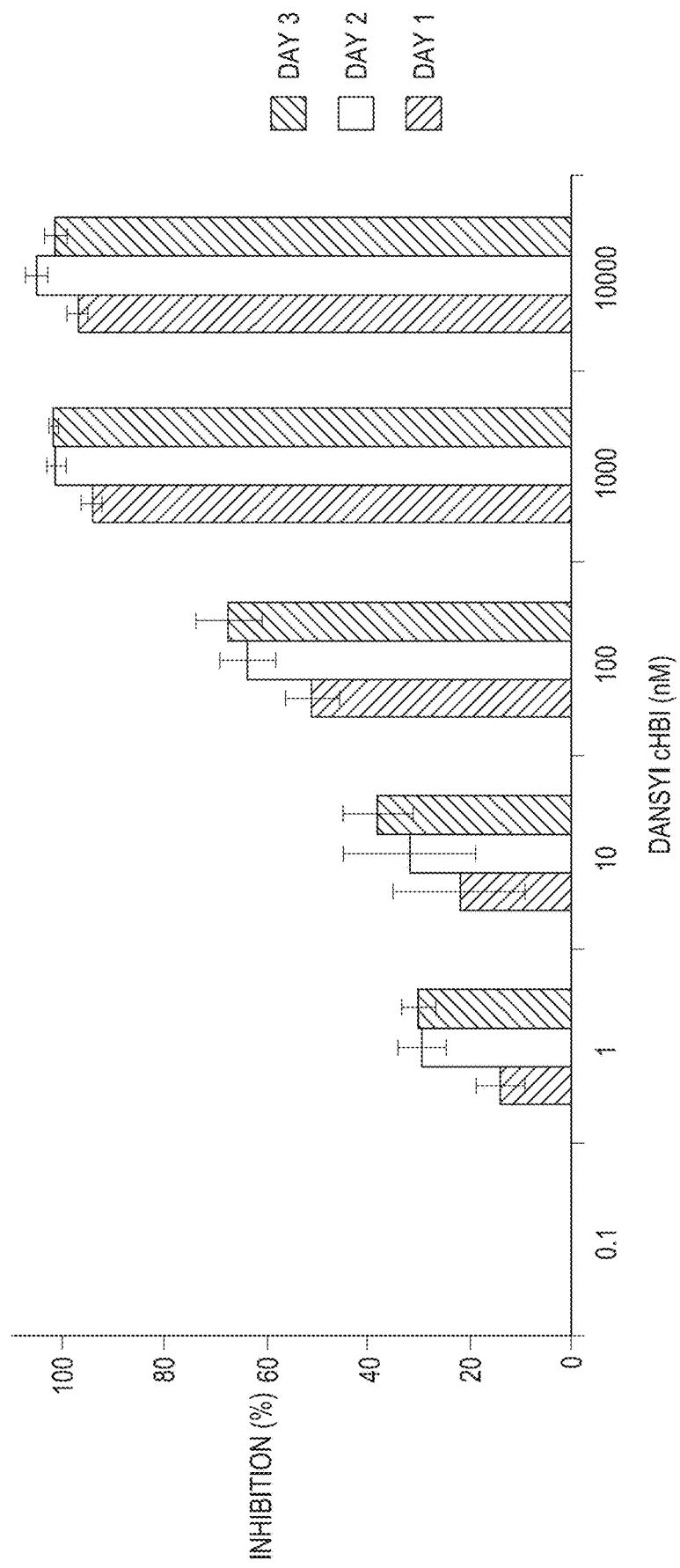
Figure 34:
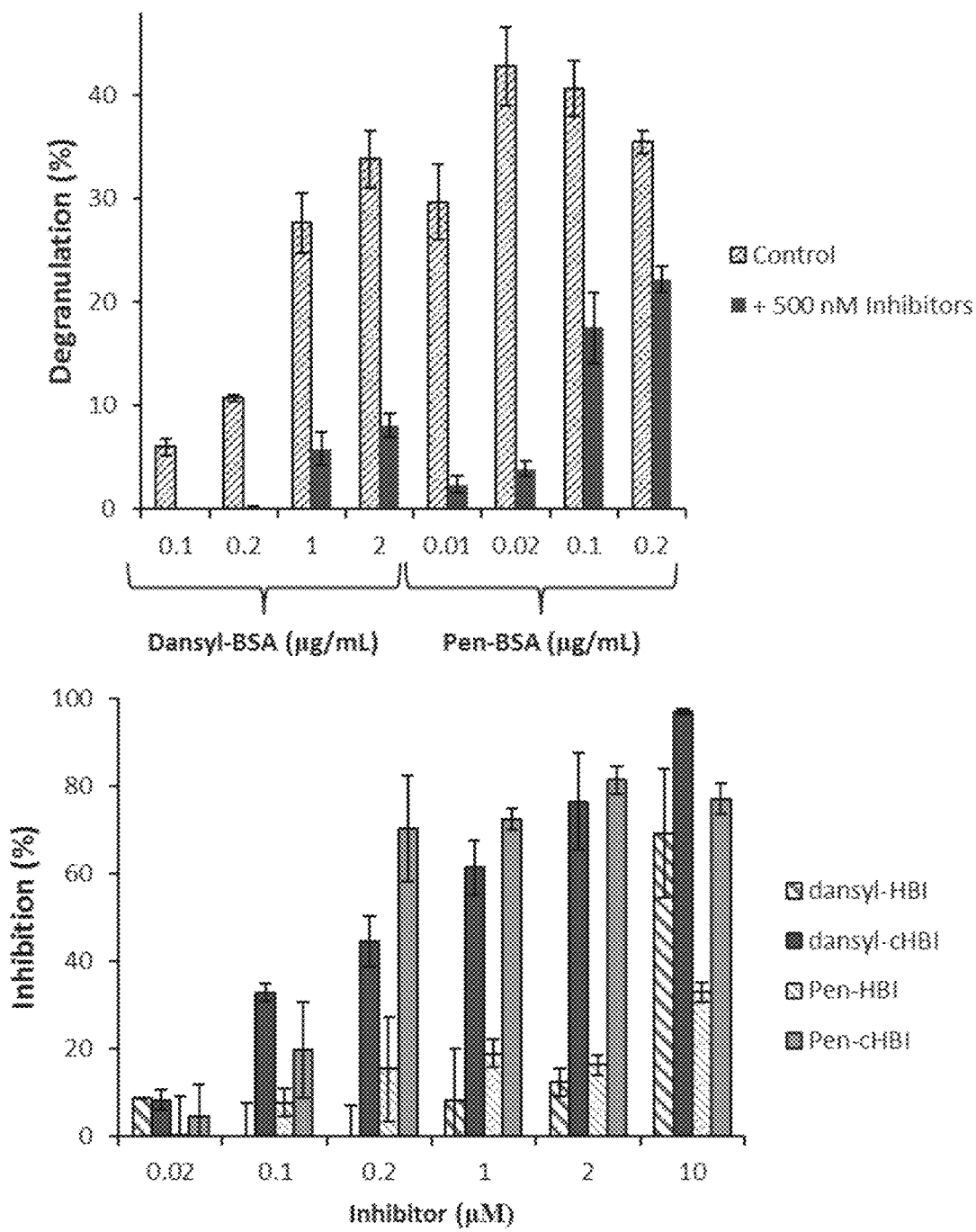
FIG. 34. Degranulation inhibition of RBL cells sensitized with hapten reactive mouse sera (top: % degranulation; bottom: % inhibition).

In this example, we have presented a versatile, effective and selective design for inhibitors to drug induced type I hypersensitivity basophil and mast cell degranulation. These cHBI molecules are potent and selective due to their ability to form specific covalent bonds with lysine side chains near the NBS site of antibodies, effectively permanently preventing hapten specific IgEs from participating in IgE crosslinking and degranulation of basophils and mast cells. Typically, inhibiting IgE crosslinking and degranulation responses to hapenized serum proteins is very challenging due to multiple hapten groups on serum proteins facilitating bivalent binding on single IgE molecules, greatly increasing the apparent avidity of the IgE-hapten complexes. These complexes are very stable and not inhibited by monovalent hapten molecules alone. We overcome this issue by tethering a hapten molecule to a lysine near the ABS, resulting in a large increase in effective concentration of competitive inhibitor which can effectively out-compete haptenized serum proteins for the same binding site. The innovative design of cHBIs makes them very effective and selective. As we have demonstrated in this example, these inhibitors form off target covalent interactions slowly and utilize specific bivalent binding to both ABS and NBS to facilitate a covalent linkage only to the immunoreactive antibodies of interest (FIG. 32). Likewise, these inhibitors selectively inhibit degranulation to only the targeted hapten of interest in vitro (FIGS. 33 and 34).

We also postulate that these inhibitors will be long lasting in a clinical setting as their inhibitory characteristics should persist throughout the course of a mast cell or basophil lifetime, which can be around a month in tissues but shorter in circulating basophils. The exact lifetime of these inhibitors in vivo will require additional research, as our RBL cell cultures restricted assay times, but we were able to demonstrate that these inhibitors completely inhibit hapten-BSA induced responses over the course of at least 72 hours (FIG. 33C). In this example, we also demonstrated that cHBIs bind specifically to their target IgEs and prevent cellular degranulation to drug haptenized proteins both in vitro and in vivo. While we demonstrate the effectiveness to two hapten specific cHBIs, dansyl and penicillin, this design can be modified to accommodate any drug compound such as other penicillin derivatives, sulfa drugs or chemotherapeutics to form the relevant synmimotope-lipid conjugate.

Materials.

NovaPEG Rink Amide resin, 5(6)-carboxy-fluorescein, HBTU (2-(1H-Benzotriazole-1-yl)-1,1,3,3-tetramethyluroniumhexafluorophosphate), Fmoc-Lys(IvDde)-OH, Fmoc-Arg(pfb)-OH, 10 kDa 0.5 mL centrifugal filters and BSA were purchased from EMD Millipore.

DMF (N,N-Dimethylformamide) (>99.8%), DCM (dichloromethane) (>99.8%), DIEA (N,N-Diisopropylethylamine), methanol, hydrazine, piperidine, TFA (trifluoroacetic acid), TIS (triisopropylsilane), Tryptamine, 2-Naphthaleneacetic Acid, ethylene diamine, biotin, $BOC_2O$ (Di-tert-butyl carbonate), DMAP (4-(Dimethylamino)pyridine), Succinic anhydride, $CS_2$ (Carbon disulfide), BDI (butane diisthiolcyanate), THF (Tetrahydrafuran), TPP (triphenylphosphine), DIAD (diisopropylazocarboxylate), MeI (methyl iodide), DNFB (2,4-Dinitro-1-fluorobenzene), acetonitrile, acetic acid, methanol, carbonate-bicarbonate buffer, Tween 20, IBA (Indole-3-butyric acid), Biotin and PBS (phosphate buffered saline), Bicarbonate-carbonate buffer (Bicarb), OVA (ovalbumin), Step-HRP (streptavidin conjugated to HRP), PCMB (p-chloromercuribenzoic acid) were purchased from Sigma Aldrich.

High Binding and Non-Binding 96-well plates were purchased from Corning. Minimum Essential Media, Penicillin-Strep solution, L-glutamine, and Amplex Red ELISA kits were purchased from Life Technologies. Bovine Serum Albumin was purchased from Gemini Biosciences. 96-well Tissue Culture plates were purchased from Falcon. EG2 (Fmoc-N-amido-dPEG$_2$-acid) and EGs (Fmoc-N-amido-dPEGs-acid) were purchased from Quanta biodesign. FITC (Fluorescein Isothiocyanate) was purchased from Toronto Research Chemistry. Tris-Glycine buffer was purchased from VWR. Non-Fat Powdered Milk, transfer buffer (10×), and SDS-Sample Buffer (4×, reducing) were purchased from Boston BioProducts. Tris buffered Saline with 0.05% Tween 20 was purchased from KPL. Chemiluminescence substrate was purchased from Thermo scientific. Anti-dansyl IgE (clone 27-74) and anti-human cyclinA IgE (clone BF683) were purchased from BD Biosciences. Mouse IgG$^{Penicillin}$ (monoclonal antibody clone P2B9) was purchased from Abcam. Anti-DNP IgE (clone SPE-7) was purchased from Sigma Aldrich.

Methods:

cHBI Synthesis.

All hapten conjugated molecules (cHBI, HBI or Hapten-ITC's) were synthesized using Fmoc solid phase peptide synthesis (SPPS) with several modifications. The basic peptide synthesis procedure is described briefly: molecules were conjugated to Rink Amide Low Loading Resin (Millipore), Fmoc-amino acids and Fmoc protected ethylene glycol spacers and Napht were dissolved at 4-fold excess in DMF, activated with a 3.6-fold excess of HBTU with 20 fold DIEA for five minutes prior to addition. DNP was added as DNFB and dansyl was added as dansyl chloride at 4 fold excesses in DMF with 20 fold DIEA. Activated Fmoc protected amino acids, haptens and Napht were reacted with amines on resin for 30 minutes for each step. After addition, resin was washed three times with DMF, and deprotected with 20% piperidine in DMF for 3 minutes three times. Following deprotection, resin was washed with DMF and DCM. Following Napht addition, the IvDdE group of lysine was deprotected using 2% hydrazine in DMF in the same fashion.

ITC domains were always added just prior to cleavage from resin. For dansyl and DNP cHBI molecules primary amines were chemically modified into ITC moieties using a modified procedure from Munch et al (FIG. 39). Briefly, resins with deprotected primary amines were washed in anhydrous DMF three times. A tenfold excess $CS_2$ with a 20-fold excess of DIEA was added in DMF and allowed to react for 30 minutes. Resin was then drained and washed once with anhydrous DMF. One mL of DMF with a 20-fold excess of DIEA was added to resin and cooled to approximately 0° C. in −20° C. freezer. Then, a 2-fold excess of $Boc_2O$ and 0.2 fold of DMAP was added to vessel and allowed to react for 20 minutes at −20° C. Vessel was removed, allowed to warm to room temperature for thirty minutes and then washed with DMF, DCM and diethyl ether and allowed to dry in vacuum chamber.

Penicillin cHBI molecules had two different chemistries in order to maintain proper ITC functionality. Prior to penicillin addition, penicillin in solution was reacted with ethylene diamine to open beta lactam ring and purified, forming a penicilloyl-NH$_2$. Then resins with deprotected amines were reacted with succinic anhydride to leave a terminal carboxylic acid group. This group was then activated with an equimolar amount of HBTU in 5-fold excess of DIEA in DMF for 10 minutes. Resin was washed with DMF and then a 4-fold excess of penicilloyl-NH$_2$ was added with 20-fold excess of DIEA in DMF and allowed to react for 30 minutes. The penicilloyl conjugate contains a secondary amine which is reactive to ITC. So, in order to prevent HBI cyclization, this secondary amine was methylated into a tertiary amine following a procedure by Kurosu et al. Following reaction, the resin was washed several times with DMF and synthesis continued following IvDdE deprotection. Additionally, in order to improve overall cHBI yields, ITC was conjugated by addition of bifunctional ITC molecules, BDI. BDI was added to free amines in a 10-fold excess in DMF with DIEA and allowed to react for two hours. This was the final step prior to cHBI cleavage.

Molecules were cleaved from the resin using a 95/2.5/2.5 TFA/water/TIS mixture for two cycles for 45 minutes each. The resulting solution was rotovapped to remove TFA, rehydrated in 50/50 ACN/water and purified by RP-HPLC using an Agilent 1200 series HPLC with a Zorbax C18 semi prep column using a ACN/water gradient between 20-60% ACN in 10 minutes with a flow rate of 4 mL/min. Product was collected, rotovapped, lyophilized and re-dissolved in DMSO. Concentration was determined by absorbance at 280 nm or 335 nm. All molecules were characterized using high resolution MicroTOF MS analysis. Purity was determined by analytical RP-HPLC using Zorbax Eclipse XBD-C18 with a 20-60% ACN gradient (Table 9-1).

Molecules used in ELISA and flow cytometry contained either a biotin or fluorescein (FITC) tag that was incorporated onto resin prior to molecule synthesis. In each case, Fmoc-Lys(IvDdE)-OH was attached first to the resin, deprotected on Fmoc amine, conjugated to Fmoc-EG2-OH, deprotected again and conjugated to either Biotin activated with HBTU or FITC. Then, IvDdE group is deprotected and synthesis is continued for either penicillin or dansyl cHBIs.

Fluorescence Quenching.

In order to determine binding of HBI molecules to respective antibodies, we observed the quenching of tryptophan resides using a method previously described. Briefly, either $IgE^{dansyl}$ or $IgG^{Penicillin}$ was diluted into a non-binding 96-well dish at 40 nM in PBS. Then, HBI molecules which contained either a dansyl or DNP group were titrated into well and fluorescence (Ex. 280 nm, Em. 335) was observed using a SpectraMax M2 spectrophotometer. PBS and free tryptamine diluted to similar initial fluorescence values were used as controls to account for HBI fluorescence and non-specific quenching respectively.

In Solution Conjugation of cHBI Molecules.

Before ELISA analysis of cHBI-antibody conjugates, we performed an in solution conjugation of cHBI molecules and antibodies allowing ITC moieties to react with primary amines on antibody proteins. Either dansyl or penicillin cHBI molecules at various concentrations were incubated with either $IgE^{dansyl}$ or $IgE^{DNP}$ (as control) or $IgG^{Penicillin}$ or BSA (as control) at 1 µM concentrations for various incubation times in either PBS (pH 7.4) or Bicarbonate-Carbonate Buffer (pH 9.6) at 50 µL total volumes at 37° C. After reaction, excess cHBI molecules were removed using membrane filtration with 10 kDa 0.5 mL Centrifugal Filters (Millipore) by washing antibodies three times in PBS. Purified antibodies were analyzed with a SpectraMax M5 spectrophotometer at 280 nm using an extinction coefficient of 200,000 cm$^{-1}$ M$^{-1}$ for $IgE^{DNP}$ and $IgE^{dansyl}$ and 150,000 cm$^{-1}$ M$^{-1}$ for $IgG^{Penicillin}$.

ELISA.

Binding of cHBI molecules to antibodies was observed using a direct ELISA. 100 µL of 2 nM antibody or BSA molecules previously reacted with cHBIs that were labeled with biotin were incubated for 2 hours in bicarbonate buffer on a high binding 96-well plate. Plates were washed with a AquaMax 2000 plate-washer to remove unbound antibody. Wells were blocked with a 5% BSA, 0.2% Tween 20 solution in PBS for 1 hour, washed and incubated with a streptavidin conjugated to HRP for 1 hour in blocking buffer. Plate was washed again and an Amplex Red Kit was used to quantify ELISA signal using a SpectraMax M5 spectrophotometer according to manufacturer's instruction.

Cell Culture.

RBL-2H3 cells were cultured as previously described, split every 48-72 hours at a 1:3 dilution into fresh RBL-2H3 media. Plates for experiments were prepared at roughly 500,000 cells per mL in either 0.5 mL or 100 µL wells on tissue culture plates.

Flow Cytometry.

Flow cytometry was performed on RBL-2H3 cells using a Guava easyCyte 8HT in order to demonstrate dansyl cHBI molecule attachment under more physiological conditions. RBL-2H3 cells split at 500,000 cells per mL into a 24-well dish (0.5 mL each) and allowed to attach to plate overnight. Following morning, 0.5 µg of $IgE^{DNP}$ or $IgE^{dansyl}$ was added and allowed to incubate for 24 hours. Cells were then washed twice with sterile PBS, and incubated with fresh media with dansyl cHBI-FITC between 0-1000 nM for 16 hours. Cells were then washed again with PBS and given fresh media, then chilled on ice for 30 minutes. Cells were washed with PBS and incubated in 1.5% BSA in PBS, scrapped and analyzed.

Protein-Hapten Conjugates.

Protein-Hapten conjugates were prepared in order to sensitize mice for allergen challenges and to trigger in vitro degranulation. Two different haptens, penicillin and dansyl chloride were used with two different protein carriers, OVA and BSA. OVA conjugates while BSA conjugates were used to trigger degranulation and perform allergen challenges. Dansyl was conjugated to OVA and BSA by dissolving 20 mg of BSA or OVA in 3 mL bicarbonate-carbonate buffer (pH 9.6) and then adding 20 mg of dansyl chloride that was dissolved in DMF. These compounds reacted under mild stirring over 24 hours at 37° C. After reaction, products were passed through a 0.22 µM filter and filtered using 10 kDa membrane filtration to remove excess dansyl. Using a dansyl extinction coefficient of 3400 cm M$^1$ at 335 nm, and an extinction coefficient of 43800 and 30950 cm$^{-1}$ M$^{-1}$ at 280 nm for BSA and OVA respectively and a dansyl correction factor of 0.39 to correct for dansyl absorbance at 280 nm. Using the ratios of absorbance at 335/280 nm, we determined dansyl-BSA to have 18 dansyl per protein and dansyl-OVA to have 12 dansyl per protein.

For penicillin conjugates, performed a similar addition of hapten to protein, except using 200 mg of penicillin G salt and allowing reaction to take place over 72 hours. Penicillin-protein conjugates were filtered in a similar manner as dansyl. In order to determine conjugation efficiency, we used a Penmaldate assay from Levine et. al. We determined penicillin-BSA to have 12 penicillin per protein while penicillin-OVA had 8 penicillin per protein.

Degranulation Assay.

All of these degranulation assays followed this basic procedure: (1) RBL cells previously primed with IgEs (either from monoclonal sources or mouse sera from mouse sensitization below) were incubated with cHBIs for varying amounts of time, (2) cells were washed to remove any unbound or unconjugated cHBIs, (3) allergen was added to stimulate degranulation. Briefly, 50,000 cells were incubated in a 96-well tissue culture plate and either mixtures of monoclonal antibodies (with 25% $IgE^{dansyl}$ and 75% orthogonal $IgE^{cyclinA}$) to a final concentration of 1 µg/mL or dilutions of mouse sera were added for 24 hours. Cells were then washed with sterile PBS and cHBI compounds were added at various dilutions for varying time points. Cells were then washed with tyrodes buffer and degranulation was triggered using either dansyl-BSA or penicillin-BSA as previously described. Percent inhibition was calculated by dividing percent degranulation with cHBI's by control without cHBI for same allergen concentration. For experiments in FIG. 33C, after incubating with inhibitors for 24 hours, cells were washed and allowed to incubate in cell culture media between 24-72 hours before testing degranulation response.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A liposomal nanoparticle comprising:
   about 0.1 mol % to about 20 mol % of a synmimotope-lipid conjugate;
   about 2 mol % to about 10 mol % of a polyethylene glycol-lipid (PEG-lipid) conjugate; and
   about 80 mol % to about 97 mol % of 1,2-distearoyl-sn-glycero-3-phosphocholine (DSPC);
   wherein
   the nanoparticle comprises a spherical lipid bilayer comprising the phospholipid and the synmimotope-lipid conjugate, the spherical lipid bilayer having an interior surface and an exterior surface;
   the exterior surface of the spherical lipid bilayer comprises the PEG-lipid conjugate wherein PEG moieties of the PEG-lipid conjugate form a coating over the exterior surface of the nanoparticle, and one or more synmimotope moieties of synmimotope-lipid conjugates protrude above the coating formed by the PEG moieties;
   wherein the synmimotope-lipid conjugate comprises a conjugate of Formula I:

A-B-C-D-E-(F)n    (I)

wherein
   A is a synmimotope moiety of the synmimotope-lipid conjugate, wherein the synmimotope moiety is a hapten moiety comprising 2,4-dinitrophenol (DNP);
   B is a first linker, wherein the first linker comprises two ethylene glycol moieties covalently attached to the synmimotope moiety (A) and second linker (C) by amide bonds; and
   C is the second linker, wherein the second linker (C) comprises three lysine amino acids covalently attached by amide bonds to the first linker (B); and
   D is a third linker, wherein the third linker (D) comprises three ethylene glycol$_6$ moieties attached covalently at distal ends by amide bonds to the second linker (C) and tag (E);
   E is the tag, wherein the tag comprises a tryptophan residue;
   F is a palmitoyl moiety covalently attached to the tag (E) by an amide bond; and
   n is 2;
   wherein the diameter of the nanoparticle is about 20 nm to about 2 µm.

2. The nanoparticle of claim 1 wherein the PEG-lipid conjugate comprises about 10 to about 200 ethylene glycol residues and the lipid is a ($C_8$-$C_{22}$)acyl moiety or a phospholipid, wherein the ethylene glycol residues and the lipid are optionally linked by an amide bond.

3. The nanoparticle of claim 1 wherein the nanoparticle has a diameter of about 20 nm to about 300 nm.

4. The nanoparticle of claim 1 wherein the nanoparticle further comprises a plurality of allergen epitopes protruding above the coating formed by the PEG moieties, wherein the plurality of allergen epitopes is homogeneous or heterogeneous.

5. The nanoparticle of claim 1 wherein the nanoparticle comprises:
about 2 mol % synmimotope-lipid conjugate;
about 5 mol % PEG-lipid conjugate; and
about 93 mol % 1,2-distearoyl-sn-glycero-3-phosphocholine (DSPC).

6. The nanoparticle of claim 1 further comprising about 1 mol % to about 35 mol % cholesterol, with respect to the molar amount of the 1,2-distearoyl-sn-glycero-3-phosphocholine (DSPC).

7. A liposomal nanoparticle comprising:
about 0.1 mol % to about 20 mol % of a synmimotope-lipid conjugate;
about 2 mol % to about 10 mol % of a polyethylene glycol-lipid (PEG-lipid) conjugate; and
about 80 mol % to about 97 mol % of 1,2-distearoyl-sn-glycero-3-phosphocholine (DSPC);
wherein
the nanoparticle comprises a spherical lipid bilayer comprising the phospholipid and the synmimotope-lipid conjugate, the spherical lipid bilayer having an interior surface and an exterior surface;
the exterior surface of the spherical lipid bilayer comprises the PEG-lipid conjugate wherein PEG moieties of the PEG-lipid conjugate form a coating over the exterior surface of the nanoparticle, and one or more synmimotope moieties of synmimotope-lipid conjugates protrude above the coating formed by the PEG moieties, wherein the one or more synmimotope moieties protruding above the coating are homogeneous;
wherein the synmimotope-lipid conjugate comprises a conjugate of Formula I:

$$A\text{-}B\text{-}C\text{-}D\text{-}E\text{-}(F)n \qquad (I)$$

wherein
A is a synmimotope moiety of the synmimotope-lipid conjugate, wherein the synmimotope moiety is a hapten moiety comprising 2,4-dinitrophenol (DNP);
B is a first linker, wherein the first linker comprises two ethylene glycol moieties covalently attached to the synmimotope moiety (A) and second linker (C) by amide bonds; and
C is the second linker, wherein the second linker (C) comprises three lysine amino acids covalently attached by amide bonds to the first linker (B); and
D is a third linker, wherein the third linker (D) comprises three ethylene glycol$_6$ moieties attached covalently at distal ends by amide bonds to the second linker (C) and tag (E);
E is the tag, wherein the tag comprises a tryptophan residue;
F is a palmitoyl moiety covalently attached to the tag (E) by an amide bond; and
n is 2;
wherein the diameter of the nanoparticle is about 20 nm to about 300 nm.

* * * * *

```
                       SEQUENCE LISTING

<160> NUMBER OF SEQ ID NOS: 31

<210> SEQ ID NO 1
<211> LENGTH: 7
<212> TYPE: PRT
<213> ORGANISM: Arachis hypogaea

<400> SEQUENCE: 1

Ser Pro Ile Leu Tyr His Tyr
1               5

<210> SEQ ID NO 2
<211> LENGTH: 6
<212> TYPE: PRT
<213> ORGANISM: Arachis hypogaea

<400> SEQUENCE: 2

Pro Pro Arg Gly Leu Phe
1               5

<210> SEQ ID NO 3
<211> LENGTH: 7
<212> TYPE: PRT
<213> ORGANISM: Arachis hypogaea

<400> SEQUENCE: 3

Met Ser Asp Arg Gly Ile Phe
1               5

<210> SEQ ID NO 4
<211> LENGTH: 6
<212> TYPE: PRT
<213> ORGANISM: Arachis hypogaea

<400> SEQUENCE: 4

Val Cys Pro Gly Ser Lys
1               5

<210> SEQ ID NO 5
<211> LENGTH: 16
<212> TYPE: PRT
<213> ORGANISM: Arachis hypogaea

<400> SEQUENCE: 5

Asn Leu Arg Pro Cys Glu Gln His Leu Met Gln Lys Ile Gln Arg Asp
1               5                   10                  15

<210> SEQ ID NO 6
<211> LENGTH: 15
<212> TYPE: PRT
<213> ORGANISM: Arachis hypogaea
<220> FEATURE:
<221> NAME/KEY: MOD_RES
<222> LOCATION: (7)..(7)
<223> OTHER INFORMATION: hydroxyproline post-translational modifications
      that were incorporated into the epitope-lipid conjugate
<220> FEATURE:
<221> NAME/KEY: MOD_RES
<222> LOCATION: (14)..(14)
<223> OTHER INFORMATION: hydroxyproline post-translational modifications
``` that were incorporated into the epitope-lipid conjugate

<400> SEQUENCE: 6

Glu Arg Asp Pro Tyr Ser Pro Ser Gln Asp Pro Tyr Ser Pro Ser
1               5                   10                  15

<210> SEQ ID NO 7
<211> LENGTH: 9
<212> TYPE: PRT
<213> ORGANISM: Arachis hypogaea

<400> SEQUENCE: 7

Ser Asp Arg Leu Gln Gly Arg Gln Gln
1               5

<210> SEQ ID NO 8
<211> LENGTH: 9
<212> TYPE: PRT
<213> ORGANISM: Arachis hypogaea

<400> SEQUENCE: 8

Arg Arg Cys Gln Ser Gln Leu Glu Arg
1               5

<210> SEQ ID NO 9
<211> LENGTH: 10
<212> TYPE: PRT
<213> ORGANISM: Arachis hypogaea

<400> SEQUENCE: 9

His Ala Ser Ala Arg Gln Gln Trp Glu Leu
1               5                   10

<210> SEQ ID NO 10
<211> LENGTH: 17
<212> TYPE: PRT
<213> ORGANISM: Arachis hypogaea

<400> SEQUENCE: 10

Arg Gln Gln Glu Gln Gln Phe Lys Arg Glu Leu Arg Asn Leu Pro Gln
1               5                   10                  15

Gln

<210> SEQ ID NO 11
<211> LENGTH: 7
<212> TYPE: PRT
<213> ORGANISM: Arachis hypogaea

<400> SEQUENCE: 11

Pro Gln Arg Cys Asp Leu Glu
1               5

<210> SEQ ID NO 12
<211> LENGTH: 13
<212> TYPE: PRT
<213> ORGANISM: Arachis hypogaea

<400> SEQUENCE: 12

Cys Asp Leu Glu Val Glu Ser Gly Gly Arg Asp Arg Tyr
1               5                   10

<210> SEQ ID NO 13
<211> LENGTH: 15
<212> TYPE: PRT

```
<213> ORGANISM: Arachis hypogaea

<400> SEQUENCE: 13

Ile Glu Thr Trp Asn Pro Asn Asn Gln Glu Phe Glu Cys Ala Gly
1               5                   10                  15

<210> SEQ ID NO 14
<211> LENGTH: 15
<212> TYPE: PRT
<213> ORGANISM: Arachis hypogaea

<400> SEQUENCE: 14

Gly Asn Ile Phe Ser Gly Phe Thr Pro Glu Phe Leu Glu Gln Ala
1               5                   10                  15

<210> SEQ ID NO 15
<211> LENGTH: 15
<212> TYPE: PRT
<213> ORGANISM: Arachis hypogaea

<400> SEQUENCE: 15

Val Thr Val Arg Gly Gly Leu Arg Ile Leu Ser Pro Asp Arg Lys
1               5                   10                  15

<210> SEQ ID NO 16
<211> LENGTH: 15
<212> TYPE: PRT
<213> ORGANISM: Arachis hypogaea

<400> SEQUENCE: 16

Asp Glu Asp Glu Tyr Glu Tyr Asp Glu Glu Asp Arg Arg Arg Gly
1               5                   10                  15

<210> SEQ ID NO 17
<211> LENGTH: 14
<212> TYPE: PRT
<213> ORGANISM: Arachis hypogaea

<400> SEQUENCE: 17

Met Arg Arg Glu Arg Gly Arg Gly Gln Asp Ser Ser Ser Ser
1               5                   10

<210> SEQ ID NO 18
<211> LENGTH: 11
<212> TYPE: PRT
<213> ORGANISM: Arachis hypogaea

<400> SEQUENCE: 18

Lys Pro Cys Glu Gln His Ile Met Gln Arg Ile
1               5                   10

<210> SEQ ID NO 19
<211> LENGTH: 7
<212> TYPE: PRT
<213> ORGANISM: Arachis hypogaea

<400> SEQUENCE: 19

Tyr Asp Ser Tyr Asp Ile Arg
1               5

<210> SEQ ID NO 20
<211> LENGTH: 12
<212> TYPE: PRT
<213> ORGANISM: Arachis hypogaea
```

```
<400> SEQUENCE: 20

Cys Asp Glu Leu Asn Glu Met Glu Asn Thr Gln Arg
1               5                   10

<210> SEQ ID NO 21
<211> LENGTH: 13
<212> TYPE: PRT
<213> ORGANISM: Arachis hypogaea

<400> SEQUENCE: 21

Cys Glu Ala Leu Gln Gln Ile Met Glu Asn Gln Cys Asp
1               5                   10

<210> SEQ ID NO 22
<211> LENGTH: 10
<212> TYPE: PRT
<213> ORGANISM: Arachis hypogaea

<400> SEQUENCE: 22

Lys Arg Glu Leu Arg Met Leu Pro Gln Gln
1               5                   10

<210> SEQ ID NO 23
<211> LENGTH: 13
<212> TYPE: PRT
<213> ORGANISM: Arachis hypogaea

<400> SEQUENCE: 23

Cys Asn Phe Arg Ala Pro Gln Arg Cys Asp Leu Asp Val
1               5                   10

<210> SEQ ID NO 24
<211> LENGTH: 13
<212> TYPE: PRT
<213> ORGANISM: Penaeus aztecus

<400> SEQUENCE: 24

Val His Asn Leu Gln Lys Arg Met Gln Gln Leu Glu Asn
1               5                   10

<210> SEQ ID NO 25
<211> LENGTH: 15
<212> TYPE: PRT
<213> ORGANISM: Penaeus aztecus

<400> SEQUENCE: 25

Ala Leu Asn Arg Arg Ile Gln Leu Leu Glu Glu Asp Leu Glu Arg
1               5                   10                  15

<210> SEQ ID NO 26
<211> LENGTH: 5
<212> TYPE: PRT
<213> ORGANISM: Penaeus aztecus

<400> SEQUENCE: 26

Asp Glu Glu Arg Met
1               5

<210> SEQ ID NO 27
<211> LENGTH: 8
<212> TYPE: PRT
<213> ORGANISM: Penaeus aztecus

<400> SEQUENCE: 27
```

```
<210> SEQ ID NO 28
<211> LENGTH: 11
<212> TYPE: PRT
<213> ORGANISM: Penaeus aztecus

<400> SEQUENCE: 28

Glu Ser Lys Ile Val Glu Leu Glu Glu Leu
1               5                   10

<210> SEQ ID NO 29
<211> LENGTH: 9
<212> TYPE: PRT
<213> ORGANISM: Penaeus aztecus

<400> SEQUENCE: 29

Lys Glu Val Asp Arg Leu Glu Asp Glu
1               5

<210> SEQ ID NO 30
<211> LENGTH: 8
<212> TYPE: PRT
<213> ORGANISM: Penaeus aztecus

<400> SEQUENCE: 30

Lys Tyr Lys Ser Ile Thr Asp Glu
1               5

<210> SEQ ID NO 31
<211> LENGTH: 9
<212> TYPE: PRT
<213> ORGANISM: Penaeus aztecus

<400> SEQUENCE: 31

Glu Leu Asp Gln Thr Phe Ser Glu Leu
1               5
```

(Preceding line from prior page:)
Leu Glu Asn Gln Leu Lys Glu Ala
1               5